US009297017B2

(12) United States Patent
Sheard et al.

(10) Patent No.: US 9,297,017 B2
(45) Date of Patent: Mar. 29, 2016

(54) METHODS AND COMPOSITIONS FOR TARGETED PROTEIN DEGRADATION

(75) Inventors: Laura Sheard, Seattle, WA (US); Ning Zheng, Shoreline, WA (US); Ran Brosh, New York, NY (US); Ihor R. Lemischka, Princeton, NJ (US)

(73) Assignee: University of Washington, Seattle, WA (US)

( * ) Notice: Subject to any disclaimer, the term of this patent is extended or adjusted under 35 U.S.C. 154(b) by 41 days.

(21) Appl. No.: 13/702,988

(22) PCT Filed: Jun. 8, 2011

(86) PCT No.: PCT/US2011/039676
§ 371 (c)(1),
(2), (4) Date: Apr. 29, 2013

(87) PCT Pub. No.: WO2011/156524
PCT Pub. Date: Dec. 15, 2011

(65) Prior Publication Data
US 2013/0227716 A1    Aug. 29, 2013

Related U.S. Application Data

(60) Provisional application No. 61/352,758, filed on Jun. 8, 2010.

(51) Int. Cl.
| C12N 15/00 | (2006.01) |
| C12N 15/81 | (2006.01) |
| C07K 14/415 | (2006.01) |
| C12N 15/62 | (2006.01) |

(52) U.S. Cl.
CPC .............. *C12N 15/81* (2013.01); *C07K 14/415* (2013.01); *C12N 15/62* (2013.01)

(58) Field of Classification Search
CPC ....... C12N 15/81; C12N 15/62; C07K 14/415
USPC .................................................. 435/455, 483
See application file for complete search history.

(56) References Cited

PUBLICATIONS

Thines et al (Nature. 2007, 448 (7154), 661-665.*
Thines el al Nature, 2007, 448, 661-665,.*
NCBI accession No. Q9LMA8 , p. 1.*
Nishimra et al Nature Methods, Nov. 15, 2009),.*
Kastir et al Proc. Natl. Acad Sci, USA, 2008, 105, 7100-7105.*
NCBI accession No. O04197, p. 1.*
Zhou et al (Molecular Cell, 2000, 751-756).*
Sheard et al Nature, 2010, 468, 400-405.*
Mosblech et al The Plant Journal (2011) 65, 949-957.*
Thines el al (Nature, 2007, 448,661-665.*
Nishimura et al (Nature Methods, 2009, 917-923.*
Thines et al., "JAZ Repressor Proteins are Targets of the SCF (COI1) Complex During Jasmonate Signalling," Nature, 448:7154, pp. 661-665 (Aug. 9, 2007).
Theologis et al., Protein TIFY 10A (Jasmonate ZIM domain-containing protein 1). UniprotKB/TrEMBL Accession Q9LMA8. Retrieved from the internet: URL: http://www.uniprot.org/uniprot/Q9LMA8.txt? version=30>,pp. 1-3, (retrieved on Nov. 10, 2011).
Xie et al., Coronatine-insensitive Protein 1 (F-box/LRR-repeat protein 2)(AtFBL2). UniprotKB/TrEMBL Accession O04197. Retrieved from the internet: URL: http://www.uniprot.org/uniprot/004197.txt? version=22>, pp. 1-4, (retrieved on Jan. 11, 2012).
Sheard et al., "Jasmonate Perception by Inositol-phosphate-potentiated COI1-JAZ co-receptor," Nature, ePub, 468:7322, pp. 400-405 (Oct. 6, 2010).
Zhou et al., "Harnessing the Ubiquitination Machinery to Target the Degradation of Specific Cellular Proteins," Mol. Cell. 6:751-756 (Sep. 2000).
Sakamoto et al., "Protacs" Chimeric Molecules that Target Proteins to the Skp1-Cullin-F Box Complex for Ubiquitination and Degradation, PNAS; 98:15 8554-8559 (Jul. 17, 2001).
Zhang, et al., "Exploring the Functional Complexity of Cellular Proteins by Protein Knockout," PNAS; 100:24 14127-14132 (Nov. 25, 2003).
Nishimura et al., "An Auxin-Based Degron System for the Rapid Depletion of Proteins in Nonplant Cells," Nature Meth. 6:12 917-922 (Dec. 2009).

\* cited by examiner

*Primary Examiner* — Anoop Singh
(74) *Attorney, Agent, or Firm* — Perkins Coie LLP

(57) ABSTRACT

Coronatine has been found to enhance binding of the JAZ1 degron to the *Arabidopsis* F-box protein COI1, and analysis of the JAZ1 degron sequence has resulted in the identification of specific peptide sequences that bind COI1 with high affinity in the presence of coronatine. Crystal structure analysis has determined that coronatine and JA-Ile enhance the interaction between COI1 and JAZ1 via binding to a specific binding pocket on COI1. Attachment of one or more JAZ1 peptide tags as disclosed herein to a target protein in a nonplant cell expressing *Arabidopsis* COI1 or a homolog thereof results in degradation of the target protein following addition of a molecule that binds the coronatine/JA-Ile binding pocket on COI1. Therefore, provided herein are compositions, methods, and kits for targeted protein degradation.

3 Claims, 25 Drawing Sheets

A.

B.

A.

B.

A.

B.

C.

A.

B.

C.

A.

B.

A.

B.

A.

B.

C.

A.

B.

A.

B.

A.

B.

C.

A.

B.

SEQUENCE LISTING

```
<160> NUMBER OF SEQ ID NOS: 31

<210> SEQ ID NO 1
<211> LENGTH: 22
<212> TYPE: PRT
<213> ORGANISM: Arabidopsis thaliana

<400> SEQUENCE: 1

Arg Arg Ala Ser Leu His Arg Phe Leu Glu Lys Arg Lys Asp Arg Val
1               5                   10                  15

Thr Ser Lys Ala Pro Tyr
            20

<210> SEQ ID NO 2
<211> LENGTH: 17
<212> TYPE: PRT
<213> ORGANISM: Arabidopsis thaliana

<400> SEQUENCE: 2

Ala Arg Arg Ala Ser Leu His Arg Phe Leu Glu Lys Arg Lys Asp Arg
1               5                   10                  15

Val

<210> SEQ ID NO 3
<211> LENGTH: 18
<212> TYPE: PRT
<213> ORGANISM: Arabidopsis thaliana

<400> SEQUENCE: 3

Ile Ala Arg Arg Ala Ser Leu His Arg Phe Leu Glu Lys Arg Lys Asp
1               5                   10                  15

Arg Val

<210> SEQ ID NO 4
<211> LENGTH: 19
<212> TYPE: PRT
<213> ORGANISM: Arabidopsis thaliana

<400> SEQUENCE: 4
```

-continued

```
Pro Ile Ala Arg Arg Ala Ser Leu His Arg Phe Leu Glu Lys Arg Lys
1               5                   10                  15

Asp Arg Val

<210> SEQ ID NO 5
<211> LENGTH: 20
<212> TYPE: PRT
<213> ORGANISM: Arabidopsis thaliana

<400> SEQUENCE: 5

Leu Pro Ile Ala Arg Arg Ala Ser Leu His Arg Phe Leu Glu Lys Arg
1               5                   10                  15

Lys Asp Arg Val
            20

<210> SEQ ID NO 6
<211> LENGTH: 21
<212> TYPE: PRT
<213> ORGANISM: Arabidopsis thaliana

<400> SEQUENCE: 6

Glu Leu Pro Ile Ala Arg Arg Ala Ser Leu His Arg Phe Leu Glu Lys
1               5                   10                  15

Arg Lys Asp Arg Val
            20

<210> SEQ ID NO 7
<211> LENGTH: 27
<212> TYPE: PRT
<213> ORGANISM: Arabidopsis thaliana

<400> SEQUENCE: 7

Glu Leu Pro Ile Ala Arg Arg Ala Ser Leu His Arg Phe Leu Glu Lys
1               5                   10                  15

Arg Lys Asp Arg Val Thr Ser Lys Ala Pro Tyr
            20                  25

<210> SEQ ID NO 8
<211> LENGTH: 21
<212> TYPE: PRT
<213> ORGANISM: Artificial
<220> FEATURE:
<223> OTHER INFORMATION: Arabidopsis jasmonate JAZ1 degron fragment with
      N-terminal polyA extension

<400> SEQUENCE: 8

Ala Ala Ala Ala Ala Arg Arg Ala Ser Leu His Arg Phe Leu Glu Lys
1               5                   10                  15

Arg Lys Asp Arg Val
            20

<210> SEQ ID NO 9
<211> LENGTH: 21
<212> TYPE: PRT
<213> ORGANISM: Artificial
<220> FEATURE:
<223> OTHER INFORMATION: Arabidopsis jasmonate JAZ1 degron fragment with
      N-terminal extension derived from JAZ6

<400> SEQUENCE: 9

Val Glu Arg Ile Ala Arg Arg Ala Ser Leu His Arg Phe Leu Glu Lys
1               5                   10                  15

Arg Lys Asp Arg Val
```

```
                    20

<210> SEQ ID NO 10
<211> LENGTH: 21
<212> TYPE: PRT
<213> ORGANISM: Arabidopsis thaliana

<400> SEQUENCE: 10

Val Glu Arg Ile Ala Arg Arg Ala Ser Leu His Arg Phe Phe Ala Lys
1               5                   10                  15

Arg Lys Asp Arg Val
            20

<210> SEQ ID NO 11
<211> LENGTH: 26
<212> TYPE: PRT
<213> ORGANISM: Arabidopsis thaliana

<400> SEQUENCE: 11

Gln Gln His Gln Val Val Glu Arg Ile Ala Arg Arg Ala Ser Leu His
1               5                   10                  15

Arg Phe Phe Ala Lys Arg Lys Asp Arg Val
            20                  25

<210> SEQ ID NO 12
<211> LENGTH: 21
<212> TYPE: PRT
<213> ORGANISM: Arabidopsis thaliana

<400> SEQUENCE: 12

Tyr Gln Lys Ala Ser Met Lys Arg Ser Leu His Ser Phe Leu Gln Lys
1               5                   10                  15

Arg Ser Leu Arg Ile
            20

<210> SEQ ID NO 13
<211> LENGTH: 27
<212> TYPE: PRT
<213> ORGANISM: Artificial
<220> FEATURE:
<223> OTHER INFORMATION: JAZ1-based peptide tag
<220> FEATURE:
<221> NAME/KEY: MISC_FEATURE
<222> LOCATION: (1)..(1)
<223> OTHER INFORMATION: Absent, Glu, or Val
<220> FEATURE:
<221> NAME/KEY: MISC_FEATURE
<222> LOCATION: (2)..(2)
<223> OTHER INFORMATION: Absent, Leu, or Glu
<220> FEATURE:
<221> NAME/KEY: MISC_FEATURE
<222> LOCATION: (3)..(3)
<223> OTHER INFORMATION: Absent, Pro, or Arg
<220> FEATURE:
<221> NAME/KEY: MISC_FEATURE
<222> LOCATION: (4)..(4)
<223> OTHER INFORMATION: Absent or Ile
<220> FEATURE:
<221> NAME/KEY: MISC_FEATURE
<222> LOCATION: (5)..(5)
<223> OTHER INFORMATION: Absent or Ala
<220> FEATURE:
<221> NAME/KEY: MISC_FEATURE
<222> LOCATION: (8)..(8)
<223> OTHER INFORMATION: Ala or Lys
<220> FEATURE:
<221> NAME/KEY: MISC_FEATURE
<222> LOCATION: (22)..(22)
<223> OTHER INFORMATION: Absent or Thr
```

-continued

```
<220> FEATURE:
<221> NAME/KEY: MISC_FEATURE
<222> LOCATION: (23)..(23)
<223> OTHER INFORMATION: Absent or Ser
<220> FEATURE:
<221> NAME/KEY: MISC_FEATURE
<222> LOCATION: (24)..(24)
<223> OTHER INFORMATION: Absent or Lys
<220> FEATURE:
<221> NAME/KEY: MISC_FEATURE
<222> LOCATION: (25)..(25)
<223> OTHER INFORMATION: Absent or Ala
<220> FEATURE:
<221> NAME/KEY: MISC_FEATURE
<222> LOCATION: (26)..(26)
<223> OTHER INFORMATION: Absent or Pro
<220> FEATURE:
<221> NAME/KEY: MISC_FEATURE
<222> LOCATION: (27)..(27)
<223> OTHER INFORMATION: Absent or Tyr

<400> SEQUENCE: 13

Xaa Xaa Xaa Xaa Xaa Arg Arg Xaa Ser Leu His Arg Phe Leu Glu Lys
1               5                   10                  15

Arg Lys Asp Arg Val Xaa Xaa Xaa Xaa Xaa
            20              25

<210> SEQ ID NO 14
<211> LENGTH: 253
<212> TYPE: PRT
<213> ORGANISM: Arabidopsis thaliana

<400> SEQUENCE: 14

Met Ser Ser Ser Met Glu Cys Ser Glu Phe Val Gly Ser Arg Arg Phe
1               5                   10                  15

Thr Gly Lys Lys Pro Ser Phe Ser Gln Thr Cys Ser Arg Leu Ser Gln
            20                  25                  30

Tyr Leu Lys Glu Asn Gly Ser Phe Gly Asp Leu Ser Leu Gly Met Ala
        35                  40                  45

Cys Lys Pro Asp Val Asn Gly Thr Leu Gly Asn Ser Arg Gln Pro Thr
    50                  55                  60

Thr Thr Met Ser Leu Phe Pro Cys Glu Ala Ser Asn Met Asp Ser Met
65                  70                  75                  80

Val Gln Asp Val Lys Pro Thr Asn Leu Phe Pro Arg Gln Pro Ser Phe
                85                  90                  95

Ser Ser Ser Ser Ser Ser Leu Pro Lys Glu Asp Val Leu Lys Met Thr
            100                 105                 110

Gln Thr Thr Arg Ser Val Lys Pro Glu Ser Gln Thr Ala Pro Leu Thr
        115                 120                 125

Ile Phe Tyr Ala Gly Gln Val Ile Val Phe Asn Asp Phe Ser Ala Glu
    130                 135                 140

Lys Ala Lys Glu Val Ile Asn Leu Ala Ser Lys Gly Thr Ala Asn Ser
145                 150                 155                 160

Leu Ala Lys Asn Gln Thr Asp Ile Arg Ser Asn Ile Ala Thr Ile Ala
                165                 170                 175

Asn Gln Val Pro His Pro Arg Lys Thr Thr Thr Gln Glu Pro Ile Gln
            180                 185                 190

Ser Ser Pro Thr Pro Leu Thr Glu Leu Pro Ile Ala Arg Arg Ala Ser
        195                 200                 205

Leu His Arg Phe Leu Glu Lys Arg Lys Asp Arg Val Thr Ser Lys Ala
    210                 215                 220
```

```
Pro Tyr Gln Leu Cys Asp Pro Ala Lys Ala Ser Ser Asn Pro Gln Thr
225                 230                 235                 240

Thr Gly Asn Met Ser Trp Leu Gly Leu Ala Ala Glu Ile
            245                 250
```

<210> SEQ ID NO 15
<211> LENGTH: 592
<212> TYPE: PRT
<213> ORGANISM: Arabidopsis thaliana

<400> SEQUENCE: 15

```
Met Glu Asp Pro Asp Ile Lys Arg Cys Lys Leu Ser Cys Val Ala Thr
1               5                   10                  15

Val Asp Asp Val Ile Glu Gln Val Met Thr Tyr Ile Thr Asp Pro Lys
            20                  25                  30

Asp Arg Asp Ser Ala Ser Leu Val Cys Arg Arg Trp Phe Lys Ile Asp
        35                  40                  45

Ser Glu Thr Arg Glu His Val Thr Met Ala Leu Cys Tyr Thr Ala Thr
    50                  55                  60

Pro Asp Arg Leu Ser Arg Arg Phe Pro Asn Leu Arg Ser Leu Lys Leu
65                  70                  75                  80

Lys Gly Lys Pro Arg Ala Ala Met Phe Asn Leu Ile Pro Glu Asn Trp
                85                  90                  95

Gly Gly Tyr Val Thr Pro Trp Val Thr Glu Ile Ser Asn Asn Leu Arg
            100                 105                 110

Gln Leu Lys Ser Val His Phe Arg Arg Met Ile Val Ser Asp Leu Asp
        115                 120                 125

Leu Asp Arg Leu Ala Lys Ala Arg Ala Asp Asp Leu Glu Thr Leu Lys
130                 135                 140

Leu Asp Lys Cys Ser Gly Phe Thr Thr Asp Gly Leu Leu Ser Ile Val
145                 150                 155                 160

Thr His Cys Arg Lys Ile Lys Thr Leu Leu Met Glu Glu Ser Ser Phe
                165                 170                 175

Ser Glu Lys Asp Gly Lys Trp Leu His Glu Leu Ala Gln His Asn Thr
            180                 185                 190

Ser Leu Glu Val Leu Asn Phe Tyr Met Thr Glu Phe Ala Lys Ile Ser
        195                 200                 205

Pro Lys Asp Leu Glu Thr Ile Ala Arg Asn Cys Arg Ser Leu Val Ser
210                 215                 220

Val Lys Val Gly Asp Phe Glu Ile Leu Glu Leu Val Gly Phe Phe Lys
225                 230                 235                 240

Ala Ala Ala Asn Leu Glu Glu Phe Cys Gly Gly Ser Leu Asn Glu Asp
                245                 250                 255

Ile Gly Met Pro Glu Lys Tyr Met Asn Leu Val Phe Pro Arg Lys Leu
            260                 265                 270

Cys Arg Leu Gly Leu Ser Tyr Met Gly Pro Asn Glu Met Pro Ile Leu
        275                 280                 285

Phe Pro Phe Ala Ala Gln Ile Arg Lys Leu Asp Leu Leu Tyr Ala Leu
290                 295                 300

Leu Glu Thr Glu Asp His Cys Thr Leu Ile Gln Lys Cys Pro Asn Leu
305                 310                 315                 320

Glu Val Leu Glu Thr Arg Asn Val Ile Gly Asp Arg Gly Leu Glu Val
                325                 330                 335

Leu Ala Gln Tyr Cys Lys Gln Leu Lys Arg Leu Arg Ile Glu Arg Gly
            340                 345                 350
```

```
Ala Asp Glu Gln Gly Met Glu Asp Glu Gly Leu Val Ser Gln Arg
        355                 360                 365

Gly Leu Ile Ala Leu Ala Gln Gly Cys Gln Glu Leu Glu Tyr Met Ala
    370                 375                 380

Val Tyr Val Ser Asp Ile Thr Asn Glu Ser Leu Glu Ser Ile Gly Thr
385                 390                 395                 400

Tyr Leu Lys Asn Leu Cys Asp Phe Arg Leu Val Leu Leu Asp Arg Glu
                405                 410                 415

Glu Arg Ile Thr Asp Leu Pro Leu Asp Asn Gly Val Arg Ser Leu Leu
            420                 425                 430

Ile Gly Cys Lys Lys Leu Arg Arg Phe Ala Phe Tyr Leu Arg Gln Gly
        435                 440                 445

Gly Leu Thr Asp Leu Gly Leu Ser Tyr Ile Gly Gln Tyr Ser Pro Asn
    450                 455                 460

Val Arg Trp Met Leu Leu Gly Tyr Val Gly Glu Ser Asp Glu Gly Leu
465                 470                 475                 480

Met Glu Phe Ser Arg Gly Cys Pro Asn Leu Gln Lys Leu Glu Met Arg
                485                 490                 495

Gly Cys Cys Phe Ser Glu Arg Ala Ile Ala Ala Val Thr Lys Leu
        500                 505                 510

Pro Ser Leu Arg Tyr Leu Trp Val Gln Gly Tyr Arg Ala Ser Met Thr
    515                 520                 525

Gly Gln Asp Leu Met Gln Met Ala Arg Pro Tyr Trp Asn Ile Glu Leu
    530                 535                 540

Ile Pro Ser Arg Arg Val Pro Glu Val Asn Gln Gly Glu Ile Arg
545                 550                 555                 560

Glu Met Glu His Pro Ala His Ile Leu Ala Tyr Tyr Ser Leu Ala Gly
                565                 570                 575

Gln Arg Thr Asp Cys Pro Thr Thr Val Arg Val Leu Lys Glu Pro Ile
            580                 585                 590

<210> SEQ ID NO 16
<211> LENGTH: 593
<212> TYPE: PRT
<213> ORGANISM: Arabidopsis lyrata

<400> SEQUENCE: 16

Met Glu Asp Pro Asp Ile Ile Lys Arg Cys Arg Leu Ser Cys Val Ala
1               5                   10                  15

Thr Val Asp Asp Val Ile Glu Gln Val Met Thr Tyr Ile Thr Asp Pro
            20                  25                  30

Lys Asp Arg Asp Ser Ala Ser Leu Val Cys Arg Arg Trp Phe Lys Ile
        35                  40                  45

Asp Ser Glu Thr Arg Glu His Val Thr Met Ala Leu Cys Tyr Thr Ala
    50                  55                  60

Thr Pro Asp Arg Leu Ser Arg Arg Phe Pro Asn Leu Arg Ser Leu Lys
65                  70                  75                  80

Leu Lys Gly Lys Pro Arg Ala Ala Met Phe Asn Leu Ile Pro Glu Asn
                85                  90                  95

Trp Gly Gly Tyr Val Thr Pro Trp Val Thr Glu Ile Ser Lys Ser Leu
            100                 105                 110

Lys Gln Leu Lys Ser Val His Phe Arg Arg Met Ile Val Ser Asp Leu
        115                 120                 125

Asp Leu Asp Arg Leu Ala Lys Ala Arg Ala Asp Asp Leu Glu Ala Leu
```

```
            130                 135                 140
Lys Leu Asp Lys Cys Ser Gly Phe Thr Thr Asp Gly Leu Leu Ser Ile
145                 150                 155                 160

Val Thr His Cys Arg Lys Ile Lys Thr Leu Leu Met Glu Glu Ser Ser
            165                 170                 175

Phe Ile Glu Lys Asp Gly Lys Trp Leu His Glu Leu Ala Gln His Asn
            180                 185                 190

Thr Ser Leu Glu Val Leu Asn Phe Tyr Met Thr Glu Phe Ala Lys Ile
            195                 200                 205

Ser Pro Lys Asp Leu Glu Thr Ile Ala Arg Asn Cys Arg Ser Leu Val
210                 215                 220

Ser Val Lys Val Gly Asp Cys Glu Ile Leu Glu Leu Val Gly Phe Phe
225                 230                 235                 240

Lys Ala Ala Ala Asn Leu Glu Glu Phe Cys Gly Gly Ser Leu Asn Glu
            245                 250                 255

Asp Ile Gly Met Pro Glu Lys Tyr Met Asn Leu Val Phe Pro Arg Lys
            260                 265                 270

Leu Cys Arg Leu Gly Leu Ser Tyr Met Gly Pro Asn Glu Met Pro Ile
            275                 280                 285

Leu Phe Pro Phe Ala Ala Gln Ile Arg Lys Leu Asp Leu Leu Tyr Ala
            290                 295                 300

Leu Leu Glu Thr Glu Asp His Cys Thr Leu Ile Gln Lys Cys Pro Asn
305                 310                 315                 320

Leu Glu Val Leu Glu Thr Arg Asn Val Ile Gly Asp Arg Gly Leu Glu
            325                 330                 335

Val Leu Ala Gln Tyr Cys Lys Gln Leu Lys Arg Leu Arg Ile Glu Arg
            340                 345                 350

Gly Ala Asp Glu Gln Gly Met Glu Asp Glu Gly Leu Val Ser Gln
            355                 360                 365

Arg Gly Leu Ile Ala Leu Ala Gln Gly Cys Gln Gln Leu Glu Tyr Met
            370                 375                 380

Ala Val Tyr Val Ser Asp Ile Thr Asn Glu Ser Leu Glu Ser Ile Gly
385                 390                 395                 400

Thr Tyr Leu Lys Asn Leu Cys Asp Phe Arg Leu Val Leu Leu Asp Arg
            405                 410                 415

Glu Glu Arg Ile Thr Asp Leu Pro Leu Asp Asn Gly Val Arg Ser Leu
            420                 425                 430

Leu Ile Gly Cys Lys Lys Leu Arg Arg Phe Ala Phe Tyr Leu Arg Gln
            435                 440                 445

Gly Gly Leu Thr Asp Leu Gly Leu Ser Tyr Ile Gly Gln Tyr Ser Pro
450                 455                 460

Asn Val Arg Trp Met Leu Leu Gly Tyr Val Gly Glu Ser Asp Glu Gly
465                 470                 475                 480

Leu Met Glu Phe Ser Arg Gly Cys Pro Asn Leu Gln Lys Leu Glu Met
            485                 490                 495

Arg Gly Cys Cys Phe Ser Glu Arg Ala Ile Ala Ala Val Thr Lys
            500                 505                 510

Leu Pro Ser Leu Arg Tyr Leu Trp Val Gln Gly Tyr Arg Ala Ser Met
            515                 520                 525

Thr Gly Gln Asp Leu Met Gln Met Ala Arg Pro Tyr Trp Asn Ile Glu
            530                 535                 540

Leu Ile Pro Ser Arg Lys Val Pro Glu Val Asn Gln Leu Gly Glu Ile
545                 550                 555                 560
```

```
Arg Glu Met Glu His Pro Ala His Ile Leu Ala Tyr Tyr Ser Leu Ala
            565                 570                 575
Gly Gln Arg Thr Asp Cys Pro Thr Thr Val Ile Val Leu Arg Glu Pro
            580                 585                 590
Met

<210> SEQ ID NO 17
<211> LENGTH: 595
<212> TYPE: PRT
<213> ORGANISM: Oryza sativa

<400> SEQUENCE: 17

Met Gly Gly Glu Val Pro Glu Pro Arg Arg Leu Asn Arg Ala Leu Ser
1               5                   10                  15
Phe Asp Asp Trp Val Pro Asp Glu Ala Leu His Leu Val Met Gly His
                20                  25                  30
Val Glu Asp Pro Arg Asp Arg Glu Ala Ala Ser Arg Val Cys Arg Arg
            35                  40                  45
Trp His Arg Ile Asp Ala Leu Thr Arg Lys His Val Thr Val Ala Phe
        50                  55                  60
Cys Tyr Ala Ala Arg Pro Ala Arg Leu Arg Glu Arg Phe Pro Arg Leu
65                  70                  75                  80
Glu Ser Leu Ser Leu Lys Gly Lys Pro Arg Ala Ala Met Tyr Gly Leu
                85                  90                  95
Ile Pro Asp Asp Trp Gly Ala Tyr Ala Ala Pro Trp Ile Asp Glu Leu
            100                 105                 110
Ala Ala Pro Leu Glu Cys Leu Lys Ala Leu His Leu Arg Arg Met Thr
        115                 120                 125
Val Thr Asp Ala Asp Ile Ala Ala Leu Val Arg Ala Arg Gly His Met
    130                 135                 140
Leu Gln Glu Leu Lys Leu Asp Lys Cys Ile Gly Phe Ser Thr Asp Ala
145                 150                 155                 160
Leu Arg Leu Val Ala Arg Ser Cys Arg Ser Leu Arg Thr Leu Phe Leu
                165                 170                 175
Glu Glu Cys His Ile Thr Asp Lys Gly Gly Glu Trp Leu His Glu Leu
            180                 185                 190
Ala Val Asn Asn Ser Val Leu Val Thr Leu Asn Phe Tyr Met Thr Glu
        195                 200                 205
Leu Lys Val Ala Pro Ala Asp Leu Glu Leu Leu Ala Lys Asn Cys Lys
    210                 215                 220
Ser Leu Ile Ser Leu Lys Met Ser Glu Cys Asp Leu Ser Asp Leu Ile
225                 230                 235                 240
Ser Phe Phe Gln Thr Ala Asn Ala Leu Gln Asp Phe Ala Gly Gly Ala
                245                 250                 255
Phe Tyr Glu Val Gly Glu Leu Thr Lys Tyr Glu Lys Val Lys Phe Pro
            260                 265                 270
Pro Arg Leu Cys Phe Leu Gly Leu Thr Tyr Met Gly Thr Asn Glu Met
        275                 280                 285
Pro Val Ile Phe Pro Phe Ser Met Lys Leu Lys Leu Asp Leu Gln
    290                 295                 300
Tyr Thr Phe Leu Thr Thr Glu Asp His Cys Gln Ile Ala Lys Cys
305                 310                 315                 320
Pro Asn Leu Leu Ile Leu Glu Val Arg Asn Val Ile Gly Asp Arg Gly
                325                 330                 335
```

```
Leu Glu Val Val Gly Asp Thr Cys Lys Lys Leu Arg Arg Leu Arg Ile
            340                 345                 350

Glu Arg Gly Asp Asp Pro Gly Leu Gln Glu Gln Gly Gly Val
            355                 360             365

Ser Gln Leu Gly Leu Thr Ala Val Ala Val Gly Cys Arg Glu Leu Glu
            370                 375                 380

Tyr Ile Ala Ala Tyr Val Ser Asp Ile Thr Asn Gly Ala Leu Glu Ser
385                 390                 395                 400

Ile Gly Thr Phe Cys Lys Asn Leu Tyr Asp Phe Arg Leu Val Leu Leu
                405                 410                 415

Asp Arg Glu Arg Gln Val Thr Asp Leu Pro Leu Asp Asn Gly Val Cys
            420                 425                 430

Ala Leu Leu Arg Asn Cys Thr Lys Leu Arg Arg Phe Ala Leu Tyr Leu
            435                 440                 445

Arg Pro Gly Gly Leu Ser Asp Asp Gly Leu Ser Tyr Ile Gly Gln Tyr
            450                 455                 460

Ser Gly Asn Ile Gln Tyr Met Leu Leu Gly Asn Val Gly Glu Ser Asp
465                 470                 475                 480

His Gly Leu Ile Arg Phe Ala Val Gly Cys Thr Asn Leu Gln Lys Leu
                485                 490                 495

Glu Leu Arg Ser Cys Cys Phe Ser Glu Arg Ala Leu Ser Leu Ala Val
            500                 505                 510

Leu Gln Met Pro Ser Leu Arg Tyr Ile Trp Val Gln Gly Tyr Arg Ala
            515                 520                 525

Ser Gln Thr Gly Leu Asp Leu Leu Met Ala Arg Pro Phe Trp Asn
            530                 535                 540

Ile Glu Phe Thr Pro Pro Ser Pro Glu Ser Phe Asn His Met Thr Glu
545                 550                 555                 560

Asp Gly Glu Pro Cys Val Asp Ser His Ala Gln Val Leu Ala Tyr Tyr
                565                 570                 575

Ser Leu Ala Gly Arg Arg Ser Asp Cys Pro Gln Trp Val Ile Pro Leu
            580                 585                 590

His Pro Ala
        595

<210> SEQ ID NO 18
<211> LENGTH: 603
<212> TYPE: PRT
<213> ORGANISM: Solanum lycopersicum

<400> SEQUENCE: 18

Met Glu Glu Arg Asn Ser Thr Arg Leu Ser Ser Ser Thr Asn Asp Thr
1               5                   10                  15

Val Trp Glu Cys Val Ile Pro Tyr Ile Gln Glu Ser Arg Asp Arg Asp
                20                  25                  30

Ala Val Ser Leu Val Cys Lys Arg Trp Gln Ile Asp Ala Ile Thr
            35                  40                  45

Arg Lys His Ile Thr Met Ala Leu Cys Tyr Thr Ala Lys Pro Glu Gln
50                  55                  60

Leu Ser Arg Arg Phe Pro His Leu Glu Ser Val Lys Leu Lys Gly Lys
65                  70                  75                  80

Pro Arg Ala Ala Met Phe Asn Leu Ile Pro Glu Asp Trp Gly Gly Tyr
                85                  90                  95

Val Thr Pro Trp Val Met Glu Ile Thr Lys Ser Phe Ser Lys Leu Lys
```

```
                100             105             110
Ala Leu His Phe Arg Arg Met Ile Val Arg Asp Ser Asp Leu Glu Leu
            115             120             125

Leu Ala Asn Arg Arg Gly Arg Val Leu Gln Val Leu Lys Leu Asp Lys
            130             135             140

Cys Ser Gly Phe Ser Thr Asp Gly Leu Leu His Ile Ser Arg Ser Cys
145             150             155             160

Lys Asn Leu Arg Thr Leu Leu Met Glu Glu Ser Tyr Ile Ile Glu Lys
            165             170             175

Asp Gly Glu Trp Ala His Glu Leu Ala Leu Asn Asn Thr Val Leu Glu
            180             185             190

Asn Leu Asn Phe Tyr Met Thr Asp Leu Leu Gln Val Arg Ala Glu Asp
            195             200             205

Leu Glu Leu Ile Ala Arg Asn Cys Lys Ser Leu Val Ser Met Lys Ile
            210             215             220

Ser Glu Cys Glu Ile Thr Asn Leu Leu Gly Phe Phe Arg Ala Ala Ala
225             230             235             240

Ala Leu Glu Glu Phe Gly Gly Ala Phe Asn Asp Gln Pro Glu Leu
            245             250             255

Val Val Glu Asn Gly Tyr Asn Glu His Ser Gly Lys Tyr Ala Ala Leu
            260             265             270

Val Phe Pro Pro Arg Leu Cys Gln Leu Gly Leu Thr Tyr Leu Gly Arg
            275             280             285

Asn Glu Met Ser Ile Leu Phe Pro Ile Ala Ser Arg Leu Arg Lys Leu
            290             295             300

Asp Leu Leu Tyr Ala Leu Leu Asp Thr Ala Ala His Cys Phe Leu Leu
305             310             315             320

Gln Arg Cys Pro Asn Leu Glu Ile Leu Glu Thr Arg Asn Val Val Gly
            325             330             335

Asp Arg Gly Leu Glu Val Leu Gly Gln Tyr Cys Lys Arg Leu Lys Arg
            340             345             350

Leu Arg Ile Glu Arg Gly Ala Asp Asp Gln Glu Met Glu Asp Glu Glu
            355             360             365

Gly Ala Val Thr His Arg Gly Leu Ile Asp Leu Ala Lys Gly Cys Leu
            370             375             380

Glu Leu Glu Tyr Met Ala Val Tyr Val Ser Asp Ile Thr Asn Glu Ala
385             390             395             400

Leu Glu Val Ile Gly Thr Tyr Leu Lys Asn Leu Ser Asp Phe Arg Leu
            405             410             415

Val Leu Leu Asp Arg Glu Glu Arg Ile Thr Asp Leu Pro Leu Asp Asn
            420             425             430

Gly Val Arg Ala Leu Leu Arg Gly Cys His Asn Leu Arg Arg Phe Ala
            435             440             445

Leu Tyr Val Arg Pro Gly Gly Leu Thr Asp Val Gly Leu Ser Tyr Val
            450             455             460

Gly Gln Tyr Ser Pro Asn Val Arg Trp Met Leu Leu Gly Tyr Val Gly
465             470             475             480

Glu Ser Asp His Gly Leu Leu Glu Phe Ser Lys Gly Cys Pro Ser Leu
            485             490             495

Gln Lys Leu Glu Val Arg Gly Cys Cys Phe Ser Glu Arg Ala Leu Ala
            500             505             510

Leu Ala Thr Leu Gln Leu Lys Ser Leu Arg Tyr Leu Trp Val Gln Gly
            515             520             525
```

```
Tyr Arg Ala Ser Ser Ala Gly Arg Asp Leu Leu Ala Met Ala Arg Pro
            530                 535                 540

Phe Trp Asn Ile Glu Leu Ile Pro Ala Arg Arg Val Ile Ala Asn Asp
545                 550                 555                 560

Gly Asn Asn Ala Glu Thr Val Val Ser Glu His Pro Ala His Ile Leu
                565                 570                 575

Ala Tyr Tyr Ser Leu Ala Gly Gln Arg Thr Asp Phe Pro Asp Thr Val
            580                 585                 590

Lys Pro Leu Asp Pro Thr Tyr Leu Leu Ala Glu
            595                 600

<210> SEQ ID NO 19
<211> LENGTH: 598
<212> TYPE: PRT
<213> ORGANISM: Vitis vinifera

<400> SEQUENCE: 19

Met Glu Asp Gly Asn Glu Arg Lys Val Ser Arg Glu Met Leu Asp Met
1               5                   10                  15

Ala Asp Arg Gly Met Ser Asp Glu Val Leu Asn Cys Val Met Pro Tyr
            20                  25                  30

Ile His Asp Pro Lys Asp Arg Asp Ala Val Ser Leu Val Cys Arg Arg
        35                  40                  45

Trp Tyr Glu Leu Asp Ala Leu Thr Arg Lys His Ile Thr Ile Ala Leu
    50                  55                  60

Cys Tyr Thr Thr Thr Pro Gly Arg Leu Arg Gly Arg Phe Pro His Leu
65                  70                  75                  80

Glu Ser Leu Lys Leu Lys Gly Lys Pro Arg Ala Ala Met Phe Asn Leu
                85                  90                  95

Ile Met Glu Asp Trp Gly Gly Tyr Val Thr Pro Trp Val Lys Glu Ile
            100                 105                 110

Ser Asp Tyr Phe Asp Cys Leu Lys Ser Leu His Phe Arg Arg Met Ile
        115                 120                 125

Val Lys Asp Ser Asp Leu Gln Leu Leu Ala Gln Ala Arg Gly Arg Val
    130                 135                 140

Leu Leu Val Leu Lys Leu Asp Lys Cys Ser Gly Phe Ser Thr Asp Gly
145                 150                 155                 160

Leu Leu His Val Gly Arg Ser Cys Arg Asn Leu Arg Thr Leu Phe Leu
                165                 170                 175

Glu Glu Ser Gln Ile Val Asp Lys Asp Gly Glu Trp Leu His Glu Leu
            180                 185                 190

Ala Met Asn Asn Thr Val Leu Glu Thr Leu Asn Phe Tyr Met Thr Glu
        195                 200                 205

Leu Ala Thr Val Gln Phe Glu Asp Leu Glu Leu Ile Ala Arg Asn Cys
    210                 215                 220

Arg Ser Leu Thr Ser Met Lys Ile Ser Asp Phe Glu Ile Leu Asp Leu
225                 230                 235                 240

Val Gly Phe Phe Arg Ala Ala Thr Ala Leu Glu Glu Phe Ala Gly Gly
                245                 250                 255

Ser Phe Ser Glu Gln Ser Asp Lys Tyr Ser Ala Val Ser Phe Pro Pro
            260                 265                 270

Lys Leu Cys Arg Leu Gly Leu Asn Tyr Met Gly Lys Asn Glu Met Pro
        275                 280                 285

Ile Val Phe Pro Phe Ala Ser Leu Leu Lys Lys Leu Asp Leu Leu Tyr
```

Cys Leu Leu Asp Thr Glu Asp His Cys Leu Leu Ile Gln Lys Cys Pro
305                 310                 315                 320

Asn Leu Glu Phe Leu Glu Ala Arg Asn Val Ile Gly Asp Arg Gly Leu
            325                 330                 335

Glu Val Leu Ala Gln Ser Cys Lys Lys Leu Arg Arg Leu Arg Ile Glu
        340                 345                 350

Arg Gly Ala Asp Glu Gln Glu Met Glu Asp Glu Glu Gly Val Val Ser
    355                 360                 365

Gln Arg Gly Leu Met Ala Leu Ala Arg Gly Cys Leu Glu Ile Glu Tyr
370                 375                 380

Val Ala Ile Tyr Val Ser Asp Ile Thr Asn Ala Ala Leu Glu Cys Ile
385                 390                 395                 400

Gly Ala His Ser Lys Lys Leu Cys Asp Phe Arg Leu Val Leu Leu Glu
            405                 410                 415

Arg Glu Glu Arg Ile Thr Asp Leu Pro Leu Asp Asn Gly Val Arg Ala
        420                 425                 430

Leu Leu Arg Gly Cys Gln Lys Leu Arg Arg Phe Ala Leu Tyr Leu Arg
    435                 440                 445

Ser Gly Gly Leu Thr Asp Val Gly Leu Asn Tyr Ile Gly Gln Tyr Ser
450                 455                 460

Pro Asn Val Arg Trp Met Leu Leu Gly Tyr Val Gly Glu Ser Asp Ala
465                 470                 475                 480

Gly Leu Leu Glu Phe Ser Arg Gly Cys Pro Ser Leu Gln Lys Leu Glu
            485                 490                 495

Met Arg Gly Cys Cys Phe Ser Glu Arg Ala Leu Ala Val Ala Ala Met
        500                 505                 510

Gln Leu Thr Ser Leu Arg Tyr Leu Trp Val Gln Gly Tyr Arg Ala Ser
    515                 520                 525

Glu Thr Gly Arg Asp Leu Leu Val Met Ala Arg Pro Phe Trp Asn Ile
530                 535                 540

Glu Leu Ile Pro Ser Arg Gly Val Thr Ile Asn Ala Pro Asp Arg Glu
545                 550                 555                 560

Pro Val Ser Ile Glu His Pro Ala His Ile Leu Ala Tyr Tyr Ser Leu
            565                 570                 575

Ala Gly Pro Arg Thr Asp Phe Pro Ser Thr Val Thr Pro Leu Asp Pro
        580                 585                 590

Ala Ser Phe Leu Thr Leu
        595

<210> SEQ ID NO 20
<211> LENGTH: 573
<212> TYPE: PRT
<213> ORGANISM: Populus trichocarpa

<400> SEQUENCE: 20

Met Pro Tyr Ile Asn Asp Pro Arg Asp Arg Asp Ala Val Ser Leu Val
1               5                   10                  15

Cys Arg Arg Trp Tyr Glu Leu Asp Ala Leu Thr Arg Lys Asn Val Thr
            20                  25                  30

Ile Ala Phe Cys Tyr Ser Thr Ser Pro Asp Arg Leu Arg Arg Arg Phe
        35                  40                  45

Asn Asp Ile Glu Ser Leu Lys Leu Lys Gly Lys Pro Arg Ala Ala Met
    50                  55                  60

```
Phe Phe Asn Leu Ile Pro Glu Asp Trp Gly Gly Phe Val Thr Pro Trp
 65                  70                  75                  80

Val Asn Glu Ile Ala Glu Ser Phe Asn Cys Leu Lys Ser Leu His Phe
                 85                  90                  95

Arg Arg Met Ile Val Lys Asp Ser Asp Leu Glu Leu Leu Ala Arg Ser
                100                 105                 110

Arg Gly Arg Leu Leu Gln Val Leu Lys Leu Asp Lys Cys Ser Gly Phe
            115                 120                 125

Ser Thr Asp Gly Leu Ser His Ile Gly Arg Ser Cys Arg Gln Leu Arg
130                 135                 140

Thr Leu Phe Leu Glu Glu Ser Ala Ile Val Glu Arg Asp Gly Asp Trp
145                 150                 155                 160

Leu His Glu Leu Ala Thr Asn Asn Thr Val Leu Glu Thr Leu Asn Phe
                165                 170                 175

Tyr Met Thr Glu Leu Thr Arg Val Arg Ser Glu Asp Leu Glu Leu Leu
                180                 185                 190

Ala Arg Asn Cys Arg Ser Leu Val Ser Val Lys Val Ser Asp Cys Glu
            195                 200                 205

Ile Leu Asp Leu Val Gly Phe Phe His Ala Ala Ser Ala Leu Glu Glu
210                 215                 220

Phe Cys Gly Gly Ser Phe Asn Glu Pro Asp Glu Pro Asp Lys Tyr Ser
225                 230                 235                 240

Ala Val Lys Phe Pro Pro Lys Leu Cys Cys Leu Gly Leu Ser Tyr Met
                245                 250                 255

Glu Lys Asn Val Met Ser Ile Val Phe Pro Phe Ala Ser Leu Leu Lys
            260                 265                 270

Lys Leu Asp Leu Leu Tyr Ala Phe Leu Gly Thr Glu Asp His Cys Val
            275                 280                 285

Leu Val Gln Arg Cys Pro Asn Leu Glu Val Leu Glu Thr Arg Asn Val
            290                 295                 300

Ile Gly Asp Arg Gly Leu Glu Ala Leu Ala Gln Ser Cys Lys Leu Leu
305                 310                 315                 320

Lys Arg Leu Arg Ile Glu Arg Gly Ala Asp Glu Gln Gly Met Glu Asp
                325                 330                 335

Val Asp Gly Arg Val Ser His Arg Gly Leu Ile Ala Leu Ala Gln Gly
                340                 345                 350

Cys Leu Glu Leu Glu Tyr Ile Ala Val Tyr Val Ser Asp Ile Thr Asn
            355                 360                 365

Ala Ala Leu Glu His Met Gly Thr Tyr Ser Lys Asn Leu Asn Asp Phe
370                 375                 380

Arg Leu Val Leu Leu Glu Gln Glu Arg Ile Thr Asp Leu Pro Leu
385                 390                 395                 400

Asp Asn Gly Val Arg Ala Leu Leu Arg Gly Cys Glu Lys Leu Gln Arg
                405                 410                 415

Phe Gly Leu Tyr Leu Arg Pro Gly Gly Leu Thr Asp Val Gly Leu Gly
            420                 425                 430

Tyr Ile Gly Gln Tyr Ser Arg Arg Val Arg Trp Met Ile Leu Gly Ser
            435                 440                 445

Val Gly Glu Ser Asp Glu Gly Leu Leu Ala Phe Ser Arg Gly Cys Pro
            450                 455                 460

Ser Leu Gln Lys Leu Glu Met Arg Ala Cys Cys Phe Ser Glu Ser Ala
465                 470                 475                 480

Leu Ala Arg Ala Ala Leu Gln Leu Thr Ser Leu Arg Tyr Leu Trp Val
```

```
                485                 490                 495
His Gly Tyr Arg Glu Thr Ser Thr Gly His Arg Asp Leu Leu Thr Met
                500                 505                 510

Val Arg Pro Phe Trp Asn Ile Glu Leu Ile Pro Ser Arg Lys Val Glu
                515                 520                 525

Ser Val Asn Glu Ala Gly Glu Asn Ile Val Ser Glu Asn Pro Ala His
                530                 535                 540

Ile Leu Ala Tyr Tyr Ser Leu Ala Gly Pro Arg Thr Asp Phe Pro Asp
545                 550                 555                 560

Thr Val Arg Pro Leu Asp Pro Ala Asn Ile Val Ala Ala
                565                 570

<210> SEQ ID NO 21
<211> LENGTH: 574
<212> TYPE: PRT
<213> ORGANISM: Populus trichocarpa

<400> SEQUENCE: 21

Met Pro Tyr Ile His Asp Pro Arg Asp Arg Asp Ala Val Ser Leu Val
1               5                   10                  15

Cys Arg Arg Trp Tyr Glu Leu Asp Ala Leu Thr Arg Lys His Val Thr
                20                  25                  30

Ile Ala Leu Cys Tyr Ser Thr Ser Pro Asp Arg Leu Gln Arg Arg Phe
            35                  40                  45

Lys His Leu Glu Ser Leu Lys Met Lys Gly Lys Pro Arg Ala Ala Met
        50                  55                  60

Phe Asn Leu Ile Pro Asp Asp Trp Gly Phe Val Thr Pro Trp
65                  70                  75                  80

Val Asn Glu Ile Ala Glu Ser Phe Asn Cys Leu Lys Ser Leu His Phe
                85                  90                  95

Arg Arg Met Ile Val Lys Asp Ser Asp Leu Glu Leu Leu Ala Ser Ser
                100                 105                 110

Arg Gly Lys Val Leu Gln Val Leu Lys Leu Asp Lys Cys Ser Gly Phe
            115                 120                 125

Ser Thr Asp Gly Leu Ser His Ile Gly Arg Ser Cys Arg Gln Leu Arg
        130                 135                 140

Thr Leu Phe Leu Glu Glu Ser Ala Ile Ala Tyr Glu Lys Asp Gly Asp
145                 150                 155                 160

Trp Leu His Glu Leu Ala Thr Asn Asn Thr Val Leu Glu Thr Leu Asn
                165                 170                 175

Phe Tyr Met Thr Asp Leu Thr Lys Val Arg Leu Glu Asp Leu Glu Leu
                180                 185                 190

Leu Ala Lys Asn Cys Arg Ser Leu Val Ser Val Lys Ile Ser Asp Cys
            195                 200                 205

Glu Ile Leu Glu Leu Val Gly Phe Phe Arg Ala Ala Ser Ala Ile Glu
        210                 215                 220

Glu Phe Cys Gly Gly Ser Phe Asn Glu Pro Asp Gln Pro Gly Lys Tyr
225                 230                 235                 240

Ser Ala Val Val Phe Pro Pro Lys Leu Cys Arg Leu Gly Leu Ser Tyr
                245                 250                 255

Met Glu Lys Asn Val Met Ser Ile Val Phe Pro Phe Ala Ser Leu Leu
                260                 265                 270

Lys Lys Leu Asp Leu Leu Tyr Val Leu Leu Gly Thr Glu Asp His Cys
            275                 280                 285
```

```
Val Leu Val Gln Arg Cys Pro Asn Leu Glu Val Leu Glu Thr Arg Asn
        290                 295                 300

Val Ile Gly Asp Arg Gly Leu Glu Ala Leu Ala Arg Ser Cys Lys Arg
305                 310                 315                 320

Leu Lys Arg Leu Arg Ile Glu Arg Gly Ala Asp Glu Gln Met Glu
                325                 330                 335

Asp Val Asp Gly Arg Val Ser Gln Arg Gly Leu Ile Ala Leu Ala Gln
                340                 345                 350

Gly Cys Leu Glu Leu Glu Tyr Ile Ala Val Tyr Val Ser Asp Ile Ser
            355                 360                 365

Asn Ala Ala Leu Glu His Met Gly Ala Tyr Ser Lys Asn Leu Asn Asp
    370                 375                 380

Phe Arg Leu Val Leu Leu Glu Gln Glu Asp Arg Ile Thr Asp Leu Pro
385                 390                 395                 400

Leu Asp Asn Gly Val Arg Ala Leu Leu Arg Gly Cys Glu Lys Leu Gln
                405                 410                 415

Arg Phe Gly Leu Tyr Leu Arg Ser Gly Gly Leu Thr Asp Val Gly Leu
            420                 425                 430

Gly Tyr Ile Gly Gln Tyr Ser Arg His Val Arg Trp Met Ile Leu Gly
            435                 440                 445

Ser Val Gly Glu Ser Asp Glu Gly Leu Leu Ala Phe Ser Met Gly Cys
    450                 455                 460

Pro Ser Leu Gln Lys Leu Glu Met Arg Ala Cys Cys Phe Thr Glu Arg
465                 470                 475                 480

Ala Leu Ala Arg Ala Ala Leu Gln Leu Thr Ser Leu Arg Tyr Leu Trp
                485                 490                 495

Val His Gly Tyr Arg Glu Thr Ser Asn Gly His Arg Asp Leu Leu Thr
            500                 505                 510

Met Val Arg Pro Phe Trp Asn Ile Glu Leu Ile Pro Ser Arg Arg Val
            515                 520                 525

Ala Thr Val Asn Asn Ala Gly Glu Asp Ile Val Ser Glu Asn Pro Ala
    530                 535                 540

His Ile Leu Ala Tyr Tyr Ser Leu Ala Gly Pro Arg Thr Asp Phe Pro
545                 550                 555                 560

Asp Thr Val Ile Pro Leu Asp Pro Ala Arg Val Val Ala Ala
                565                 570

<210> SEQ ID NO 22
<211> LENGTH: 602
<212> TYPE: PRT
<213> ORGANISM: Ricinus communis

<400> SEQUENCE: 22

Met Glu Glu Glu Asn Asn Lys Asn Ser Lys Leu Asn Lys Thr Met Ser
1               5                   10                  15

Ser Gly Ser Cys Ser Asn Gly Ser Asp Val Leu Asp Tyr Val Met Pro
                20                  25                  30

Tyr Ile Gln Gly Pro Lys Asp Arg Asp Ala Val Ser Leu Val Cys Arg
            35                  40                  45

Arg Trp Tyr Glu Leu Asp Ala Leu Thr Arg Lys His Ile Thr Ile Ala
        50                  55                  60

Leu Cys Tyr Thr Thr Ser Pro Asp Arg Leu Arg Arg Phe Lys His
65                  70                  75                  80

Leu Glu Ser Leu Lys Leu Lys Gly Lys Pro Arg Ala Ala Met Phe Asn
                85                  90                  95
```

```
Leu Ile Pro Glu Asp Trp Gly Gly Tyr Val Thr Pro Trp Ile Asp Glu
            100                 105                 110

Ile Ala Ala Ala Ser Phe Thr Cys Leu Lys Ser Leu His Phe Lys Arg
            115                 120                 125

Met Ile Val Lys Asp Ser Asp Leu Ala Leu Leu Ala Lys Ser Arg Gly
130                 135                 140

Lys Val Leu His Val Leu Lys Leu Asp Lys Cys Ser Gly Phe Ser Thr
145                 150                 155                 160

Asp Gly Leu Leu His Val Ala Cys Phe Cys Arg Gln Leu Arg Thr Leu
                165                 170                 175

Phe Leu Glu Glu Ser Ala Ile Phe Glu Lys Asp Gly Asp Trp Leu His
            180                 185                 190

Glu Ile Ala Met Asn Asn Thr Val Leu Glu Ile Leu Asn Phe Tyr Met
            195                 200                 205

Thr Asp Leu Asn Ala Val Arg Phe Glu Asp Leu Glu Ile Ile Ala Lys
210                 215                 220

Asn Cys Arg Cys Leu Val Ser Val Lys Ile Ser Asp Cys Glu Ile Leu
225                 230                 235                 240

Asp Leu Ala Gly Phe Phe His Ala Ala Ala Leu Glu Glu Phe Cys
            245                 250                 255

Gly Gly Ser Phe Asn Tyr Ser Ala Asn Asp Leu Gln Asp Lys Tyr Ser
            260                 265                 270

Ala Val Thr Phe Pro Arg Lys Leu Cys Arg Leu Gly Leu Thr Tyr Leu
            275                 280                 285

Gly Lys Asn Glu Met Pro Ile Val Phe Pro Phe Ala Ser Leu Leu Lys
            290                 295                 300

Lys Leu Asp Leu Leu Tyr Ala Leu Leu Asp Thr Glu Asp His Cys Leu
305                 310                 315                 320

Leu Ile Gln Lys Phe Cys Asn Leu Glu Val Leu Glu Thr Arg Asn Val
            325                 330                 335

Ile Gly Asp Arg Gly Leu Glu Val Leu Ala Ser Ser Cys Lys Arg Leu
            340                 345                 350

Lys Arg Leu Arg Ile Glu Arg Gly Ala Asp Glu Gln Gly Met Glu Asp
            355                 360                 365

Glu Glu Gly Ile Val Ser His Arg Gly Leu Ile Ala Leu Ala Gln Gly
370                 375                 380

Cys Leu Glu Leu Glu Tyr Leu Ala Val Tyr Val Ser Asp Ile Thr Asn
385                 390                 395                 400

Ala Ala Leu Glu His Ile Gly Ala His Leu Lys Asn Leu Asn Asp Phe
            405                 410                 415

Arg Leu Val Leu Leu Asp Lys Glu Glu Arg Ile Thr Asp Leu Pro Leu
            420                 425                 430

Asp Asn Gly Val Arg Ser Leu Leu Arg Gln Cys Glu Lys Leu Arg Arg
            435                 440                 445

Phe Ala Leu Tyr Leu Arg Pro Gly Gly Leu Thr Asp Val Gly Leu Gly
            450                 455                 460

Tyr Ile Gly Glu Tyr Ser Pro Asn Val Arg Trp Met Leu Leu Gly Tyr
465                 470                 475                 480

Val Gly Glu Ser Asp Glu Gly Leu Leu Ala Phe Ser Lys Gly Cys Pro
                485                 490                 495

Ser Leu Gln Lys Leu Glu Met Arg Gly Cys Cys Phe Thr Glu Arg Ala
            500                 505                 510
```

-continued

```
Leu Ala Arg Ala Val Met Gln Leu Thr Ser Leu Arg Tyr Leu Trp Val
            515                 520                 525

Gln Gly Tyr Arg Ala Ser Ser Val Pro Gly Arg Glu Leu Leu Ala Met
        530                 535                 540

Ala Arg Pro Phe Trp Asn Ile Glu Leu Ile Pro Pro Arg Arg Val Val
545                 550                 555                 560

Val Val Asn Gln Val Asn Glu Asp Val Leu Val Glu Gln Pro Ala His
                565                 570                 575

Ile Leu Ala Tyr Tyr Ser Leu Ala Gly Ala Arg Thr Asp Phe Pro Asp
            580                 585                 590

Ser Val Val Pro Leu His Pro Lys Arg Gly
            595                 600
```

<210> SEQ ID NO 23
<211> LENGTH: 599
<212> TYPE: PRT
<213> ORGANISM: Zea mays

<400> SEQUENCE: 23

```
Met Gly Gly Glu Ala Pro Glu Pro Arg Arg Leu Thr Arg Ala Leu Ser
1               5                   10                  15

Ile Gly Gly Gly Asp Gly Gly Trp Val Pro Glu Met Leu Gln Leu
            20                  25                  30

Val Met Gly Phe Val Glu Asp Pro Arg Asp Arg Glu Ala Ala Ser Leu
        35                  40                  45

Val Cys His Arg Trp His Arg Val Asp Ala Leu Ser Arg Lys His Val
    50                  55                  60

Thr Val Pro Phe Cys Tyr Ala Val Ser Pro Ala Arg Leu Leu Ala Arg
65                  70                  75                  80

Phe Pro Arg Leu Glu Ser Leu Ala Val Lys Gly Lys Pro Arg Ala Ala
                85                  90                  95

Met Tyr Gly Leu Ile Pro Asp Asp Trp Gly Ala Tyr Ala Arg Pro Trp
            100                 105                 110

Ile Thr Glu Leu Ala Ala Pro Leu Glu Cys Leu Lys Ala Leu His Leu
        115                 120                 125

Arg Arg Met Val Val Thr Asp Asp Leu Ala Glu Leu Val Arg Ala
    130                 135                 140

Arg Gly His Met Leu Gln Glu Leu Lys Leu Asp Lys Cys Thr Gly Phe
145                 150                 155                 160

Ser Thr His Gly Leu Arg Leu Val Ala Arg Ser Cys Arg Ser Leu Arg
                165                 170                 175

Thr Leu Phe Leu Glu Glu Cys Gln Ile Asp Asp Lys Gly Ser Glu Trp
            180                 185                 190

Ile His Asp Leu Ala Val Cys Cys Pro Val Leu Thr Thr Leu Asn Phe
        195                 200                 205

His Met Thr Glu Leu Glu Val Met Pro Ala Asp Leu Lys Leu Leu Ala
    210                 215                 220

Lys Ser Cys Lys Ser Leu Ile Ser Leu Lys Ile Ser Asp Cys Asp Leu
225                 230                 235                 240

Ser Asp Leu Ile Glu Phe Phe Gln Phe Ala Thr Ala Leu Glu Glu Phe
                245                 250                 255

Ala Gly Gly Thr Phe Asn Glu Gln Gly Glu Leu Ser Lys Tyr Val Asn
            260                 265                 270

Val Lys Phe Pro Ser Arg Leu Cys Ser Leu Gly Leu Thr Tyr Met Gly
        275                 280                 285
```

```
Thr Asn Glu Met Pro Ile Met Phe Pro Phe Ser Ala Ile Leu Lys Lys
    290                 295                 300

Leu Asp Leu Gln Tyr Thr Phe Leu Thr Thr Glu Asp His Cys Gln Leu
305                 310                 315                 320

Ile Ala Lys Cys Pro Asn Leu Leu Val Leu Ala Val Arg Asn Val Ile
                325                 330                 335

Gly Asp Arg Gly Leu Gly Val Val Ala Asp Thr Cys Lys Lys Leu Gln
            340                 345                 350

Arg Leu Arg Ile Glu Arg Gly Asp Asp Glu Gly Gly Val Gln Glu Glu
        355                 360                 365

Gln Gly Gly Val Ser Gln Val Gly Leu Thr Ala Ile Ala Val Gly Cys
    370                 375                 380

Arg Glu Leu Glu Tyr Ile Ala Ala Tyr Val Ser Asp Ile Thr Asn Gly
385                 390                 395                 400

Ala Leu Glu Ser Ile Gly Thr Phe Cys Lys Lys Leu Tyr Asp Phe Arg
                405                 410                 415

Leu Val Leu Leu Asp Arg Glu Glu Arg Ile Thr Asp Leu Pro Leu Asp
            420                 425                 430

Asn Gly Val Arg Ala Leu Leu Arg Gly Cys Thr Lys Leu Arg Arg Phe
        435                 440                 445

Ala Leu Tyr Leu Arg Pro Gly Gly Leu Ser Asp Ala Gly Leu Gly Tyr
    450                 455                 460

Ile Gly Gln Cys Ser Gly Asn Ile Gln Tyr Met Leu Leu Gly Asn Val
465                 470                 475                 480

Gly Glu Thr Asp Asp Gly Leu Ile Ser Phe Ala Leu Gly Cys Val Asn
                485                 490                 495

Leu Arg Lys Leu Glu Leu Arg Ser Cys Cys Phe Ser Glu Arg Ala Leu
            500                 505                 510

Ala Leu Ala Ile Leu His Met Pro Ser Leu Arg Tyr Val Trp Val Gln
    515                 520                 525

Gly Tyr Lys Ala Ser Gln Thr Gly Arg Asp Leu Met Leu Met Ala Arg
530                 535                 540

Pro Phe Trp Asn Ile Glu Phe Thr Pro Pro Asn Pro Lys Asn Gly Gly
545                 550                 555                 560

Trp Leu Met Glu Asp Gly Glu Pro Cys Val Asp Ser His Ala Gln Ile
                565                 570                 575

Leu Ala Tyr His Ser Leu Ala Gly Lys Arg Leu Asp Cys Pro Gln Ser
            580                 585                 590

Val Val Pro Leu Tyr Pro Ala
        595

<210> SEQ ID NO 24
<211> LENGTH: 597
<212> TYPE: PRT
<213> ORGANISM: Hevea brasiliensis

<400> SEQUENCE: 24

Met Glu Glu Glu Asn Gln Ser Asn Lys Ser Ser Arg Ile Ser Cys Ser
1               5                   10                  15

Ser Gly Met Ser Asp Val Val Leu Gly Cys Val Met Pro Tyr Ile His
                20                  25                  30

Asp Pro Arg Asp Arg Asp Ala Val Ser Leu Val Cys Arg Arg Trp Tyr
            35                  40                  45

Glu Leu Asp Ala Leu Thr Arg Lys His Ile Thr Ile Ala Phe Cys Tyr
```

```
            50                  55                  60
Thr Thr Ser Pro Asp Arg Leu Arg Arg Arg Phe Met His Leu Glu Ser
 65                  70                  75                  80

Leu Lys Leu Lys Gly Lys Pro Arg Ala Ala Met Phe Asn Leu Ile Pro
                 85                  90                  95

Glu Asp Trp Gly Gly Phe Val Thr Pro Trp Val Asn Glu Ile Ala Glu
            100                 105                 110

Ser Phe Asn Cys Leu Lys Ser Leu His Phe Arg Arg Met Ile Val Thr
            115                 120                 125

Asp Ser Asp Leu Glu Val Leu Ala Lys Ser Arg Gly Arg Val Leu Gln
        130                 135                 140

Val Phe Lys Leu Asp Lys Cys Ser Gly Phe Ser Thr Asp Gly Leu Leu
145                 150                 155                 160

His Val Gly Arg Leu Cys Arg Gln Leu Arg Thr Leu Phe Leu Glu Glu
                165                 170                 175

Ser Ser Ile Leu Glu Lys Asp Gly Ser Trp Leu His Glu Leu Ala Leu
            180                 185                 190

Asn Asn Thr Val Leu Glu Thr Leu Asn Leu Tyr Met Thr Asp Leu Asn
            195                 200                 205

Lys Val Arg Phe Glu Asp Leu Glu Leu Ile Ala Lys Asn Cys Arg Asn
210                 215                 220

Leu Val Ser Val Lys Ile Ser Asp Cys Glu Ile Leu Asp Leu Val Arg
225                 230                 235                 240

Phe Phe His Thr Ala Ala Leu Glu Glu Phe Cys Gly Gly Ser Phe
                245                 250                 255

Asn Asp Met Pro Asp Lys Tyr Ser Ala Val Thr Phe Pro Gln Lys Leu
            260                 265                 270

Cys Arg Leu Gly Leu Thr Tyr Met Gly Lys Asn Glu Met Arg Ile Val
            275                 280                 285

Phe Pro Phe Ala Ser Leu Leu Lys Lys Leu Asp Leu Leu Tyr Ala Leu
        290                 295                 300

Leu Asp Thr Glu Asp His Cys Leu Leu Ile Gln Lys Cys Phe Asn Leu
305                 310                 315                 320

Glu Val Leu Glu Thr Arg Asn Val Ile Gly Asp Arg Gly Leu Glu Val
                325                 330                 335

Leu Ala Ser Ser Cys Arg Arg Leu Lys Arg Leu Arg Ile Glu Leu Gly
            340                 345                 350

Ala Asp Glu Gln Glu Met Glu Asp Glu Glu Gly Val Val Ser Gln Arg
            355                 360                 365

Gly Leu Ile Ala Leu Ala Gln Gly Cys Leu Glu Leu Glu Tyr Met Ala
        370                 375                 380

Val Tyr Val Ser Asp Ile Thr Asn Ala Ala Leu Glu His Ile Gly Thr
385                 390                 395                 400

His Leu Arg Lys Leu Asn Asp Phe Arg Leu Val Leu Leu Asp Arg Glu
                405                 410                 415

Glu Arg Ile Thr Asp Leu Pro Leu Asp Arg Gly Val Gln Ser Leu Leu
            420                 425                 430

Met Gln Arg Lys Leu Arg Arg Phe Ala Leu Tyr Leu Arg Pro Gly Gly
            435                 440                 445

Leu Thr Asp Glu Gly Leu Gly Tyr Ile Gly Gln His Ser Lys Asn Val
        450                 455                 460

Arg Trp Met Leu Leu Gly Tyr Val Gly Glu Ser Asp Glu Gly Leu Leu
465                 470                 475                 480
```

```
Ala Phe Ser Lys Gly Cys Pro Ser Leu Gln Lys Leu Glu Met Arg Gly
            485                 490                 495

Cys Cys Phe Thr Glu Gly Ala Leu Ala Lys Ala Val Met Gln Leu Thr
            500                 505                 510

Ser Leu Arg Tyr Leu Trp Val Gln Gly Tyr Arg Ala Ser Ser Thr Arg
            515                 520                 525

Gly Arg Asp Leu Leu Ala Met Ala Arg Pro Phe Trp Asn Ile Glu Leu
            530                 535                 540

Ile Pro Pro Arg Lys Val Val Met Val Asn Gln Val Gly Glu Asp Val
545                 550                 555                 560

Val Val Glu His Pro Ala Gln Ile Leu Ala Tyr Tyr Ser Leu Ala Gly
            565                 570                 575

Pro Arg Thr Asp Phe Pro Asn Thr Val Val Pro Leu Asp Ser Cys Arg
            580                 585                 590

Ile Glu Ser Cys Lys
            595

<210> SEQ ID NO 25
<211> LENGTH: 591
<212> TYPE: PRT
<213> ORGANISM: Pisum sativum

<400> SEQUENCE: 25

Met Glu Glu Lys Asp Thr Cys Pro Gly Val Gly Arg Met Ser Ala Arg
1               5                   10                  15

Leu Thr Asp Val Val Leu Asp Cys Val Leu Pro Tyr Val His Asp Ser
            20                  25                  30

Lys Asp Arg Asp Ala Ile Ser Gln Val Cys Lys Arg Trp Tyr Glu Leu
            35                  40                  45

Asp Ser Ser Thr Arg Lys His Ile Thr Ile Ala Leu Cys Tyr Thr Thr
        50                  55                  60

Thr Pro Asp Arg Leu Arg Arg Phe Pro His Leu Glu Ser Leu Lys
65                  70                  75                  80

Leu Lys Gly Lys Pro Arg Ala Ala Met Phe Asn Leu Ile Pro Glu Asp
            85                  90                  95

Trp Gly Gly Phe Val Thr Pro Trp Val Arg Glu Ile Ser Lys Tyr Phe
            100                 105                 110

Asp Cys Leu Lys Ser Leu His Phe Arg Arg Met Ile Val Thr Asp Ser
            115                 120                 125

Asp Leu Gln Ile Leu Ala Arg Ser Arg His Gln Ser Leu His Ala Leu
        130                 135                 140

Lys Leu Glu Lys Cys Ser Gly Phe Ser Thr Asp Gly Leu Tyr Tyr Ile
145                 150                 155                 160

Cys His Ser Cys Lys Asn Leu Arg Val Leu Phe Met Glu Glu Ser Ser
            165                 170                 175

Val Asp Glu Lys Asp Gly Glu Trp Leu Arg Glu Leu Ala Leu Asn Asn
            180                 185                 190

Thr Phe Leu Glu Thr Leu Asn Phe Tyr Leu Thr Asp Ile Asn Ser Ile
            195                 200                 205

Arg Ile Gln Asp Leu Glu Leu Val Ala Lys Asn Cys Pro His Leu Val
        210                 215                 220

Ser Val Lys Ile Thr Asp Cys Glu Ile Leu Ser Leu Val Asn Phe Phe
225                 230                 235                 240

Arg Tyr Ala Ser Ser Leu Glu Glu Phe Cys Gly Gly Ser Tyr Asn Glu
```

```
                    245                 250                 255

Asp Pro Glu Lys Tyr Ala Ala Val Ser Leu Pro Ala Lys Leu Asn Arg
            260                 265                 270

Leu Gly Leu Thr Tyr Ile Gly Lys Asn Glu Met Pro Ile Ala Phe Pro
        275                 280                 285

Tyr Ala Ala Gln Leu Lys Lys Leu Asp Leu Leu Tyr Ala Met Leu Asp
    290                 295                 300

Thr Glu Asp His Cys Thr Leu Ile Gly Lys Cys Pro Asn Leu Glu Ile
305                 310                 315                 320

Leu Glu Ser Arg Asn Val Ile Gly Asp Arg Gly Leu Glu Val Leu Ala
                325                 330                 335

Arg Cys Cys Lys Lys Leu Lys Arg Leu Arg Ile Glu Arg Gly Asp Asp
            340                 345                 350

Asp Gln Gly Met Glu Asp Glu Asp Gly Ile Val Ser Gln Arg Gly Leu
        355                 360                 365

Ile Ala Leu Ser His Gly Cys Pro Glu Leu Glu Tyr Met Ala Val Tyr
    370                 375                 380

Val Ser Asp Ile Thr Asn Ala Ser Leu Glu His Ile Gly Thr His Leu
385                 390                 395                 400

Lys Asn Leu Cys Asp Phe Arg Leu Val Leu Leu Asp Arg Glu Glu Lys
                405                 410                 415

Ile Thr Asp Leu Pro Leu Asp Asn Gly Val Arg Ala Leu Leu Arg Gly
            420                 425                 430

Cys Glu Lys Leu Lys Arg Phe Ala Leu Tyr Leu Arg Pro Gly Gly Leu
        435                 440                 445

Thr Asp Val Gly Leu Gly Tyr Ile Gly Gln Tyr Ser Pro Asn Val Arg
    450                 455                 460

Trp Ile Leu Leu Gly Tyr Val Gly Glu Thr Asp Ala Gly Leu Leu Glu
465                 470                 475                 480

Phe Ser Lys Gly Cys Pro Ser Leu Gln Lys Leu Glu Met Arg Gly Cys
                485                 490                 495

Ser Phe Phe Thr Glu Tyr Ala Leu Ala Val Ala Ala Thr Arg Leu Thr
            500                 505                 510

Ser Leu Arg Tyr Leu Trp Val Gln Gly Tyr Gly Ala Ser Thr Ser Gly
        515                 520                 525

Leu Asp Leu Leu Val Met Ala Arg Pro Tyr Trp Asn Ile Glu Leu Ile
    530                 535                 540

Pro Ser Arg Val Val Thr Asp His His Pro Ala His Ile Leu Ala
545                 550                 555                 560

Tyr Tyr Ser Leu Ala Gly Pro Arg Ser Asp Phe Pro Asp Thr Val Ile
                565                 570                 575

Pro Leu Val Pro Ala Thr Thr Ala Ala Ser Tyr Phe Val Asn Arg
            580                 585                 590
```

<210> SEQ ID NO 26
<211> LENGTH: 605
<212> TYPE: PRT
<213> ORGANISM: Nicotiana attenuata

<400> SEQUENCE: 26

```
Met Glu Glu Arg Ser Ser Thr Arg Leu Pro Thr Gly Ser Tyr Thr Asn
1               5                   10                  15

Asp Asn Thr Val Trp Glu Cys Val Ile Pro Tyr Ile Thr Glu Ser Arg
            20                  25                  30
```

```
Asp Arg Asp Ala Val Ser Leu Val Cys Lys Arg Trp Trp Gln Ile Asp
     35                  40                  45

Ala Ile Thr Arg Lys His Ile Thr Met Ala Leu Cys Tyr Thr Ala Lys
 50                  55                  60

Pro Glu Gln Leu Ser Arg Arg Phe Pro His Leu Glu Ser Leu Lys Leu
 65                  70                  75                  80

Lys Gly Lys Pro Arg Ala Ala Met Phe Asn Leu Ile Pro Glu Asp Trp
                 85                  90                  95

Gly Gly Tyr Val Thr Pro Trp Val Val Glu Ile Thr Lys Ser Phe Ser
             100                 105                 110

Lys Leu Lys Ala Leu His Phe Arg Arg Met Ile Val Arg Asp Ser Asp
         115                 120                 125

Leu Glu Leu Val Ala Met Asn Arg Gly Lys Val Leu Gln Val Leu Lys
     130                 135                 140

Leu Asp Lys Cys Ser Gly Phe Ser Thr Asp Gly Leu Leu His Ile Cys
145                 150                 155                 160

Arg Ser Cys Arg Asn Leu Arg Thr Leu Phe Leu Glu Glu Ser Ser Ile
                 165                 170                 175

Val Glu Asn Asp Gly Glu Trp Val His Asp Leu Ala Val Asn Asn Thr
             180                 185                 190

Val Leu Glu Asn Leu Asn Phe Tyr Met Thr Asp Leu Val Gln Val Arg
         195                 200                 205

Ala Glu Asp Leu Glu Leu Ile Ala Arg Asn Cys Lys Ser Leu Val Ser
     210                 215                 220

Met Lys Ile Ser Glu Cys Glu Leu Ala Asn Leu Leu Gly Phe Phe Arg
225                 230                 235                 240

Ala Ala Val Ala Leu Glu Glu Phe Gly Gly Gly Ser Phe Asn Asp Gln
                 245                 250                 255

Pro Glu Pro Val Pro Glu Asn Gly Tyr Asn Glu Gln Leu Glu Lys Tyr
             260                 265                 270

Ala Ala Val Val Ser Pro Pro Arg Leu Cys Gln Leu Gly Leu Thr Tyr
         275                 280                 285

Leu Gly Lys Tyr Glu Met Pro Ile Leu Phe Pro Ile Ala Ser Arg Leu
     290                 295                 300

Thr Lys Leu Asp Leu Leu Tyr Ala Leu Leu Asp Thr Ala His Cys
305                 310                 315                 320

Phe Leu Leu Gln Arg Cys Pro Asn Leu Glu Ile Leu Glu Thr Arg Asn
                 325                 330                 335

Val Val Gly Asp Arg Gly Leu Glu Val Leu Gly Gln Tyr Cys Lys Arg
             340                 345                 350

Leu Lys His Leu Arg Ile Glu Arg Gly Ala Asp Asp Gln Glu Met Glu
         355                 360                 365

Asp Glu Gln Gly Ala Val Thr His Arg Gly Leu Thr Asp Leu Ala Lys
     370                 375                 380

Gly Cys Leu Glu Leu Glu Tyr Met Ala Val Tyr Val Ser Asp Ile Thr
385                 390                 395                 400

Asn Glu Ala Phe Glu Asn Ile Gly Thr Tyr Leu Lys Asn Leu Cys Asp
                 405                 410                 415

Phe Arg Leu Val Leu Leu Asp Arg Glu Glu Arg Ile Thr Asp Leu Pro
             420                 425                 430

Leu Asp Asn Gly Val Arg Ala Leu Leu Arg Gly Cys Tyr Lys Leu Arg
         435                 440                 445

Arg Phe Ala Leu Tyr Val Arg Pro Gly Gly Leu Thr Asp Val Gly Leu
```

```
                    450                 455                 460
Ser Tyr Val Gly Arg Tyr Ser Pro Asn Val Arg Trp Met Leu Trp Gly
465                 470                 475                 480

Tyr Val Gly Glu Ser Asp Glu Gly Leu Leu Lys Phe Leu Lys Asp Val
                    485                 490                 495

Leu Thr Cys Lys Ala Arg Ser Glu Arg Leu Leu Phe Ser Glu Arg Ala
                500                 505                 510

Leu Ala Leu Ala Ala Met Gln Leu Lys Ser Leu Arg Tyr Leu Trp Val
                515                 520                 525

Gln Gly Tyr Arg Ala Ser Ser Ala Gly Arg Asp Leu Leu Ala Met Ala
                530                 535                 540

Arg Pro Phe Trp Asn Ile Glu Leu Ile Pro Ala Arg Arg Val Val Ser
545                 550                 555                 560

Ser Glu Gly Asn Asn Gly Glu Thr Ile Val Ala Glu His Pro Ala His
                565                 570                 575

Ile Leu Ala Tyr Tyr Ser Leu Ala Gly Gln Arg Thr Asp Phe Pro Asp
                580                 585                 590

Thr Val Arg Pro Leu Asp Pro Asn Ser Leu Leu Ala Glu
                595                 600                 605

<210> SEQ ID NO 27
<211> LENGTH: 590
<212> TYPE: PRT
<213> ORGANISM: Glycine max

<400> SEQUENCE: 27

Met Thr Glu Asp Arg Asn Val Arg Lys Thr Arg Val Val Asp Leu Val
1               5                   10                  15

Leu Asp Cys Val Ile Pro Tyr Ile Asp Asp Pro Lys Asp Arg Asp Ala
                20                  25                  30

Val Ser Gln Val Cys Arg Arg Trp Tyr Glu Leu Asp Ser Leu Thr Arg
            35                  40                  45

Lys His Val Thr Ile Ala Leu Cys Tyr Thr Thr Thr Pro Ala Arg Leu
        50                  55                  60

Arg Arg Arg Phe Pro His Leu Glu Ser Leu Lys Leu Lys Gly Lys Pro
65                  70                  75                  80

Arg Ala Ala Met Phe Asn Leu Ile Pro Glu Asp Trp Gly Gly His Val
                85                  90                  95

Thr Pro Trp Val Lys Glu Ile Ser Gln Tyr Phe Asp Cys Leu Lys Ser
                100                 105                 110

Leu His Phe Arg Arg Met Ile Val Lys Asp Ser Asp Leu Arg Asn Leu
            115                 120                 125

Ala Arg Asp Arg Gly His Val Leu His Ser Leu Lys Leu Asp Lys Cys
        130                 135                 140

Ser Gly Phe Thr Thr Asp Gly Leu Phe His Ile Gly Arg Phe Cys Lys
145                 150                 155                 160

Ser Leu Arg Val Leu Phe Leu Glu Glu Ser Ile Val Glu Lys Asp
                165                 170                 175

Gly Glu Trp Leu His Glu Leu Ala Leu Asn Asn Thr Val Leu Glu Thr
            180                 185                 190

Leu Asn Phe Tyr Leu Thr Asp Ile Ala Val Val Lys Ile Gln Asp Leu
        195                 200                 205

Glu Leu Leu Ala Lys Asn Cys Pro Asn Leu Val Ser Val Lys Leu Thr
    210                 215                 220
```

Asp Ser Glu Ile Leu Asp Leu Val Asn Phe Phe Lys His Ala Ser Ala
225                 230                 235                 240

Leu Glu Glu Phe Cys Gly Gly Thr Tyr Asn Glu Glu Pro Glu Lys Tyr
            245                 250                 255

Ser Ala Ile Ser Leu Pro Ala Lys Leu Cys Arg Leu Gly Leu Thr Tyr
            260                 265                 270

Ile Gly Lys Asn Glu Leu Pro Ile Val Phe Met Phe Ala Ala Val Leu
        275                 280                 285

Lys Lys Leu Asp Leu Leu Tyr Ala Met Leu Asp Thr Glu Asp His Cys
290                 295                 300

Met Leu Ile Gln Lys Cys Pro Asn Leu Glu Val Leu Glu Thr Arg Asn
305                 310                 315                 320

Val Ile Gly Asp Arg Gly Leu Glu Val Leu Gly Arg Cys Cys Lys Arg
            325                 330                 335

Leu Lys Arg Leu Arg Ile Glu Arg Gly Asp Asp Asp Gln Gly Met Glu
            340                 345                 350

Asp Glu Glu Gly Thr Val Ser His Arg Gly Leu Ile Ala Leu Ser Gln
            355                 360                 365

Gly Cys Ser Glu Leu Glu Tyr Met Ala Val Tyr Val Ser Asp Ile Thr
370                 375                 380

Asn Ala Ser Leu Glu His Ile Gly Thr His Leu Lys Asn Leu Cys Asp
385                 390                 395                 400

Phe Arg Leu Val Leu Leu Asp His Glu Glu Lys Ile Thr Asp Leu Pro
            405                 410                 415

Leu Asp Asn Gly Val Arg Ala Leu Leu Arg Gly Cys Asn Lys Leu Arg
            420                 425                 430

Arg Phe Ala Leu Tyr Leu Arg Arg Gly Gly Leu Thr Asp Val Gly Leu
            435                 440                 445

Gly Tyr Ile Gly Gln Tyr Ser Pro Asn Val Arg Trp Met Leu Leu Gly
450                 455                 460

Tyr Val Gly Glu Ser Asp Ala Gly Leu Leu Glu Phe Ser Lys Gly Cys
465                 470                 475                 480

Pro Ser Leu Gln Lys Leu Glu Met Arg Gly Cys Ser Phe Phe Ser Glu
            485                 490                 495

Arg Ala Leu Ala Val Ala Ala Thr Gln Leu Thr Ser Leu Arg Tyr Leu
            500                 505                 510

Trp Val Gln Gly Tyr Gly Val Ser Pro Ser Gly Arg Asp Leu Leu Ala
            515                 520                 525

Met Ala Arg Pro Phe Trp Asn Ile Glu Leu Ile Pro Ser Arg Lys Val
530                 535                 540

Ala Met Asn Thr Asn Ser Asp Glu Thr Val Val Val Glu His Pro Ala
545                 550                 555                 560

His Ile Leu Ala Tyr Tyr Ser Leu Ala Gly Gln Arg Ser Asp Phe Pro
            565                 570                 575

Asp Thr Val Val Pro Leu Asp Ala Thr Cys Val Asp Thr
            580                 585                 590

<210> SEQ ID NO 28
<211> LENGTH: 596
<212> TYPE: PRT
<213> ORGANISM: Sorghum bicolor

<400> SEQUENCE: 28

Met Gly Gly Glu Leu Pro Glu Pro Ser Arg Leu Arg Arg Ala Leu Ser
1               5                   10                  15

```
Phe Gly Cys Gly Ala Val Pro Glu Ala Leu His Leu Val Phe Gly
            20                  25                  30

Tyr Val Asp Asp Pro Arg Asp Arg Glu Ala Ala Ser Leu Val Cys Arg
        35                  40                  45

Arg Trp His Arg Ile Asp Ala Leu Ser Arg Lys His Val Thr Val Gly
    50                  55                  60

Phe Cys Tyr Ala Val Glu Pro Ala Arg Leu Leu Ala Arg Phe Pro Arg
65                  70                  75                  80

Leu Glu Ser Leu Ala Leu Lys Gly Arg Pro Arg Ala Ala Met Tyr Gly
                85                  90                  95

Leu Ile Pro Glu Asp Phe Gly Ala Tyr Ala Ala Pro Trp Val Ala Gln
            100                 105                 110

Leu Ala Ala Pro Leu Asp Cys Leu Lys Ala Leu His Leu Arg Arg Met
        115                 120                 125

Thr Val Thr Asp Glu Asp Ile Ala Val Leu Val Arg Ala Arg Gly Tyr
    130                 135                 140

Met Leu Gln Val Leu Lys Leu Asp Lys Cys Ser Gly Phe Ser Thr Asp
145                 150                 155                 160

Ala Leu Arg Leu Val Ala Arg Ser Cys Arg Ser Leu Arg Thr Leu Phe
                165                 170                 175

Leu Glu Glu Cys Thr Ile Ala Asp Glu Gly Ser Glu Trp Leu His Glu
            180                 185                 190

Leu Ala Val Asn Asn Ser Val Leu Val Thr Leu Asn Phe Tyr Met Thr
        195                 200                 205

Asp Leu Arg Val Glu Pro Ala Asp Leu Glu Leu Leu Ala Lys Asn Cys
    210                 215                 220

Lys Ser Leu Ile Ser Leu Lys Met Ser Glu Cys Asp Leu Ser Asp Leu
225                 230                 235                 240

Ile Gly Phe Leu Gln Thr Ser Lys Gly Leu Gln Glu Phe Ala Gly Gly
                245                 250                 255

Ala Phe Ser Glu Val Gly Glu Tyr Thr Lys Tyr Glu Lys Val Lys Phe
            260                 265                 270

Pro Pro Arg Leu Cys Phe Leu Gly Gly Leu Thr Phe Met Ser Lys Asn
        275                 280                 285

Glu Met Gln Val Ile Phe Pro Tyr Ser Ala Met Leu Lys Lys Leu Asp
    290                 295                 300

Leu Gln Tyr Thr Cys Leu Thr Thr Glu Asp His Cys Gln Leu Ile Ala
305                 310                 315                 320

Lys Cys Pro Asn Leu Leu Val Leu Glu Val Arg Asn Val Ile Gly Asp
                325                 330                 335

Arg Gly Leu Glu Val Val Gly Asp Thr Cys Lys Lys Leu Arg Arg Leu
            340                 345                 350

Arg Ile Glu Arg Gly Asp Asp Pro Gly Gln Glu Glu Gln Gly Gly
        355                 360                 365

Val Ser Gln Ile Gly Leu Thr Ala Val Ala Val Gly Cys Arg Glu Leu
    370                 375                 380

Glu Tyr Ile Ala Ala Tyr Val Ser Asp Ile Thr Asn Gly Ala Leu Glu
385                 390                 395                 400

Ser Ile Gly Thr Phe Cys Lys Asn Leu Tyr Asp Phe Arg Leu Val Leu
                405                 410                 415

Leu Asp Lys Gln Asn Lys Ile Ala Asp Leu Pro Leu Asn Gly Val
            420                 425                 430
```

```
Arg Ala Leu Leu Arg Asn Cys Thr Lys Leu Arg Arg Phe Ala Phe Tyr
            435                 440                 445

Leu Arg Pro Gly Gly Leu Ser Asp Val Gly Leu Gly Tyr Ile Gly Leu
    450                 455                 460

Tyr Ser Gly Asn Ile Gln Tyr Met Leu Leu Gly Asn Val Gly Glu Ser
465                 470                 475                 480

Asp Asn Gly Leu Ile Gln Phe Ala Met Gly Cys Thr Asn Leu Arg Lys
                485                 490                 495

Leu Glu Leu Arg Ser Cys Cys Phe Ser Glu Arg Ala Leu Ala Val Ala
            500                 505                 510

Val Leu Gln Met Pro Leu Leu Arg Tyr Ile Trp Val Gln Gly Tyr Arg
            515                 520                 525

Ala Ser Gln Thr Gly Gln Asp Leu Met Leu Met Ala Arg Pro Tyr Trp
    530                 535                 540

Asn Ile Glu Phe Val Pro Pro Gly Pro Glu Ser Ala Tyr Arg Val Met
545                 550                 555                 560

Ala Asp Gly Gln Pro Cys Val Asp Thr His Ala Gln Val Leu Ala Tyr
                565                 570                 575

Tyr Ser Leu Ala Gly Arg Arg Pro Asp Cys Pro Gln Trp Leu Val Thr
            580                 585                 590

Leu His Pro Ala
        595

<210> SEQ ID NO 29
<211> LENGTH: 197
<212> TYPE: PRT
<213> ORGANISM: Arabidopsis thaliana

<400> SEQUENCE: 29

Met Ser Lys Ala Thr Ile Glu Leu Asp Phe Leu Gly Leu Glu Lys Lys
1               5                   10                  15

Gln Thr Asn Asn Ala Pro Lys Pro Lys Phe Gln Lys Phe Leu Asp Arg
            20                  25                  30

Arg Arg Ser Phe Arg Asp Ile Gln Gly Ala Ile Ser Lys Ile Asp Pro
        35                  40                  45

Glu Ile Ile Lys Ser Leu Leu Ala Ser Thr Gly Asn Asn Ser Asp Ser
    50                  55                  60

Ser Ala Lys Ser Arg Ser Val Pro Ser Thr Pro Arg Glu Asp Gln Pro
65                  70                  75                  80

Gln Ile Pro Ile Ser Pro Val His Ala Ser Leu Ala Arg Ser Ser Thr
                85                  90                  95

Glu Leu Val Ser Gly Thr Val Pro Met Thr Ile Phe Tyr Asn Gly Ser
            100                 105                 110

Val Ser Val Phe Gln Val Ser Arg Asn Lys Ala Gly Glu Ile Met Lys
        115                 120                 125

Val Ala Asn Glu Ala Ala Ser Lys Lys Asp Glu Ser Ser Met Glu Thr
    130                 135                 140

Asp Leu Ser Val Ile Leu Pro Thr Thr Leu Arg Pro Lys Leu Phe Gly
145                 150                 155                 160

Gln Asn Leu Glu Gly Asp Leu Pro Ile Ala Arg Arg Lys Ser Leu Gln
                165                 170                 175

Arg Phe Leu Glu Lys Arg Lys Glu Arg Leu Val Ser Thr Ser Pro Tyr
            180                 185                 190

Tyr Pro Thr Ser Ala
        195
```

```
<210> SEQ ID NO 30
<211> LENGTH: 19
<212> TYPE: PRT
<213> ORGANISM: Artificial Sequence
<220> FEATURE:
<223> OTHER INFORMATION: JAZ Jas motif consensus sequence
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (10)..(10)
<223> OTHER INFORMATION: Any amino acid
<220> FEATURE:
<221> NAME/KEY: MISC_FEATURE
<222> LOCATION: (11)..(11)
<223> OTHER INFORMATION: Any amino acid
<220> FEATURE:
<221> NAME/KEY: MISC_FEATURE
<222> LOCATION: (13)..(13)
<223> OTHER INFORMATION: Any amino acid
<220> FEATURE:
<221> NAME/KEY: MISC_FEATURE
<222> LOCATION: (14)..(14)
<223> OTHER INFORMATION: Any amino acid
<220> FEATURE:
<221> NAME/KEY: MISC_FEATURE
<222> LOCATION: (15)..(15)
<223> OTHER INFORMATION: Any amino acid
<220> FEATURE:
<221> NAME/KEY: MISC_FEATURE
<222> LOCATION: (16)..(16)
<223> OTHER INFORMATION: Any amino acid
<220> FEATURE:
<221> NAME/KEY: MISC_FEATURE
<222> LOCATION: (17)..(17)
<223> OTHER INFORMATION: Any amino acid

<400> SEQUENCE: 30

Ser Leu Xaa Xaa Phe Xaa Xaa Lys Arg Xaa Xaa Arg Xaa Xaa Xaa Xaa
1               5                   10                  15

Xaa Pro Tyr

<210> SEQ ID NO 31
<211> LENGTH: 594
<212> TYPE: PRT
<213> ORGANISM: Arabidopsis thaliana

<400> SEQUENCE: 31

Met Gln Lys Arg Ile Ala Leu Ser Phe Pro Glu Glu Val Leu Glu His
1               5                   10                  15

Val Phe Ser Phe Ile Gln Leu Asp Lys Asp Arg Asn Ser Val Ser Leu
                20                  25                  30

Val Cys Lys Ser Trp Tyr Glu Ile Glu Arg Trp Cys Arg Arg Lys Val
            35                  40                  45

Phe Ile Gly Asn Cys Tyr Ala Val Ser Pro Ala Thr Val Ile Arg Arg
        50                  55                  60
```

```
Phe Pro Lys Val Arg Ser Val Glu Leu Lys Gly Lys Pro His Phe Ala
 65                  70                  75                  80

Asp Phe Asn Leu Val Pro Asp Gly Trp Gly Tyr Val Tyr Pro Trp
                 85                  90                  95

Ile Glu Ala Met Ser Ser Tyr Thr Trp Leu Glu Ile Arg Leu
            100                 105                 110

Lys Arg Met Val Val Thr Asp Cys Leu Glu Leu Ile Ala Lys Ser
            115                 120                 125

Phe Lys Asn Phe Lys Val Leu Val Leu Ser Ser Cys Glu Gly Phe Ser
            130                 135                 140

Thr Asp Gly Leu Ala Ala Ile Ala Ala Thr Cys Arg Asn Leu Lys Glu
145                 150                 155                 160

Leu Asp Leu Arg Glu Ser Asp Val Asp Asp Val Ser Gly His Trp Leu
                165                 170                 175

Ser His Phe Pro Asp Thr Tyr Thr Ser Leu Val Ser Leu Asn Ile Ser
                180                 185                 190

Cys Leu Ala Ser Glu Val Ser Phe Ser Ala Leu Glu Arg Leu Val Thr
            195                 200                 205

Arg Cys Pro Asn Leu Lys Ser Leu Lys Leu Asn Arg Ala Val Pro Leu
210                 215                 220

Glu Lys Leu Ala Thr Leu Leu Gln Arg Ala Pro Gln Leu Glu Glu Leu
225                 230                 235                 240

Gly Thr Gly Gly Tyr Thr Ala Glu Val Arg Pro Asp Val Tyr Ser Gly
                245                 250                 255

Leu Ser Val Ala Leu Ser Gly Cys Lys Glu Leu Arg Cys Leu Ser Gly
            260                 265                 270

Phe Trp Asp Ala Val Pro Ala Tyr Leu Pro Ala Val Tyr Ser Val Cys
            275                 280                 285

Ser Arg Leu Thr Thr Leu Asn Leu Ser Tyr Ala Thr Val Gln Ser Tyr
            290                 295                 300

Asp Leu Val Lys Leu Leu Cys Gln Cys Pro Lys Leu Gln Arg Leu Trp
305                 310                 315                 320

Val Leu Asp Tyr Ile Glu Asp Ala Gly Leu Glu Val Leu Ala Ser Thr
                325                 330                 335

Cys Lys Asp Leu Arg Glu Leu Arg Val Phe Pro Ser Glu Pro Phe Val
            340                 345                 350

Met Glu Pro Asn Val Ala Leu Thr Glu Gln Gly Leu Val Ser Val Ser
            355                 360                 365

Met Gly Cys Pro Lys Leu Glu Ser Val Leu Tyr Phe Cys Arg Gln Met
            370                 375                 380

Thr Asn Ala Ala Leu Ile Thr Ile Ala Arg Asn Arg Pro Asn Met Thr
385                 390                 395                 400

Arg Phe Arg Leu Cys Ile Ile Glu Pro Lys Ala Pro Asp Tyr Leu Thr
                405                 410                 415

Leu Glu Pro Leu Asp Ile Gly Phe Gly Ala Ile Val Glu His Cys Lys
                420                 425                 430

Asp Leu Arg Arg Leu Ser Leu Ser Gly Leu Leu Thr Asp Lys Val Phe
            435                 440                 445

Glu Tyr Ile Gly Thr Tyr Ala Lys Lys Met Glu Met Leu Ser Val Ala
            450                 455                 460

Phe Ala Gly Asp Ser Asp Leu Gly Met His His Val Leu Ser Gly Cys
465                 470                 475                 480
```

```
                                                -continued

Asp Ser Leu Arg Lys Leu Glu Ile Arg Asp Cys Pro Phe Gly Asp Lys
                485                 490                 495

Ala Leu Leu Ala Asn Ala Ser Lys Leu Glu Thr Met Arg Ser Leu Trp
            500                 505                 510

Met Ser Ser Cys Ser Val Ser Phe Gly Ala Cys Lys Leu Leu Gly Gln
        515                 520                 525

Lys Met Pro Lys Leu Asn Val Glu Val Ile Asp Glu Arg Gly Ala Pro
    530                 535                 540

Asp Ser Arg Pro Glu Ser Cys Pro Val Glu Arg Val Phe Ile Tyr Arg
545                 550                 555                 560

Thr Val Ala Gly Pro Arg Phe Asp Met Pro Gly Phe Val Trp Asn Met
                565                 570                 575

Asp Gln Asp Ser Thr Met Arg Phe Ser Arg Gln Ile Ile Thr Thr Asn
            580                 585                 590

Gly Leu
```

METHODS AND COMPOSITIONS FOR TARGETED PROTEIN DEGRADATION

RELATED APPLICATIONS

The present application claims priority to U.S. Provisional Patent Application No. 61/352,758, filed Jun. 8, 2010, the disclosure of which is incorporated by reference herein in its entirety.

STATEMENT OF GOVERNMENT INTEREST

This invention was made with government support under grant number 2RO1CA107134 awarded by National Institutes of Health. The government has certain rights in the invention.

BACKGROUND

Reverse genetic approaches are a powerful laboratory tool for determining the function of a target protein. The target protein is "knocked down," and cellular changes are observed in order to infer the normal function of the knocked down target. Methods for knocking down a target protein by manipulating DNA transcription and RNA translation are well established. Among the most commonly used are gene knockout in whole animals and degradation of target mRNA using siRNA and shRNA techniques. However, delivery of RNA molecules can be cumbersome, and these methods often cannot achieve 100% efficiency.

Although several methods exist for knocking down a protein target at the transcription and translation levels, there are very few options for knocking down a protein target once the protein has been made. Such methods are desirable because most small molecule therapeutics operate by manipulating proteins directly. Therefore, targeted degradation techniques that operate at the protein level provide the best tool for examining the potential effects of small molecule therapeutics.

The ideal protein knock down system would function at the protein level, and would be capable of tightly controlling protein levels in a temporal manner. Temporal control of protein levels allows down-regulation of proteins that are essential for the full development of a system or pathway, and can be used to study dynamic biological functions which are otherwise difficult to manipulate.

SUMMARY

In certain embodiments, methods are provided for targeted protein degradation. In certain of these embodiments, the protein targeted for degradation is tagged with one or more JAZ peptide tags as provided herein. The target protein is expressed in a non-plant host cell that also expresses the *Arabidopsis* protein COI1 or a homolog thereof, and a molecule that binds the COI1/JA-Ile binding pocket of COI1 is introduced into the cell to induce target protein degradation. In certain embodiments, the peptide tag comprises, consists of, or consists essentially of an amino acid sequence as set forth in SEQ ID NOs: 5, 6, 7, or 13. In certain embodiments, the molecule that binds the COI1/JA-Ile binding pocket of COI1 is coronatine, JA, or a JA amino acid conjugate such as JA-Ile. In certain embodiments, an inositol pentakisphosphate cofactor may also be introduced into the cell. In certain embodiments, the non-plant host cell may be a eukaryotic cell such as a yeast or mammalian cell. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*. The target protein may be either an endogenous host cell protein or an exogenous protein. In those embodiments wherein the target protein is an endogenous host cell protein, the peptide tag may be attached to the target protein by introducing a DNA sequence encoding the peptide tag adjacent to the DNA sequence encoding the target protein in the host cell, such that the target protein is expressed with the peptide tag attached. In those embodiments wherein the target protein is an exogenous protein, the target protein may be introduced into the host cell via a DNA sequence encoding the target protein and the peptide tag. In certain embodiments, target protein degradation may be halted by deactivating the molecule that binds the COI1/JA-Ile binding pocket of COI1 or removing it from the cell. In other embodiments, target protein degradation may be halted by natural degradation of the molecule that binds the COI1/JA-Ile binding pocket of COI1.

In certain embodiments, methods are provided for targeted protein degradation. In certain of these embodiments, the protein targeted for degradation is tagged with one or more peptide tags comprising an amino acid sequence as set forth in SEQ ID NOs:5, 6, 7, or 13. The target protein is expressed in a non-plant host cell that also expresses the *Arabidopsis* protein COI1 or a homolog thereof, and coronatine or JA-Ile is introduced into the cell to induce target protein degradation. In certain embodiments, an inositol pentakisphosphate cofactor may also be introduced into the cell. In certain embodiments, the non-plant host cell may be a eukaryotic cell such as a yeast or mammalian cell. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*. The target protein may be either an endogenous host cell protein or an exogenous protein. In those embodiments wherein the target protein is an endogenous host cell protein, the peptide tag may be attached to the target protein by introducing a DNA sequence encoding the peptide tag adjacent to the DNA sequence encoding the target protein in the host cell, such that the target protein is expressed with the peptide tag attached. In those embodiments wherein the target protein is an exogenous protein, the target protein may be introduced into the host cell via a DNA sequence encoding the target protein and the peptide tag. In certain embodiments, target protein degradation may be halted by deactivating coronatine or JA-Ile or removing them from the cell. In other embodiments, target protein degradation may be halted by natural degradation of coronatine or JA-Ile.

In certain embodiments, methods are provided for targeted protein degradation in a non-plant host cell by fusing a target protein to a peptide tag as provided herein, introducing a DNA sequence encoding *Arabidopsis* COI1 or a homolog thereof into the host cell, culturing the host cell under conditions that result in the expression of the target protein and *Arabidopsis* COI1 or a homolog thereof, and introducing a molecule that binds the COI1/JA-Ile binding pocket of COI1 into the host cell. In certain embodiments, the peptide tag comprises, consists of, or consists essentially of an amino acid sequence as set forth in SEQ ID NOs:5, 6, 7, or 13. In certain embodiments, the molecule that binds the COI1/JA-Ile binding pocket of COI1 is coronatine, JA, or a JA amino acid conjugate such as JA-Ile. In certain embodiments, an inositol pentakisphosphate cofactor may also be introduced into the cell. In certain embodiments, the non-plant host cell may be a eukaryotic cell such as a yeast or mammalian cell. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*. The target protein may be either an endogenous host cell protein or an exogenous protein. In those embodiments wherein the target protein is an endogenous host cell protein, the peptide tag may be attached to the target protein by introducing a DNA sequence encoding the peptide tag adjacent to the DNA sequence encoding the target protein in the host cell, such that the target protein is expressed with the peptide tag attached. In those embodiments wherein the target protein is an exogenous protein, the target protein may be introduced into the host cell via a DNA sequence encoding the target protein and the peptide tag. In certain embodiments, target protein degradation may be halted by deactivating the molecule that binds the COI1/JA-Ile binding pocket of COI1 or removing it from the cell. In other embodiments, target protein degradation may be halted by natural degradation of the molecule that binds the COI1/JA-Ile binding pocket of COI1.

In certain embodiments, methods are provided for targeted protein degradation in a non-plant host cell by fusing a target protein to a peptide tag comprising, consisting of, or consisting essentially of an amino acid sequence as set forth in SEQ ID NOs:5, 6, 7, or 13, introducing a DNA sequence encoding *Arabidopsis* COI1 or a homolog thereof into the host cell, culturing the host cell under conditions that result in the expression of the target protein and *Arabidopsis* COI1 or a homolog thereof, and introducing coronatine or JA-Ile into the host cell. In certain embodiments, an inositol pentakisphosphate cofactor may also be introduced into the cell. In certain embodiments, the non-plant host cell may be a eukaryotic cell such as a yeast or mammalian cell. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*. The target protein may be either an endogenous host cell protein or an exogenous protein. In those embodiments wherein the target protein is an endogenous host cell protein, the peptide tag may be attached to the target protein by introducing a DNA sequence encoding the peptide tag adjacent to the DNA sequence encoding the target protein in the host cell, such that the target protein is expressed with the peptide tag attached. In those embodiments wherein the target protein is an exogenous protein, the target protein may be introduced into the host cell via a DNA sequence encoding the target protein and the peptide tag. In certain embodiments, target protein degradation may be halted by deactivating coronatine or removing it from the cell. In other embodiments, target protein degradation may be halted by natural degradation of coronatine.

In certain embodiments, methods are provided for targeted protein degradation in a host animal by introducing a DNA sequence encoding the target protein linked to a peptide tag as provided herein and another DNA sequence encoding *Arabidopsis* COI1 or a homolog thereof, expressing the tagged target protein and COI1, and then administering a molecule that binds the COI1/JA-Ile binding pocket of COI1 to the animal. In certain embodiments, an inositol pentakisphosphate cofactor may also be introduced into the cell. In certain embodiments, the peptide tag comprises, consists of, or consists essentially of an amino acid sequence as set forth in SEQ ID NOs:5, 6, 7, or 13. In certain embodiments, the molecule that binds the COI1/JA-Ile binding pocket of COI1 is coronatine, JA, or a JA amino acid conjugate such as JA-Ile. In certain embodiments, the animal is a mammal, and in certain of these embodiments the animal is a mouse. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*.

In certain embodiments, methods are provided for targeted protein degradation in a host animal by introducing a DNA sequence encoding the target protein linked to a peptide tag comprising, consisting of, or consisting essentially of an amino acid sequence as set forth in SEQ ID NOs:5, 6, 7, or 13 and another DNA sequence encoding *Arabidopsis* COI1 or a homolog thereof, expressing the tagged target protein and COI1, and then administering coronatine or JA-Ile to the animal. In certain embodiments, an inositol pentakisphosphate cofactor may also be introduced into the cell. In certain embodiments, the animal is a mammal, and in certain of these embodiments the animal is a mouse. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella patens*.

In certain embodiments, non-plant host cells are provided that comprise a DNA sequence encoding a target protein linked to a peptide tag comprising, consisting of, or consisting essentially of an amino acid sequence as set forth in SEQ ID NOs:5, 6, 7, or 13 and another DNA sequence encoding *Arabidopsis* COI1 or a homolog thereof. In certain embodiments, the cells further comprise an inositol pentakisphosphate cofactor. In certain embodiments, the non-plant host cell is a eukaryotic cell, and in certain of these embodiments the non-plant host cell is a yeast or mammalian cell. In certain embodiments, the *Arabidopsis* protein COI1 or a homolog thereof may be COI1 from *Arabidopsis thaliana* or *Arabidopsis lyrata*, or it may be a COI1 homolog from another plant or moss such as rice, tomato, grape, poplar, castor oil, corn, rubber tree, pea, wild tobacco, soybean, sorghum, wheat, or *Physcomitrella*.

In certain embodiments, methods are provided for targeting an endogenous target protein in a non-plant host cell for coronatine- or JA-Ile-induced degradation by introducing a DNA sequence encoding a peptide tag comprising, consisting of, or consisting essentially of an amino acid sequence as set forth in SEQ ID NOs:5, 6, 7, or 13 such that the DNA sequence is inserted adjacent to the gene encoding the endogenous target protein, and such that the target protein is expressed fused to the peptide tag.

In certain embodiments, peptides are provided for tagging a target protein for degradation, and in certain of these embodiments, the peptide tags comprise, consist of, or consist essentially of an amino acid sequence as set forth in SEQ ID NOs:5, 6, 7, or 13. Also provided in certain embodiments are isolated nucleic acid sequences encoding these peptide tags, as well as the use of the peptide tags in tagging target proteins for degradation.

In certain embodiments, kits are provided for targeted protein degradation. In certain embodiments, these kits may include one or more of the following: an isolated nucleic acid encoding a peptide tag as provided herein, an isolated nucleic acid encoding *Arabidopsis* COI1 or a homolog thereof, and a molecule that binds the COI1/JA-Ile binding pocket of COI1. In certain embodiments, the kit may further comprise a target protein or an isolated nucleic acid encoding a target protein, and/or an inositol pentakisphosphate cofactor. In certain embodiments, the peptide tag comprises, consists of, or consists essentially of an amino acid sequence as set forth in SEQ ID NOs:5, 6, 7, or 13. In certain embodiments, the molecule that binds the COI1/JA-Ile binding pocket of COI1 is coronatine, JA, or a JA amino acid conjugate such as JA-Ile. In certain embodiments, the kit further comprises instructions for use and/or other printed materials.

DETAILED DESCRIPTION

Figure 1:
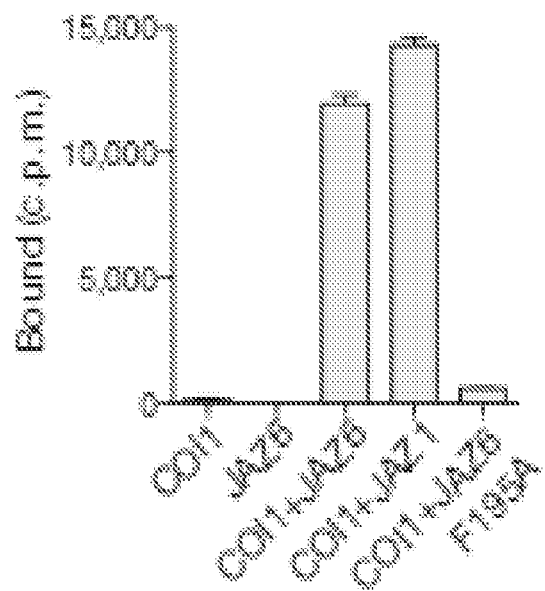
FIG. 1: A. Binding of $^3$H-coronatine (300 nM) to COI1 alone, JAZ6 alone, JAZ6/COI1, JAZ1/COI1, and JAZ6F195A/COI1. B. Saturation binding of $^3$H-coronatine to the complex of COI1/ASK1 in the presence of JAZ1 (▲, KD of 68±15 nM) and JAZ6 (■, KD of 48±13 nM).
Figure 1:
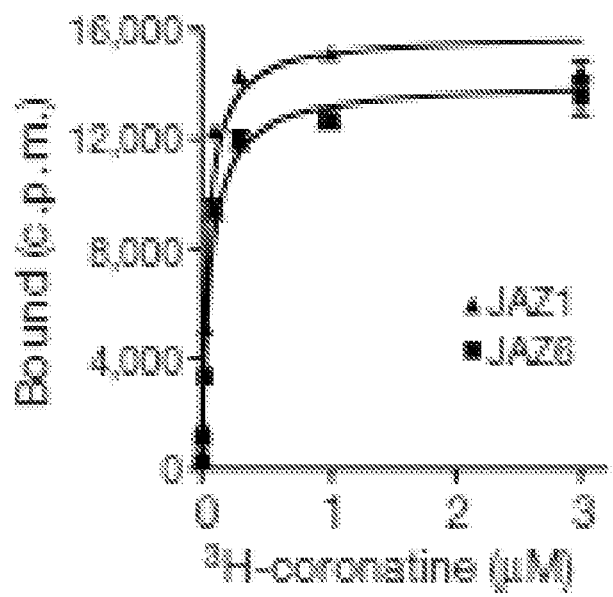

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

The following abbreviations are used herein: COR, coronatine; cpm, counts per minute; JA, jasmonic acid; JA-Ile, jasmonyl-L-isoleucine; JAZ, jasmonate ZIM-domain; LRR, leucine-rich repeat; ppm, parts per million; SCF, Skp1-Cullin-F box protein; sdm, site-directed mutants.

There are currently no satisfactory methods for knocking down a protein target in a temporally controlled manner using targeted protein degradation. Several previous attempts at developing such a method have utilized the ubiquitin proteasome system. However, all of these methods have serious drawbacks.

One method that employs the ubiquitin proteasome system utilizes peptide-small molecule hybrids ("protacs"). These chimeric molecules encourage binding of a target protein to the SCF$^{\beta TrCP}$ complex, resulting in proteolysis of the target (Sakamoto 2000). However, the protacs used in these methods are not membrane-permeable, and therefore require modifications to increase cell permeability or the use of microinjection. Another disadvantage of this system is off-target effects that arise from "swamping out" SCF$^{\beta TrCP}$ and blocking its ability to interact with endogenous targets. Thus, modification of endogenous SCF complexes has shown very limited usefulness as a reverse genetics tool. Another previously developed method for targeted protein degradation utilized chimeric fusions consisting of the target protein and large binding domains of proteins targeted for degradation at SCF complexes. One such system paired the target protein with the chi retinoblastoma (Rb)-binding domain derived from the human papillomavirus (HPV) oncoprotein E7 (Zhou 2000). This method showed some success in yeast and mammalian systems, but it is not inducible and requires the use of an obstructive large tag. A similar chimeric approach required engineering of the F-box protein β-TrCP with a small, phosphorylated peptide that encourages binding of a particular target molecule to the F-box protein (Zhang 2003). However, this system required a great deal of engineering in order for the chimeric F-box protein to recognize only the target of interest and not endogenous targets. Therefore, it has not been widely used.

Recently, researchers in Japan have developed a method that utilizes the *Arabidopsis* and tomato auxin receptor TIR1 for rapid, hormone-induced protein degradation (Nishimura Nature Methods 2009). TIR1 integrates into the yeast and mammalian SCF scaffold and degrades proteins with the AUX/IAA tag, the natural substrate of TIR1. However, this tag is over 20 kDa, a large tag by biochemistry standards. A smaller tag has not yet been identified. As such, the TIR1 system has limited usefulness.

The phytohormone jasmonic acid (JA) and its metabolites regulate a wide spectrum of plant physiology, participating in normal development and growth processes as well as defense responses to environmental and pathogenic stressors. JA is activated upon specific conjugation to the amino acid L-isoleucine, which produces the highly bioactive hormonal signal (3R,7S)-jasmonyl-L-isoleucine (JA-Ile). Coronatine (COR) is a *Pseudomonas syringae* virulence factor that structurally mimics JA-Ile.

The discovery of coronatine-insensitive mutants enabled the identification of COI1 as a key player in the JA pathway. *Arabidopsis* COI1 is an F-box protein that functions as the substrate-recruiting module of the Skp1-Cullin-F box protein (SCF) ubiquitin E3 ligase complex. Like other E3 ligases, SCF$^{COI1}$ is involved in the ubiquitination of proteins, which targets the proteins for subsequent degradation by the 26S proteasome.

*Arabidopsis* jasmonate ZIM-domain (JAZ) proteins such as JAZ1, JAZ6, JAZ7, and JAZ8 are SCF$^{COI1}$ substrate targets that associate with COI1 in a hormone-dependent manner. In the absence of hormone signal, the JAZ proteins actively repress the transcription factor MYC2, which binds to cis-acting elements of jasmonate-response genes. In response to cues that upregulate JA-Ile synthesis, the hormone stimulates the specific binding of JAZ proteins to COI1, leading to poly-ubiquitylation and subsequent degradation of the JAZ proteins by the 26S proteasome. JAZ degradation relieves repression of MYC2 and probably other transcription factors, permitting the expression of JA-responsive genes. The role of COI1-mediated JAZ degradation in JA signaling is analogous to auxin signaling through the F-box protein TIR1, which promotes hormone-dependent turnover of the AUX/IAA transcriptional repressors.

The experimental results provided herein disclose the identification and characterization of a complete jasmonate receptor comprising COI1, a JAZ peptide, and inositol pentakisphosphate. Coronatine was found to bind the complexes of COI1/JAZ1 and COI1/JAZ6 complexes with high affinity while displaying minimal binding affinity for COI1, JAZ1, or JAZ6 alone. Crystal structure studies were used to identify a coronatine- and JA-Ile-binding pocket on COI1. Binding of these molecules to the COI1 binding pocket increases binding affinity between COI1 and JAZ1. Coronatine has been found to play a similar role in the binding of JAZ2, JAZ3, JAZ4, JAZ5, JAZ6, JAZ8, JAZ9, JAZ10, JAZ11, and JAZ12 to COI1. A single isoform of inositol pentakisphosphate (Ins(1,2,4,5,6)P$_5$) was found to co-purify with COI1, and functional assays showed that this molecule is a critical cofactor in the interaction between COI1 and JAZ proteins.

The COI1 binding region of JAZ proteins had previously been mapped to a carboxy-terminal Jas motif. To precisely map the minimal region of the Jas motif that it is required for high affinity binding of COI1 to JAZ1 in the presence of coronatine, the JAZ1 degron and various derivatives thereof were analyzed. This led to the identification of specific JAZ peptide tags with enhanced binding affinity for COI1 in the presence of coronatine.

Provided herein in certain embodiments are compositions comprising one or more JAZ peptide tags capable of binding *Arabidopsis* COI1 or a homolog thereof, as well as nucleic acids encoding these JAZ peptide tags, methods of using these peptide tags to mark a target protein for degradation, and the use of these peptide tags in various methods and kits for temporally controlled protein degradation.

In certain embodiments, the JAZ peptide tags provided herein consist of, consist essentially of, or comprise the JAZ1 degron as set forth in SEQ ID NO: 1. In other embodiments, the peptide tags consist of, consist essentially of, or comprise an amino acid sequence that corresponds to the JAZ1 degron of SEQ ID NO:1 but with one or more additions, deletions, or substitutions. In certain of these embodiments, the peptide tags consist of, consist essentially of, or comprise the amino acid sequence of SEQ ID NO: 1 but with one or more deletions from the C-terminal end. In certain other of these embodiments, the peptide tags consist of, consist essentially of, or comprise the amino acid sequence of SEQ ID NO:1 but with one or more additions to the N-terminal end. In other embodiments, the peptide tags provided herein comprise a fragment of an *Arabidopsis* JAZ protein other than JAZ1, such as for example JAZ2, JAZ3, JAZ4, JAZ5, JAZ6, JAZ8, JAZ9, JAZ10, JAZ11, or JAZ12.

In certain preferred embodiments, the JAZ1 peptide tags disclosed herein consist of, consist essentially of, or comprise the amino acid sequence of SEQ ID NOs:5, 6, or 7. In other preferred embodiments, the peptide tags consist of, consist essentially of, or comprise an amino acid sequence that corresponds to the amino acid sequences of SEQ ID NOs:5, 6, or 7, but wherein one or more amino acid substitutions, additions, or deletions have been introduced into the sequence. For example, in certain embodiments the peptide tags may consist of, consist essentially of, or comprise the amino acid sequence $X_1X_2X_3X_4X_5RRX_8SLHRFLEKRKDRVX_{22}X_{23}X_{24}X_{25}X_{26}X_{27}$ (SEQ ID NO: 13), wherein $X_1$, $X_2$, $X_3$, $X_4$, and $X_5$ are each independently absent or any amino acid, $X_8$ is either Ala or Lys, and $X_{22}$, $X_{23}$, $X_{24}$, $X_{25}$, $X_{26}$, and $X_{27}$ are each independently absent or any amino acid. In certain of these embodiments, $X_1$ is either absent, Glu, or Val; $X_2$ is either absent, Leu, or Glu; $X_3$ is either absent, Pro, or Arg; $X_4$ is either absent or Ile; and $X_5$ is either absent or Ala. In certain embodiments, $X_{22}$ is either absent or Thr; $X_{23}$ is either absent or Ser; $X_{24}$ is either absent or Lys; $X_{25}$ is either absent or Ala; $X_{26}$ is either absent or Pro; and $X_{27}$ is either absent or Tyr.

The small, unobtrusive peptide tags provided herein are superior to the large chimeric tags used in previously developed methods for targeted protein destruction because they are less likely to interfere with protein function, complex formation, and subcellular localization. However, in certain embodiments, the peptide tags disclosed herein may comprise a longer sequence, such as for example the full-length JAZ1 polypeptide sequence as set forth in SEQ ID NO: 14 or the full-length JAZ10 polypeptide sequence set forth in SEQ ID NO:29. In other of these embodiments, the peptide tag may comprise the full-length JAZ2, JAZ3, JAZ4, JAZ5, JAZ6, JAZ8, JAZ9, JAZ11, or JAZ12 polypeptide sequence.

COI1 binding to a protein comprising a JAZ peptide tag as results in degradation of the protein. As disclosed herein, binding of coronatine or JA-Ile to a specific binding pocket in COI1 enhances the interaction of COI1 and the JAZ peptide. Thus, targeted protein degradation can be accomplished by tagging a target protein with a JAZ peptide tag as provided herein, then contacting the protein with COI1 in the presence of a molecule that binds to the coronatine/JA-Ile binding pocket of COI1.

As such, provided herein in certain embodiments are methods for targeted protein degradation that utilize one or more of 1) *Arabidopsis* COI1 or a homolog thereof, 2) a molecule that binds the COI1/JA-Ile binding pocket in COI1, 3) one or more JAZ peptide tags, and, optionally, 4) an inositol pentakisphosphate cofactor. Also provided herein are compositions and kits for carrying out these methods.

The crystal structure analysis provided herein shows that coronatine and JA-Ile interact with a specific set of residues in the COI1 binding pocket that includes R85, A86, F89, L91, R348, E350, A384, Y386, R409, V411, Y444, LA69, R496, and W519 of SEQ ID NO:15. Therefore, a "molecule that binds the COI1/JA-Ile binding pocket of COI1" as used herein refers to a molecule that interacts with one or more of these residues, and more preferably with all fourteen of these residues. As used herein, a molecule "interacts" with a particular COI1 binding pocket residue if, when the molecule is bound to COI1, any portion of the molecule resides within a molecular distance that is within the hydrogen bond or Van der Waals interaction radius (approximately 2.5 to 4 Å) of the residue. In certain embodiments of the compositions, methods, and kits provided herein, a molecule that binds the COI1/JA-Ile binding pocket of COI1 is coronatine. In other embodiments, the molecule is JA or a JA-amino acid conjugate such as JA-Ile, JA-L-leucine, JA-L-valine, or JA-L-alanine.

In those embodiments of the methods, compositions, and kits provided herein that utilize or comprise an inositol pentakisphosphate cofactor, the inositol pentakisphosphate cofactor may be inositol-1,2,4,5,6-pentakisphosphate. In other embodiments, the cofactor may be another molecule of the myo-inositol family, such as inositol-1,4,5,6-tetrakisphosphate.

In certain embodiments of the methods provided herein, one or more JAZ peptide tags are attached to or incorporated into a target protein. In the presence of molecule that binds the COI1/JA-Ile binding pocket of COI1, the JAZ peptide tag (and hence the target protein) binds to *Arabidopsis* COI1 or a homolog thereof with high affinity, resulting in target protein degradation.

Unlike previously developed methods for targeted protein destruction, the methods provided herein utilize small molecules that are membrane-permeable and require minimal engineering. The methods provided herein are rapidly inducible and easily reversible, and they do not require the use of large, obstructive tags. Thus, these methods represent a cheap, simple means for targeted protein destruction in vivo that is significantly superior to previously developed methods.

In certain embodiments of the methods disclosed herein, the target protein is tagged with one or more JAZ peptide tags as disclosed herein. JAZ peptide tags may be attached to a target protein using any methods known in the art. For example, in certain embodiments the peptide tag may be attached to the target protein prior to target protein expression. In these embodiments, a DNA sequence encoding the peptide tag is introduced into the host cell adjacent to the DNA sequence encoding the target protein, such that the peptide tag is expressed as part of the target protein. Methods for introducing a DNA sequence encoding a peptide tag into a cell and expressing a protein attached to the peptide tag are well known in the art. In other embodiments, the peptide tag may be attached to the target protein after the target protein has been expressed.

In certain embodiments of the methods disclosed herein, the target protein is tagged with a single peptide tag. In other embodiments, the target protein is tagged with two or more peptide tags. In those embodiments wherein the target protein is tagged with two or more peptide tags, the peptide tags may have the same or different sequences.

Previously developed targeted protein destruction systems have generally utilized chimeric mammalian F-box proteins. However, the methods disclosed herein utilize the *Arabidopsis* F-box protein COI1 or plant or moss homologs thereof. In certain embodiments, the methods disclosed herein utilize *Arabidopsis thaliana* or *Arabidopsis lyrata* COI1 comprising the amino acid sequence set forth in SEQ ID NOs: 15 and 16, respectively. Specific plant or moss homologs that may be utilized include those from rice (*Oryza sativa*, SEQ ID NO:17), tomato (*Solanum lycopersicum*, SEQ ID NO:18), grape (*Vitis vinifera*, SEQ ID NO:19), poplar (*Populus trichocarpa*, SEQ ID NO:20 and SEQ ID NO:21), castor oil (*Ricinus communis*, SEQ ID NO:22), corn (*Zea mays*, SEQ ID NO:23), rubber tree (*Hevea brasiliensis*, SEQ ID NO:24), pea (*Pisum sativum*, SEQ ID NO:25), wild tobacco (*Nicotiana attenuata*, SEQ ID NO:26), soybean (*Glycine max*, SEQ ID NO:27), sorghum (*Sorghum bicolor*, SEQ ID NO:28), wheat, or *Physcomitrella patens*. COI1 and its homologs are preferable to mammalian proteins because their high specificity for plant substrates minimizes competition and unwanted degradation of endogenous targets.

In certain embodiments, an *Arabidopsis* COI1 polypeptide or a homolog thereof may be introduced directly into a cell. In other embodiments, one or more genes encoding *Arabidopsis* COI1 or a homolog thereof may be introduced into a cell such that the cell expresses *Arabidopsis* COI1 or a homolog thereof. In these embodiments, the one or more genes encoding *Arabidopsis* COI1 or a homolog thereof may be introduced into a cell via any method known in the art, including transformation or transient or stable transfection using viral and non-viral vectors. In certain embodiments, the one or more genes may be introduced using a viral vector such as an adenoviral, retroviral, lentiviral, or baculoviral vector. Provided herein in certain embodiments are viral and non-viral vectors comprising a DNA sequence encoding *Arabidopsis* COI1 or a homolog thereof, as well as methods of using these vectors to achieve expression of *Arabidopsis* COI1 or a homolog thereof in a non-plant host cell. In certain embodiments, a DNA sequence encoding *Arabidopsis* COI1 or a homolog thereof may be incorporated into the host cell genome. In other embodiments, *Arabidopsis* COI1 or a homolog thereof may be expressed from a vector that is not incorporated into the host cell genome. The DNA sequence encoding *Arabidopsis* COI1 or a homolog thereof can be placed under the control of an endogenous promoter that is naturally present in a host cell, or it may be placed under the control of an exogenous promoter that has been introduced into the cell in conjunction with the COI1 or homolog sequence. In certain embodiments, *Arabidopsis* COI1 or a homolog thereof may be constitutively expressed in the host cell. In other embodiments, *Arabidopsis* COI1 or a homolog thereof may be expressed in a regulated manner. In certain of these embodiments, the DNA sequence encoding COI1 or a homolog thereof may be placed under the control of an inducible promoter, such as a chemically-regulated promoter or physically-regulated promoter. In these embodiments, the inducible promoter may provide an additional layer of control over activation of targeted protein degradation.

In certain embodiments of the methods provided herein, *Arabidopsis* COI1 or a homolog thereof functions in conjunction with endogenous proteins to form a functional $SCF^{COI1}$ E3 ligase in the non-plant cell into which COI1 has been introduced. For example, exogenous COI1 that has been introduced into a cell may function in combination with endogenous SKP1 to form a functional E3 ligase. Since SKP1 is highly conserved among species, the resultant complex is expected to be functional in most non-plant cell types. Nonetheless, in certain embodiments, one or more DNA sequences encoding SKP1 or other E3 ligase or ubiquitin pathway components may be introduced into a cell along with the one or more genes encoding *Arabidopsis* COI1 or homologs thereof. These other DNA sequences may be incorporated as part of the same vector as *Arabidopsis* COI1 or a homolog thereof, or they may be introduced via one or more separate vectors.

In certain embodiments, one or more modifications may be incorporated into *Arabidopsis* COI1 or a homolog thereof to enhance the interaction between COI1 or a homolog thereof and endogenous E3 ligase or other ubiquitin pathway proteins. These modifications may include one or more additions, substitutions, or deletions to the encoded COI1 or homolog sequence. Modifications may also include the addition of one or more peptide tags or the introduction of one or more covalent or non-covalent modifications.

In the methods disclosed herein, a molecule that binds the COI1/JA-Ile binding pocket of COI1 modulates the interaction between *Arabidopsis* COI1 or a homolog thereof and a target protein tagged with a JAZ peptide tag. In certain embodiments, the peptide tag will only bind *Arabidopsis* COI1 or a homolog thereof in the presence of the molecule that binds the COI1/JA-Ile binding pocket of COI1. In other embodiments, the peptide tag may bind *Arabidopsis* COI1 or a homolog thereof with very low affinity in the absence of the molecule, but do so with a significantly higher affinity in the presence of the molecule. The addition to or removal of the molecule that binds the COI1/JA-Ile binding pocket of COI1 from a cell provides a precise mechanism whereby targeted protein degradation can be turned on and off. For example, coronatine can be introduced into a cell to induce specific degradation, then withdrawn to halt degradation. Thus, the methods provided herein allow for precise temporal control of target protein degradation.

A molecule that binds the COI1/JA-Ile binding pocket of COI1 may be introduced into a cell and/or animal via any administration pathway known in the art. For example, the molecule can be administered to a whole animal model via oral or parenteral administration routes. Introduction of the molecule into a host cell may be carried out via a single administration or via multiple administrations over a set time period. In certain embodiments, the molecule may be steadily administered to a host cell or animal over a set period of time. Withdrawal of the molecule from the host cell may occur via natural degradation of the molecule or by active removal or deactivation, such as by introduction of a neutralizing molecule that degrades or inactivates the molecule.

The methods and compositions disclosed herein may be utilized for targeted protein degradation in any non-plant host cell, including for example eukaryotic cells such as yeast or mammalian cells. Accordingly, provided herein in certain embodiments are non-plant host cells comprising DNA sequences encoding a target protein, a JAZ peptide tag, and *Arabidopsis* COI1 or a homolog thereof. Also provided herein are cell culture systems comprising such non-plant host cells.

The methods and compositions disclosed herein may also be utilized for targeted protein degradation in whole animals and animal models. Therefore, in certain embodiments these animals and animal models are also provided herein. In certain embodiments, the animal model is a mammalian animal model, and in certain of these embodiments the mammal is a rat or mouse, such as for example a knockout mouse model.

A target protein to be tagged for degradation using the compositions and methods disclosed herein may be an endogenous host cell protein. Alternatively, the target protein may be an exogenous protein that has been stably or transiently introduced into the host cell. In those embodiments of the methods disclosed herein where the methods are carried out in an animal model and wherein the target protein is an exogenous protein, DNA sequences encoding the target protein, peptide tag, and *Arabidopsis* COI1 or a homolog thereof may be introduced into the animal using standard protein knockout methods known in the art. For example, the DNA sequences may be introduced into an embryonic stem cell under the control of one or more exogenous or endogenous promoters. This stem cell may be introduced into animal blastocysts, followed by selection for progeny that are homozygous for the introduction. Alternatively, the DNA sequences may be introduced into the animal at a later stage via one or more non-plant cells comprising each of these DNA sequences or by direct transfection of one or more animal cells. In those embodiments wherein the methods are carried out in an animal model and the target protein is an endogenous protein, DNA sequences encoding the peptide tag and *Arabidopsis* COI1 or a homolog thereof may be introduced into the animal by transfection of one or more animal cells. In these embodiments, the DNA sequence encoding the peptide tag is introduced in such a manner that is it is expressed as a fusion tag to the target protein.

In certain embodiments of the methods provided herein, targeted protein degradation is accomplished by the steps of 1) tagging a target protein with one or more peptide tags comprising, consisting of, or consisting essentially of an amino acid sequence selected from the group consisting of SEQ ID NOs:5, 6, 7, and 13, b) expressing the target protein in a non-plant host cell, c) expressing *Arabidopsis* protein COI1 or a homolog thereof in the host cell, and 4) introducing coronatine or a jasmonic acid-amino acid conjugate into the host cell, resulting in degradation of the target protein.

In certain embodiments of the methods provided herein, targeted protein degradation in a non-plant host cell is accomplished by the steps of 1) attaching a peptide tag comprising, consisting of, or consisting essentially of an amino acid sequence selected from the group consisting of SEQ ID NOs: 5, 6, 7, and 13 to a target protein, 2) introducing a DNA sequence encoding *Arabidopsis* COI1 or a homolog thereof into the host cell, 3) culturing the host cell under conditions that result in the expression of *Arabidopsis* COI1 or a homolog thereof, and 4) introducing coronatine or a jasmonic acid-amino acid conjugate into the host cell, resulting in degradation of the target protein.

In certain embodiments, kits are provided for carrying out targeted protein degradation in a non-plant host cell. In certain embodiments, these kits comprise one or more of the following components: an isolated nucleic acid encoding a JAZ peptide tag as disclosed herein, an isolated nucleic acid encoding *Arabidopsis* COI1 or a homolog thereof, a molecule that binds to the coronatine/JA-Ile binding pocket of COI1, and/or an inositol pentakisphosphate cofactor. In certain embodiments, the kit may further comprise a target protein or an isolated nucleic acid encoding a target protein. In certain embodiments, these kits further comprise instructions for usage.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Effect of Coronatine on COI1 Binding to JAZ1 and JAZ6

Various radioligand binding experiments were performed to quantify the interaction between tritium ($^3$H)-labeled coronatine and COI1/JAZ1 or COI1/JAZ6.

($^3$H)-labeled coronatine was synthesized by Amersham. Full-length *Arabidopsis thaliana* COI1 and ASK1 were co-expressed as a glutathione S-transferase (GST) fusion protein and an untagged protein, respectively, in Hi5 suspension insect cells. The COI1/ASK1 complex was isolated from the soluble cell lysate by glutathione affinity chromatography. After on-column tag cleavage by tobacco etch virus protease, the complex was further purified by anion exchange and gel filtration chromatography and concentrated by ultrafiltration to 12-18 mg ml$^{-1}$. Full-length JAZ substrate proteins were expressed as 6×His-fusion proteins in *Escherichia coli* and purified on Ni-NTA resin with subsequent dialysis into 20 mM Tris-HCl, pH 8.0, 200 mM NaCl, and 10% glycerol.

Radioligand binding was assayed on purified proteins, with 2 mg COI1/ASK1 complex and JAZ proteins at a 1:3 molar ratio. Reactions were prepared in 100 ml final volume and in a binding buffer containing 20 mM Tris-HCl 200 mM NaCl, and 10% glycerol. Saturation binding experiments were conducted with serial dilutions of 3H-coronatine in binding buffer. Nonspecific binding was determined in the presence of 300 mM coronatine. Competition binding experiments were conducted with serial dilutions of JA-Ile in the presence of 100 nM $^3$H coronatine with nonspecific binding determined in the presence of 300 mM coronatine. Total binding was determined in the presence of vehicle only. Two-point binding experiments were performed in the presence of 100 nM or 300 nM $^3$H-coronatine with nonspecific binding determined in the presence of 300 mM coronatine. Following incubation with mixing at 4° C., all samples were collected with a cell harvester (Brandel, Gaithersburg, Md.) on polyethyleneimine (Sigma)-treated filters. Samples were incubated in liquid scintillation fluid for >1 hour before counting with a Packard Tri-Carb 2200 CA liquid scintillation analyzer (Packard Instrument Co.). Saturation binding experiments were analyzed by nonlinear regression, competition binding experiments by nonlinear regression with $K_i$ calculation as described previously (Cheng 1973), and concentration-response data by sigmoidal dose-response curve fitting, all using GraphPad Prism version 4.00 for MacOSX.

Figure 2:
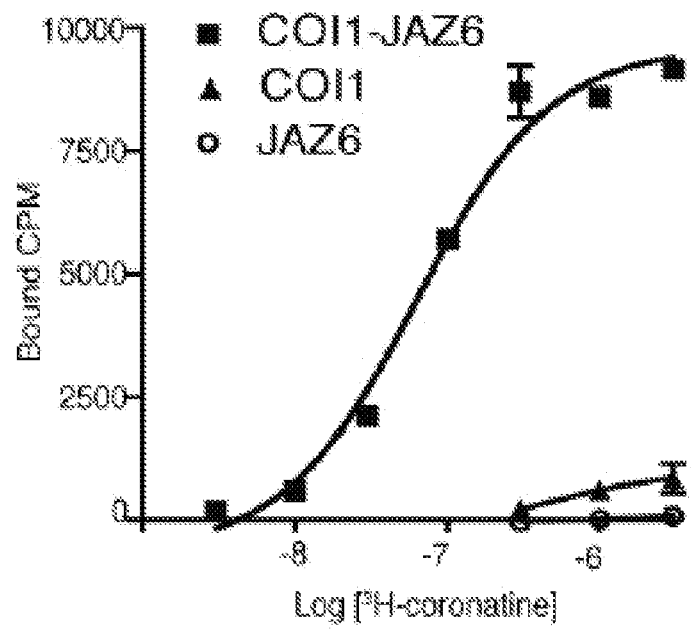
FIG. 2: A. Saturation binding of $^3$H-coronatine (up to 3 μM) to the COI1/JAZ6 complex, isolated COI1, and isolated JAZ6. B. Competition binding of 100 nM $^3$H—COR with (3R,7S)-JA-Ile and (3R,7R)-JA-Ile at a $K_i$ of 1.8±0.6 μM and 18±19 μM, respectively.
Figure 2:
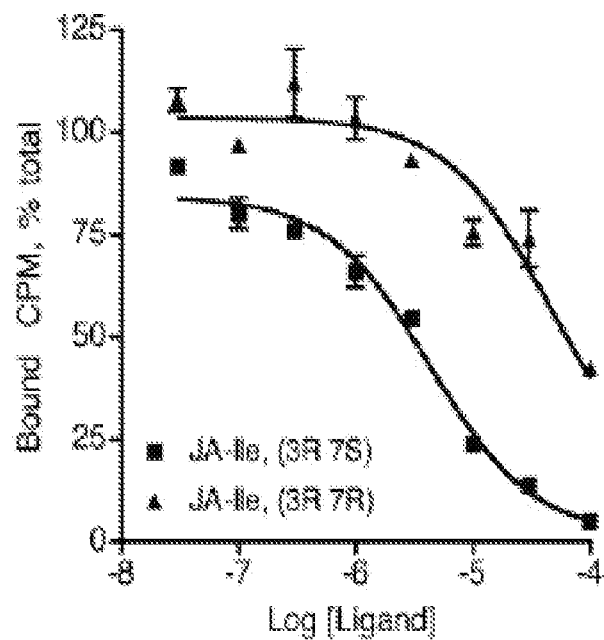

$^3$H-coronatine showed no appreciable binding affinity for COI1, full-length JAZ1, or full-length JAZ6 alone (FIG. 1A), but bound to the complex of COI1/JAZ1 with a $K_D$ of 48 nM and to the complex of COI1/JAZ6 with a $K_D$ of 68 nM (FIG. 1B). Binding of coronatine to the COI1/JAZ6 complex reached the level of saturation at 300 nM. Binding to COI1 alone at the same concentration elicited <2% specific binding (FIG. 2A). The highly active (3R,7S) isomer of JA-Ile was found to compete with coronatine for binding to the COI1-JAZ6 complex with an inhibition constant ($K_i$) of 1.8 μM, while the less active (3R,7R) isomer competed with a $K_i$ of 18 μM (FIG. 2B).

These results show that the COI1/JAZ complex, rather than COI1 alone, functions as the genuine high-affinity jasmonate receptor in a co-receptor form.

Example 2

Characterization of JAZ1 Peptides

The COI1-binding region of the JAZ proteins has previously been mapped to the carboxy-terminal Jas motif, which is characterized by the SLXXFXXKRXXRXXXXXPY consensus sequence (SEQ ID NO:30) preceded by two consecutive basic residues. As shown in Example 1, mutation of the conserved phenylalanine residue to alanine is sufficient to abolish the high affinity interaction between coronatine and COI1/JAZ6 (FIG. 1A).

Figure 3:
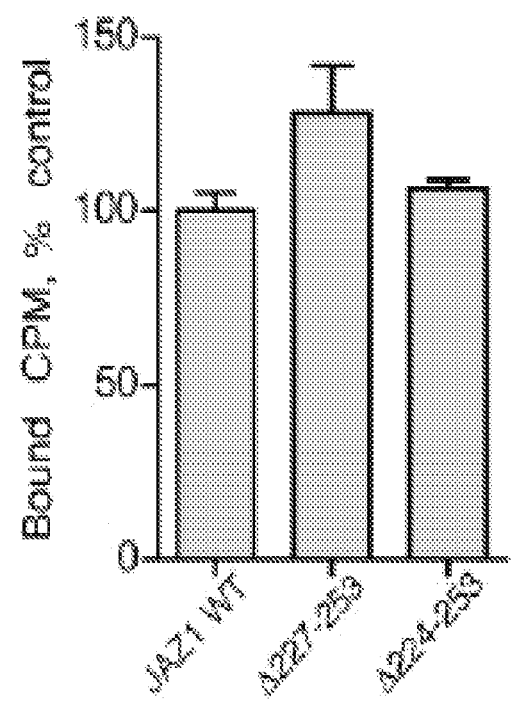
FIG. 3: Binding of 300 nM $^3$H—COR to JAZ1 proteins truncated immediately after (Δ227-253) or before (Δ224-253) the PY motif.

Previous studies have shown that the highly conserved PY sequence at the C-terminal end of the Jas motif plays a role in JAZ localization and stability in vivo, but that the sequence was not necessary for ligand-dependent COI1-JAZ interaction. This was confirmed by an experiment showing that truncation of the PY motif in JAZ1 had little effect on in vitro ligand binding activity (FIG. 3). To further map the minimal region of the Jas motif required for high affinity ligand binding with COI1, the recombinant JAZ1 protein was replaced with a set of synthetic JAZ1 peptides in a ligand binding assay.

Figure 4:
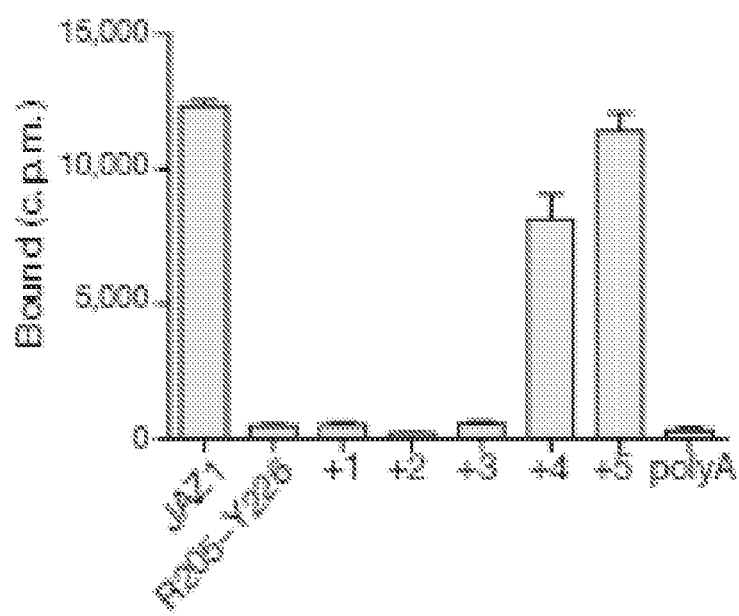
FIG. 4: Binding of 300 nM coronatine to COI1 in the presence of various JAZ1 degron derivative peptides with systematic N-terminal extensions.

The JAZ1 degron of SEQ ID NO:1 (R205-Y226), which spans the central conserved Jas motif plus the two additional amino-terminal basic residues, did not bind to COI1 with high affinity in the presence of coronatine (FIG. 4). These results indicate that residues N-terminal to Arg205 must participate in the COI1/JAZ interaction. Various derivatives of the JAZ1 degron sequence, as well as derivatives of the JAZ6 and JAZ7 degron sequences, were analyzed for their ability to bind COI1 with high affinity in the presence of coronatine. These derivatives are set forth in Table 1.

TABLE 1

| Peptide | SEQ ID NO | Sequence |
|---|---|---|
| JAZ1 Jas motif |  | PIARRASLHRFLEKRKDRVTSKAPY |
| JAZ1 degron | 1 | RRASLHRFLEKRKDRVTSKAPY |
| JAZ1 + 1 extension | 2 | ARRASLHRFLEKRKDRV |
| JAZ1 + 2 extension | 3 | IARRASLHRFLEKRKDRV |
| JAZ1 + 3 extension | 4 | PIARRASLHRFLEKRKDRV |
| JAZ1 + 4 extension | 5 | LPIARRASLHRFLEKRKDRV |
| JAZ1 + 5 extension | 6 | ELPIARRASLHRFLEKRKDRV |
| JAZ1 + 5 extension + PY motif | 7 | ELPIARRASLHRFLEKRKDRVTSKAPY |
| JAZ1 + polyA extension | 8 | AAAAARRASLHRFLEKRKDRV |
| JAZ1 + 5 extension from JAZ6 | 9 | VERIARRASLHRFLEKRKDRV |
| JAZ6 + 5 extension | 10 | VERIARRASLHRFFAKRKDRV |

TABLE 1-continued

| Peptide | SEQ ID NO | Sequence |
|---|---|---|
| JAZ6 + 10 extension | 11 | QQHQVVERIARRASLHRFFAKRKDRV |
| JAZ7 + 5 extension | 12 | YQKASMKRSLHSFLQKRSLRI |

The JAZ1 +1, +2, +3, +4, and +5 extensions (SEQ ID NOs:2-6, respectively) added on 1, 2, 3, 4, and 5 residues, respectively, to the N-terminus of JAZ1 while removing six residues from the C-terminus. The added residues were derived from the residues that are normally present N-terminal to the degron in JAZ1. An additional JAZ1 peptide (SEQ ID NO:7) contained the same additional N-terminal amino acids as the +5 extension but with the six C-terminal residues added back on.

Figure 5:
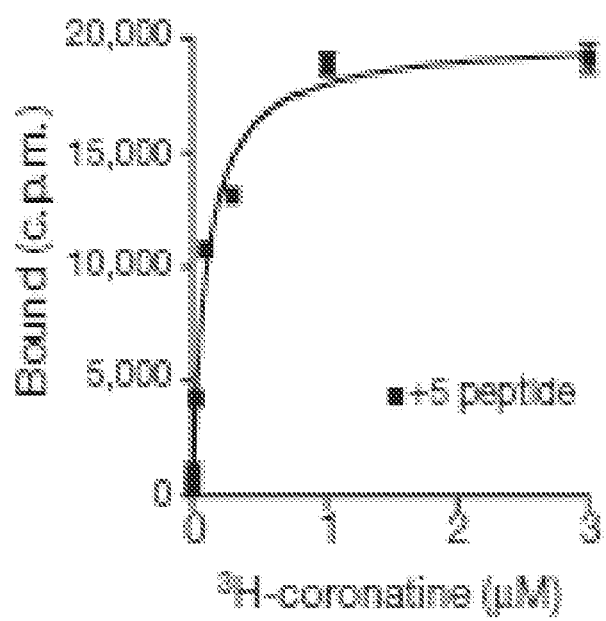
FIG. 5: Saturation binding of COI1/ASK1 and the JAZ1 degron +5 peptide. The peptide bound COI1 with a $K_D$ of 108±29 nM.
Figure 6:
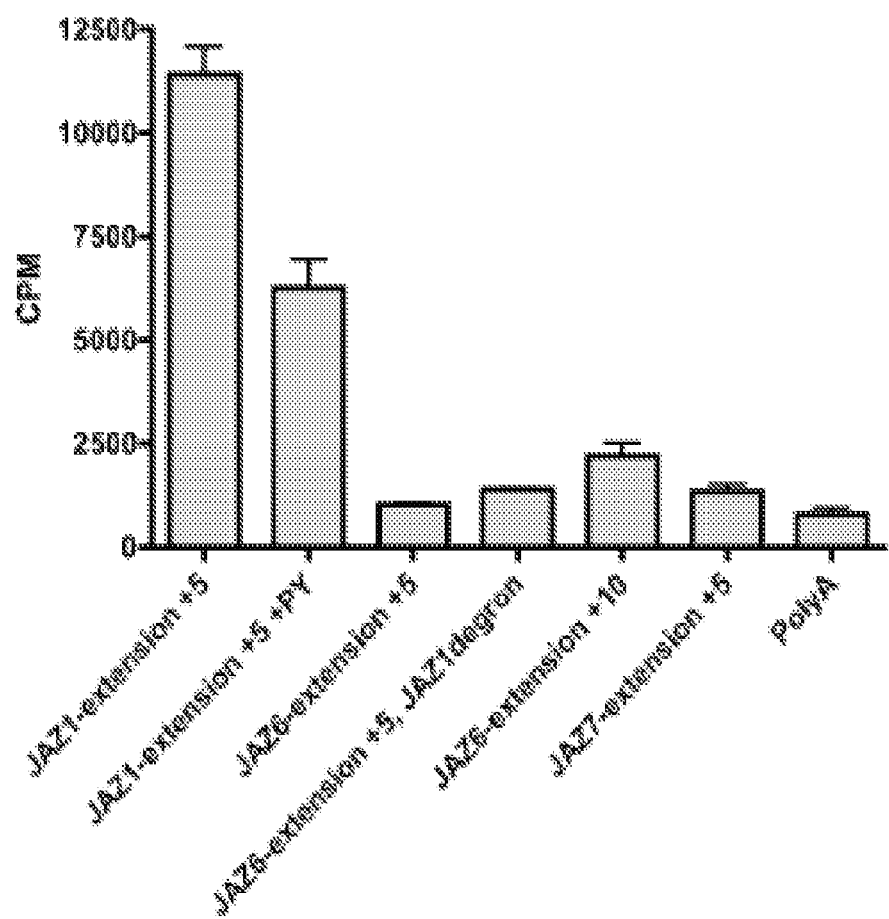
FIG. 6: Binding of coronatine to COI1 in the presence of various JAZ1 degron derivative peptides.

The JAZ1 +4 and +5 extensions (SEQ ID NOs:5 and 6, respectively) were found to bind COI1 in the presence of coronatine with a much higher affinity than the JAZ1 degron and the +1, +2, and +3 extensions, with the +5 extension exhibiting the highest degree of binding (FIG. 4). The JAZ1 +5 extension peptide was found to permit coronatine binding with a $K_D$ (~108 nM) comparable to that of the full-length JAZ1 protein (FIG. 5). The JAZ1 +5 extension with the six C-terminal residues added back on also exhibited significant binding (FIG. 6, "JAZ1-extension +5+PY").

To test the specificity of the JAZ1 peptide tags of SEQ ID NOs:5, 6, and 7, an additional set of JAZ peptide tags was developed. The first two were essentially identical to the JAZ1 +5 extension in that they contained residues 1-16 of the JAZ1 degron plus a five amino acid N-terminal extension. However, the sequence of the extension was different. The first of these (SEQ ID NO:8) utilized a polyalanine extension, while the second (SEQ ID NO:9) utilized a five amino acid extension derived from JAZ6. The remaining JAZ peptide tags were based on the degrons of JAZ6 and JAZ7. These included two JAZ6 peptides that contained the JAZ6 degron plus an additional five and ten N-terminal residues, respectively (SEQ ID NOs: 10 and 11, respectively) and one JAZ7 peptide that contained the JAZ7 degron plus an additional five N-terminal residues (SEQ ID NO: 12). None of the additional JAZ peptide tags exhibited significant binding to COI1 in the presence of coronatine (FIGS. 4 and 6). These results suggest that the system disclosed herein maintains a great deal of selectivity for side chain chemistry, and that simply inserting five "filler" amino acid residues at the N-terminus of the peptide tag is insufficient to promote COI1 binding.

Example 3

Structural Relationship of COI1/JAZ1 and Coronatine

To evaluate the structure mechanism by which COI1/JAZ1 co-receptor senses jasmonate, crystal structures were obtained for COI1/ASK1/JAZ1 peptides complexed with either coronatine or (3R,7S)-JA-Ile.

Crystals were grown at 4° C. by the hanging-drop vapor diffusion method with 1.5 µL protein complex samples containing COI1/ASK1, JAZ1 peptide, and hormone compound at 1:1:1 molar ratio mixed with an equal volume of reservoir solution containing 100 mM BTP, 1.7-1.9 M ammonium phosphate, and 100 mM NaCl, pH 7.0. Diffraction quality crystals were obtained by the micro-seeding method at 4° C.

The crystals all contained eight copies of the complex in the asymmetric unit. The data sets were collected at the Advanced Light Source in Lawrence Berkeley National Laboratory as well as the GM/CA-CAT 23 ID-B beamline at the Advanced Photon Source in Argonne National Laboratory using crystals flash-frozen in the crystallization buffers supplemented with 15-20% ethylene glycol at −170° C. Reflection data were indexed, integrated, and scaled with the HKL2000 package. All crystal structures were solved by molecular replacement using the program Phaser and the TIR1/ASK1 structure as search model. The structural models were manually built in the program O and refined using CNS and PHENIX. All final models had 96-98% of residues in the favored region and 0% in disallowed region of the Ramachandran plot.

Figure 10:
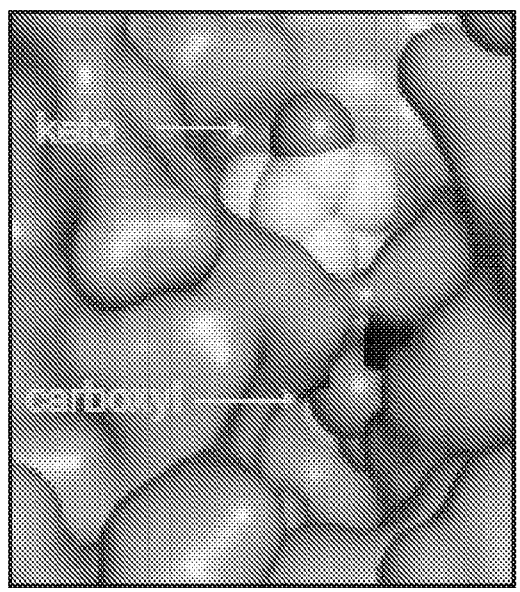
FIG. 10: When bound to COI1, JA-Ile (yellow space fill) is solvent accessible at both the keto group (top) and carboxyl group (bottom).
Figure 11:
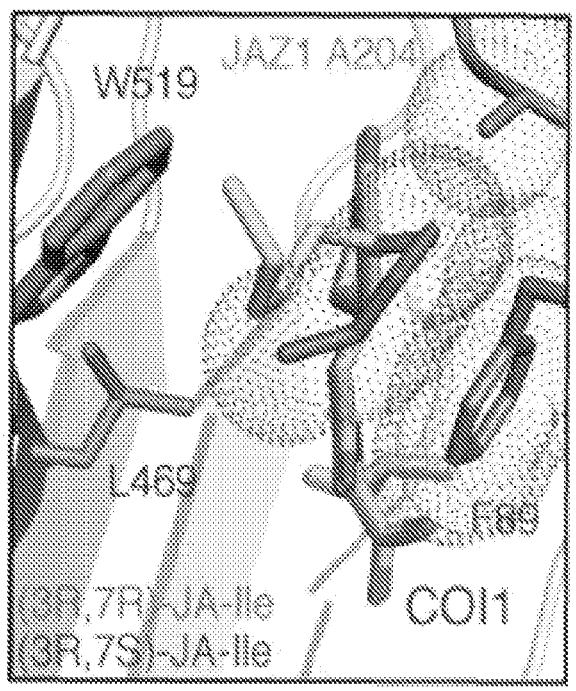
FIG. 11: A. Side view of the COI1 pocket accommodating the pentenyl side chain of (3R,7S)-JA-Ile (yellow stick). The pentenyl side chain of (3R,7R)-JA-Ile (magenta stick) is modeled on the structure of (3R,7S)-JA-Ile and rotated around the C7-C8 bond to minimize collision with JAZ1 Ala 204 and COI1 Phe 89. The electron clouds of nearby COI1 (green) and JAZ1 (orange) side chains, as well as the pentenyl side chain of (3R,7R)-JA-Ile (magenta) are shown in dot form. Ala 86 and Leu 91 of COI1 blocking the front view of the pocket are omitted for clarity. B. Side view of (3R,7S)-JA-Ile (yellow stick) and coronatine (cyan stick) showing a hydrophobic pocket that accommodates both the aliphatic isoleucine portion of JA-Ile and the cyclopropane ring of coronatine.
Figure 11:
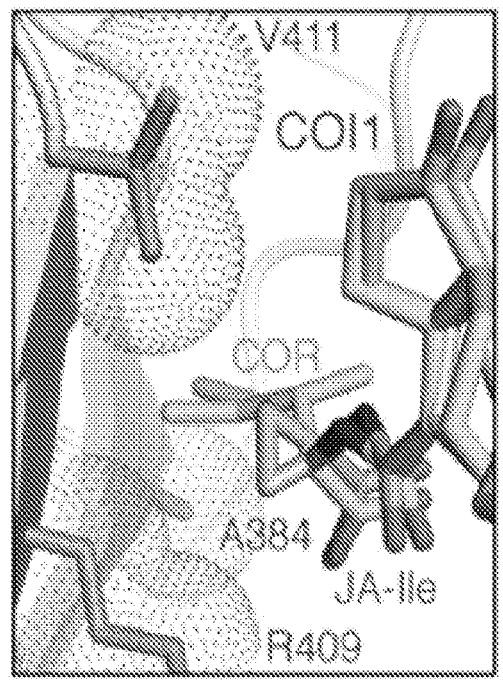

Without the JAZ degron peptide bound, the keto group of the ligand is accessible to solvent (FIG. 10). The rest of the cyclopentanone ring of both JA-Ile and coronatine is sandwiched between the aromatic groups of F89 and Y444 of COI1, stabilized by hydrophobic packing. The cyclohexene ring of coronatine provides a rigid surface area for close packing with F89, whereas the more flexible and extended pentenyl side chain of JA-Ile is more loosely accommodated by a hydrophobic pocket formed by A86, F89 and L91 from loop 2 as well as L469 and W519 from the LRRs (FIG. 11A). Differences at this interface probably explain the approximately tenfold higher affinity of coronatine over (3R,7S)-JA-Ile detected in binding assays. Deeper in the ligand-binding pocket, the common amide and carboxyl groups of JA-Ile and

TABLE 2

|  | COI1/ASK1/JAZ1 degron/coronatine | COI1/ASK1/JAZ1 +5 extension/ coronatine | COI1/ASK1/JAZ1 +5 extension/JA-Ile |
|---|---|---|---|
| Data collection | | | |
| Space group | P21 | P21 | P21 |
| Cell dimensions a, b, c (Å) | 121.8, 221.5, 148.5 | 123.2, 220.8, 149.5 | 122.3, 220.8, 148.7 |
| α, β, γ (°) | 90.0, 104.5, 90.0 | 90.0, 104.5, 90.0 | 90.0, 104.5, 90.0 |
| Resolution (Å) | 2.80 (2.80-2.90) | 3.35 (3.35-3.41) | 3.18 (3.18-3.31) |
| $R_{sym}$ | 0.103 (0.816) | 0.119 (0.700) | 0.088 (0.462) |
| $I/\sigma I$ | 16.7 (2.0) | 14.0 (2.1) | 17.2 (2.8) |
| Completeness (%) | 100 (100) | 92.9 (94.6) | 97.0 (93.3) |
| Redundancy | 3.9 (3.8) | 3.6 (3.3) | 3.1 (2.7) |
| Refinement | | | |
| Resolution (Å) | 50-2.80 | 50-3.35 | 50-3.18 |
| No. reflections | 174,966 | 95,997 | 116,337 |
| $R_{work}/R_{free}$ | 0.235/0.270 | 0.225/0.270 | 0.223/0.264 |
| R.m.s deviations Bond lengths (Å) | 0.008 | 0.010 | 0.010 |
| Bond angles (°) | 1.676 | 1.271 | 1.556 |

Figure 7:
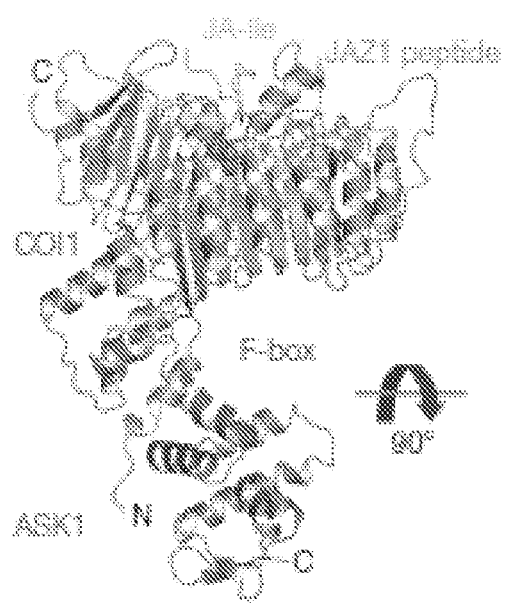
FIG. 7: A, B. Structure of *Arabidopsis* COI1 (green ribbon)/Ask1 receptor protein (grey ribbon) complex bound to JAZ1 degron peptide (orange ribbon) and (3R,7S)-JA-Ile in yellow space fill representation. C. Surface representation of COI1 (grey) with loop 2 (blue), loop 12 (purple), and loop 14 (green) forming the JA-Ile binding pocket.
Figure 7:
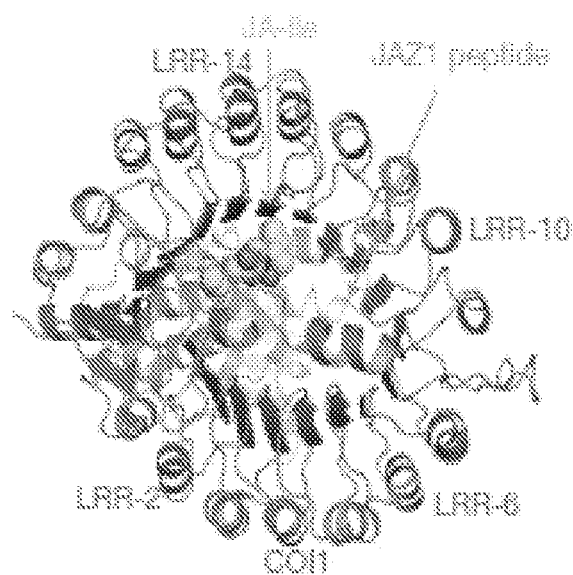
Figure 7:
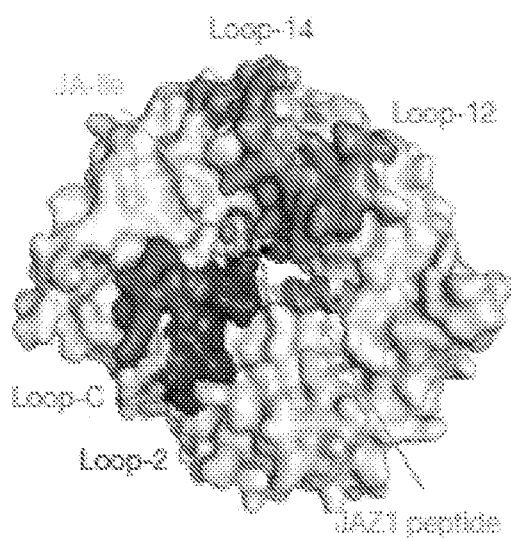

The crystal structure of COI1 revealed a TIR1-like overall architecture, with the N-terminal tri-helical F-box motif bound to ASK1 and a C-terminal horseshoe-shaped solenoid domain formed by 18 tandem leucine-rich repeats (FIGS. 7A and 7B). Similar to TIR1, the top surface of the COI1 leucine-rich repeat (LRR) domain has three long intra-repeat loops (loops 2, 12, and 14) that are involved in hormone and polypeptide substrate binding. Unlike TIR1, however, a fourth long loop (loop C) in the C-terminal capping sequence of the COI1 LRR domain folds over loop 2, partially covering it from above (FIGS. 7B and 7C).

Figure 8:
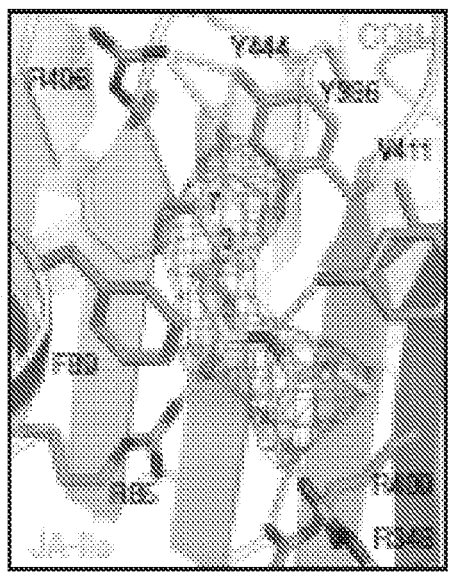
FIG. 8: A, B. Side view of JA-Ile and COR binding. Hormones are shown as stick models, along with positive $F_o$–$F_c$ electron density, calculated before they were built into the model (red mesh). Hydrogen bond and salt bridge networks are shown with yellow dashes. C. Top view of the JA-Ile pocket showing the $F_o$–$F_c$ electron density, calculated before JA-Ile was built into the model (red mesh). The electron density of the pentenyl side chain of (3R,7S)-JA-Ile cannot accommodate the (3R,7R)-JA-Ile side chain, which is constrained by the chiral configuration at the C7 position.
Figure 8:
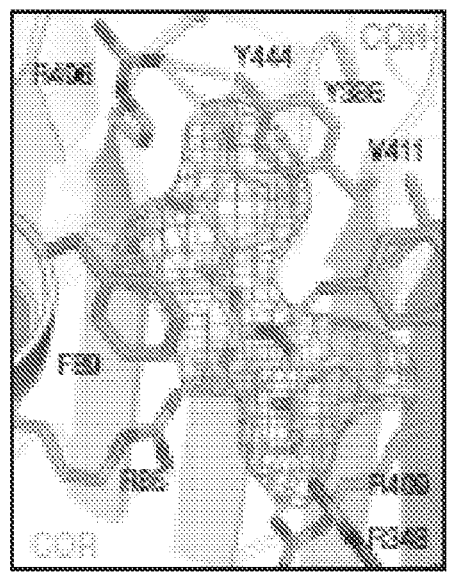
Figure 8:
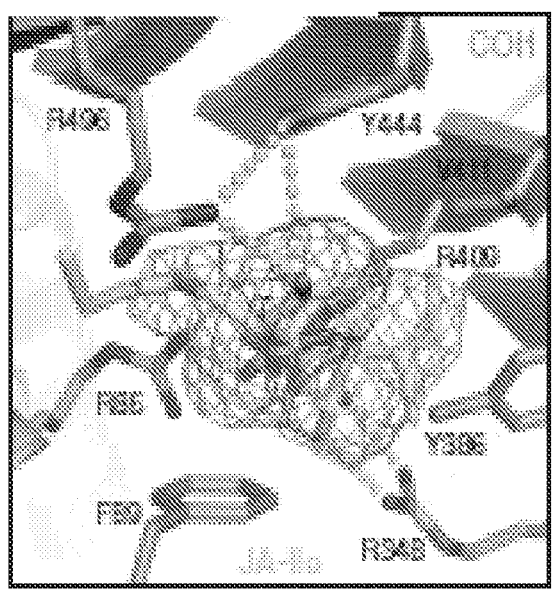
Figure 9:
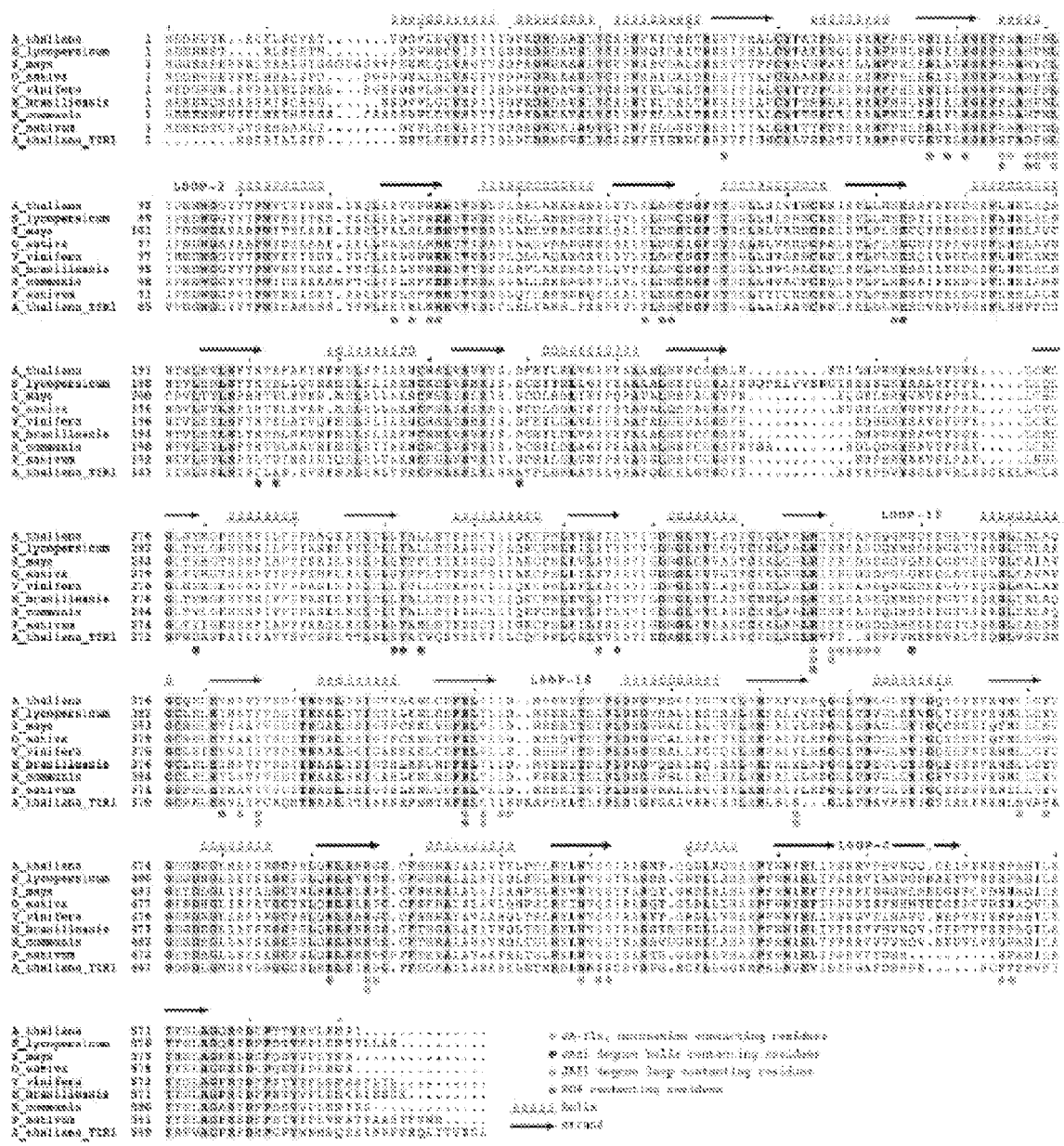
FIG. 9: Alignment of *Arabidopsis thaliana* TIR1 (SEQ ID NO:31) and various COI1 orthologs from select plant species (*Arabidopsis thaliana*, SEQ ID NO:15; *Solanum lycopersicum*, SEQ ID NO:18; *Zea mays*, SEQ ID NO:23; *Oryza sativa*, SEQ ID NO:17; *Vitis vinifera*, SEQ ID NO:19; *Hevea brasiliensis*, SEQ ID NO:24; *Ricinus communis*, SEQ ID NO:22; *Pisum sativum*, SEQ ID NO:25). Secondary structure elements as determined in the crystal structure of the COI1/ASK1/JAZ1 degron peptide/JA-Ile complex are shown on top of the *Arabidopsis thaliana* COI1 sequence. Critical ligand-, phosphate-, and substrate-contacting residues are indicated by colored dots as described in the key.

Despite their similar overall fold, crystal structure analysis revealed that COI1 has evolved a hormone binding site that is distinct from that of TIR1. Configured between loop 2 and the inner wall of the LRR, the ligand binding pocket of COI1 is exclusively encircled by amino acid side chains (FIG. 8). Many of the pocket-forming residues on COI1 are large in size and carry a polar head group (FIG. 9). These properties allow them to be mold a binding pocket into a specific shape while forming close interactions with each chemical moiety of the ligand. These close interactions are critical to proper hormone sensing of the complex. In the binding pocket, both JA-Ile and coronatine sit in an 'upright' position with the keto group of their common cyclopentanone ring pointing up and forming a triangular hydrogen bond network with R496 and Y444 of COI1 at the pocket entrance (FIG. 8).

coronatine bind to the bottom of the binding site by forming a salt bridge and hydrogen bond network with three basic residues of COI1:R85, R348 and R409 (FIGS. 8A and 8B). Together, these arginine residues constitute the charged floor of the ligand pocket. Y386 reinforces the interactions from above by forming a hydrogen bond with the amine group of the ligand. In doing so, Y386 approaches the cyclopentanone ring of the ligand, narrowing the pocket entrance and creating a hydrophobic cave below. The rest of the basin is carved out by V411, A384 and the aliphatic side chain of Arg 409 (FIG. 11B). The ethyl-cyclopropane group of coronatine and the isoleucine side chain of JA-Ile can both comfortably fit in this space due to their similar size and hydrophobicity. The nature of the cave explains the preference of COI1 for jasmonate conjugates containing a moderately sized hydrophobic amino acid. Although most of the ligand is buried inside the binding site, the keto group at the top and the carboxyl group at the bottom remain exposed, available for additional interactions with the JAZ portion of the co-receptor (FIG. 10).

Figure 12:
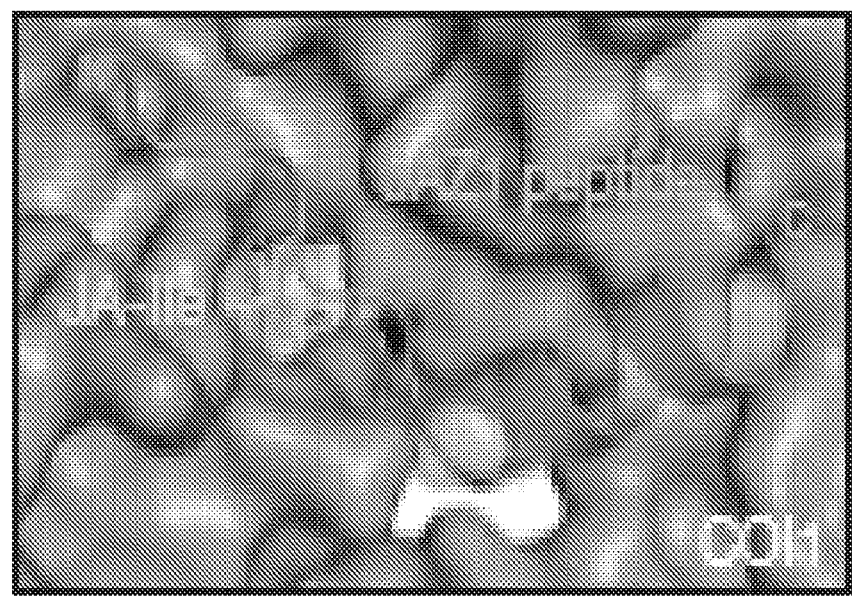
FIG. 12: A. Top view of the complete JAZ1 degron peptide (orange) bound to COI1 (green) and JA-Ile (yellow). B. Side view and surface representation of the JAZ peptide, which acts as a clamp to lock JA-Ile in the pocket.
Figure 12:
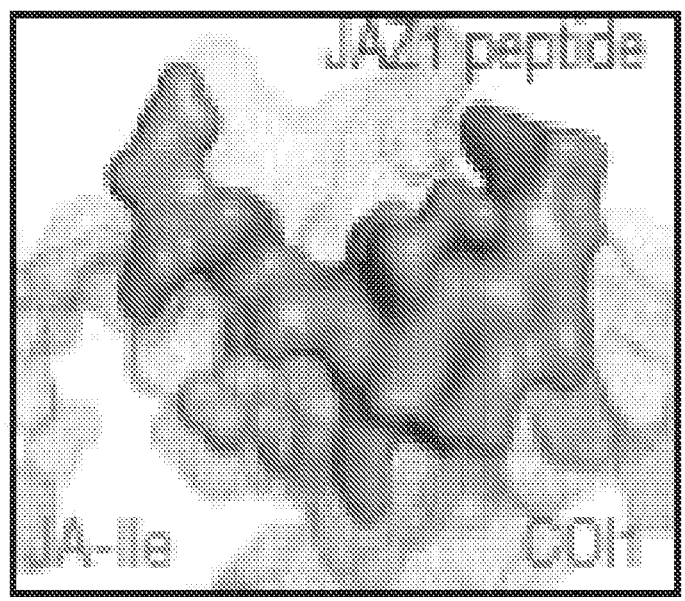

The JAZ1 degron peptide adopts a bipartite structure with a loop region followed by an α-helix to assemble with the COI1/JA complex. The hallmark of the JAZ1 degron is the N-terminal five amino acids identified in the radioligand binding assay. In a largely extended conformation, this short sequence lies on top of the hormone-binding pocket and simultaneously interacts with both COI1 and the ligand, effectively trapping the ligand in the pocket (FIGS. 12A and 12B). At the N-terminal end, L201 of the JAZ1 peptide is embedded in a hydrophobic cavity presented by surface loops on top of COI1 (FIG. 13A).

Figure 13:
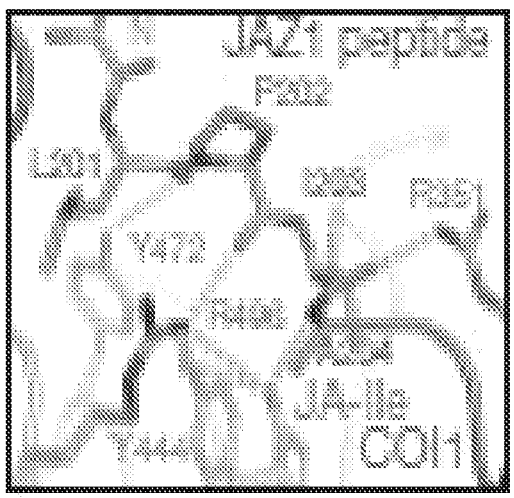
FIG. 13: A. Interactions of the N-terminal region of the JAZ1 degron with COI1 and JA-Ile. Hydrogen bonds are shown with yellow dashes. B. Structural role of the Arg 206 residue from the JAZ1 degron in coordinating the carboxyl group of JA-Ile with three basic residues of the COI1 ligand pocket floor. C. Top view of the amphipathic JAZ1 degron helix bound to COI1 with three hydrophobic residues of JAZ1 shown in stick representation (orange) and COI1 residues in colored surface representation.
Figure 13:
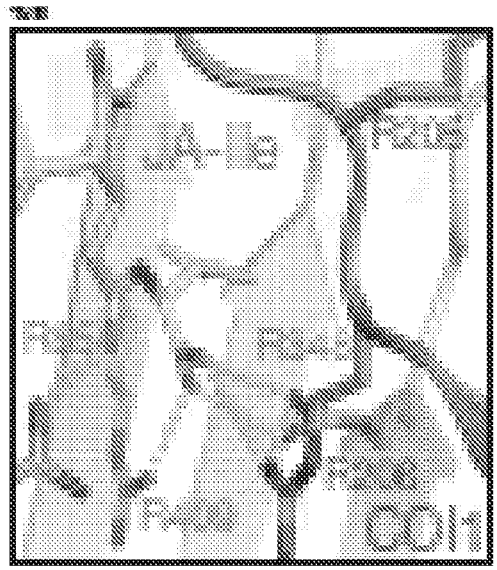
Figure 13:
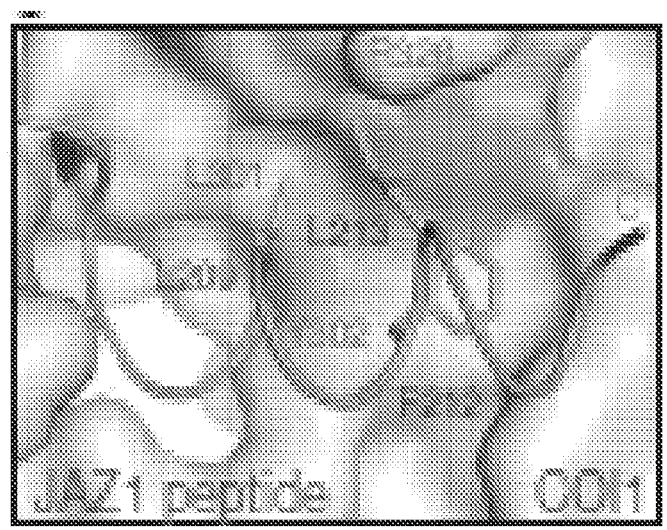

At the C-terminal end, A204 of JAZ1 uses its short side chain to pack against the keto group of the ligand and F89 of COI1 (FIGS. 11A and 13A). The same alanine residue of JAZ1 also donates a hydrogen bond through its backbone amide group to the keto moiety of the ligand emerging from the pocket (FIG. 13A). The middle region of the five-amino-acid sequence is secured to the COI1 jasmonate complex through a hydrogen bond formed between the backbone carbonyl of P202 in JAZ1 and the ligand-interacting COI1 residue R496, which is critical for the hormone-dependent COI1/JAZ interaction (data not shown). In agreement with its important role in forming the JA-Ile co-receptor, this short N-terminal region of the JAZ degron completely covers the opening of the ligand-binding pocket, conferring high-affinity binding to the hormone. The close interaction between the hormone and the co-receptor complex provides a plausible structural explanation for the favorable binding of the (3R, 7S)-JA-Ile isomer, as the stereochemistry at the 7 position of (3R,7R)-JA-Ile may place the aliphatic chain unfavorably close to nearby JAZ1 and COI1 residues (FIG. 11A).

Within the JAZ1 degron, two conserved basic residues, R205 and R206, were previously shown to have an important role in hormone-induced COI1 binding. In the structure, R205 contributes to COI1 binding by directly interacting with loop 12, whereas R206 points in the opposite direction and inserts deeply into the central tunnel of the COI1 solenoid. Approaching the bottom of the ligand-binding pocket, the guanidinium group of the R206 side chain joins the three basic COI1 residues that form the pocket floor and interacts directly with the carboxyl group of the ligand (FIG. 13B). Thus, the N-terminal seven amino acids (ELPIARR) of the JAZ1 degron peptide act as a clamp that wraps the ligand-binding pocket from top to bottom, closing it completely (FIG. 12B).

The highly conserved C-terminal half of the JAZ1 degron forms an amphipathic α-helix that strengthens the JAZ1/COI1 interaction by binding to the top surface of the COI1 LRR domain, adjacent to the ligand-binding site (FIG. 12A). With its N-terminal end directly packing against loop 2 of COI1, the Jas motif helix blocks the central tunnel of the COI1 LRR solenoid like a plug. The N-terminal half of the Jas motif helix is characterized by three hydrophobic residues (L209, F212 and L213) which are aligned on the same side of the helix and form a hydrophobic interface with COI1 (FIG. 13C).

By soaking the COI1-ASK1 crystals with coronatine and a sufficiently high concentration of JAZ1 degron peptide lacking the N-terminal ELPIA sequence, the complex formed by COI1, coronatine, and the isolated Jas motif helix was trapped in the crystal (Table 2). This indicates that the α-helix may provide a low-affinity anchor for docking the JAZ protein on COI1.

Example 4

Identification of COI1 Cofactor

The crystal structure of TIR1 revealed an unexpected inositol hexakisphosphate ($InsP_6$) molecule bound in the centre of the protein underneath the auxin-binding pocket. Sequence homology between COI1 and TIR1 suggests that COI1 might contain a similar small molecule. Before crystallization, the recombinant COI1/ASK1 complex was analyzed by structural mass spectrometry.

Nano-electrospray ionization mass spectrometry (MS) and tandem MS (MS/MS) experiments were performed on a SynaptHDMS instrument. Before MS analysis, 50 μL of a 16 mg ml$^{-1}$ solution of COI1/ASK1 in 20 mM Tris-HCl, pH 8, 0.2 M NaCl, and 5 mM DTT was buffer-exchanged twice into 0.5M ammonium acetate solution using Bio-Rad Biospin columns. To improve desolvation during ionization, samples were diluted 1:4 in 0.5 M ammonium acetate, and isopropanol was added to a final concentration of 5%. Typically an aliquot of 2 mL solution was loaded for sampling via nano-ESI capillaries, which were prepared in-house from borosilicate glass tubes as described previously (Nettleton 1998). The conditions within the mass spectrometer were adjusted to preserve non-covalent interactions. The following experimental parameters were used: capillary voltage up to 1.26 kV, sampling cone voltage 150 V, and extraction cone voltage 6 V, MCP 1590. For tandem MS experiments peaks centered at m/z 4,564 and 4,588 were selected in the quadrupole and collision energy up to 65 V was used. Argon was used as a collision gas at maximum pressure. All spectra were calibrated externally using a solution of cesium iodide (100 mg ml$^{-1}$). Spectra are shown with minimal smoothing and without background subtraction.

Figure 15:
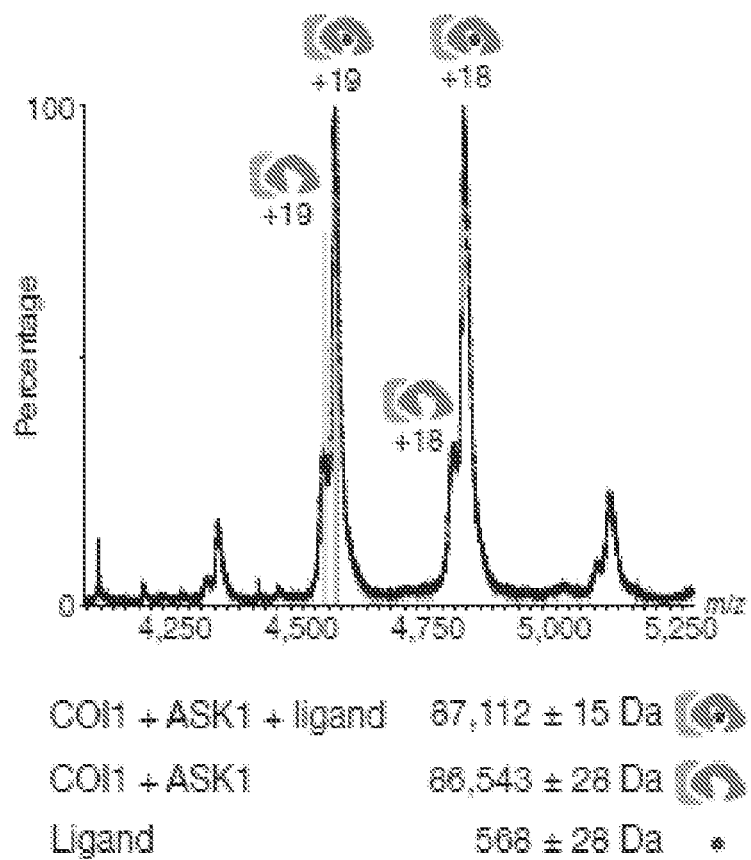
FIG. 15: Nano-electrospray mass spectrometry of the intact COI/ASK1 complex. Low-intensity charge series corresponds in mass to the cofactor-free COI1/ASK1 complex.
Figure 16:
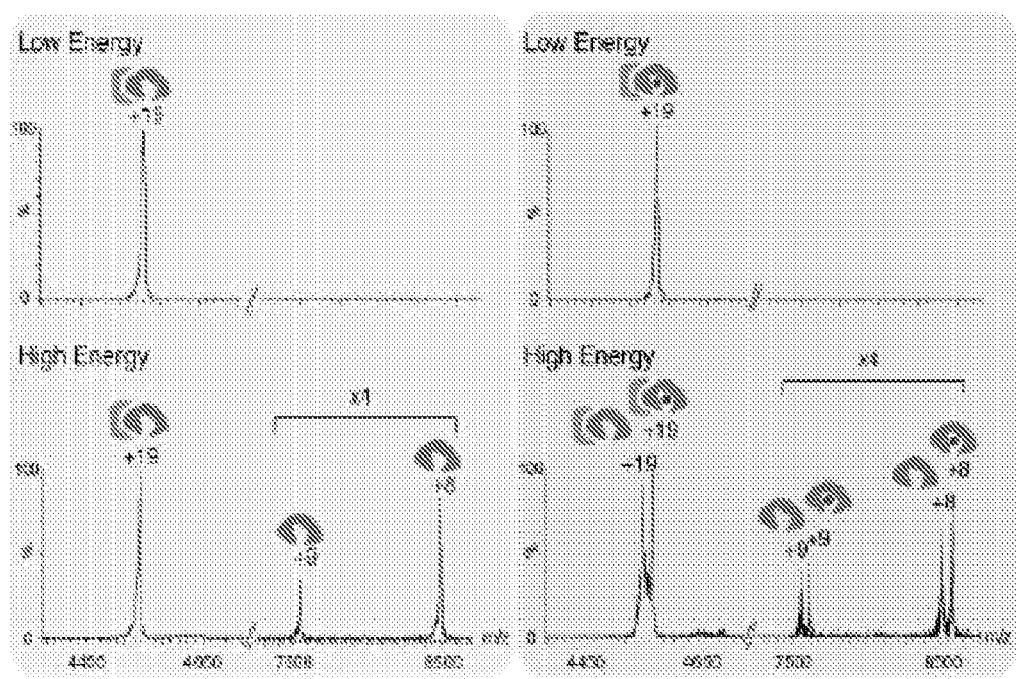
FIG. 16: Structural mass spectrometry analysis of the COI1/ASK1 complex. A. Isolation at 4564 m/z of the 19+ charge state for tandem MS analysis (shown in blue in FIG. 24). B. MS/MS spectrum showing the dissociation products of ions isolated at 4588 m/z (shown in orange in FIG. 24).

Nano-electrospray mass spectra of the intact COI1/ASK1 complex revealed two populations differing by a mass of ~568 Da, indicating that a small molecule was indeed co-purified with the proteins (FIGS. 15 and 16). As shown in FIG. 16, only one population of the complex corresponding to COI/ASK1 was apparent at both at low and high collision energy. At high collision energy, the COI/ASK1 complex dissociates into its different subunits and one population of COI1 appears in the spectrum. This population of COI1 has a calculated mass of 67,944±1 Da, which is in agreement with the theoretical mass of COI1 (67,947 Da). At low collision energy, the COI1/ASK1/ligand complex is apparent. However, elevating the collision energy releases some of the bound ligand and results in the appearance of a stripped COI1/ASK1 complex. The theoretical mass of the apo COI1/ASK1 complex is 86,458 Da, which is in close agreement with the observed mass of 86,543±28 Da. The mass of the COI1/ASK1/ligand complex was found to be 87,112±15 Da, suggesting that the mass of the ligand is around 568±28 Da. The fact that both masses carry a charge of +19 indicates a neutral loss of the ligand, meaning that it cannot be detected in the spectrum. At high collision energy, some of the complex dissociates into its different subunits and two populations of COI1 appear in the spectrum. The smaller form, with a calculated mass of 67,952±5 Da, fits the theoretical mass of COI1 (67,946.5 Da), whereas the other population, with a calculated mass of 68,518±4 Da, corresponding to COI1-ligand, suggest that the mass of the ligand is around 568±5 Da.

The mass-spectrometry-derived molecular mass of the unknown compound is different from the mass of $nsP_6$ (651 Da) but matches that of an inositol pentakisphosphate ($InsP_5$) molecule. Unfortunately, mass spectrometry analyses of either the native COI1/ASK1 complex or the denatured proteins were unable to achieve direct mass analysis of the small molecule.

Figure 17:
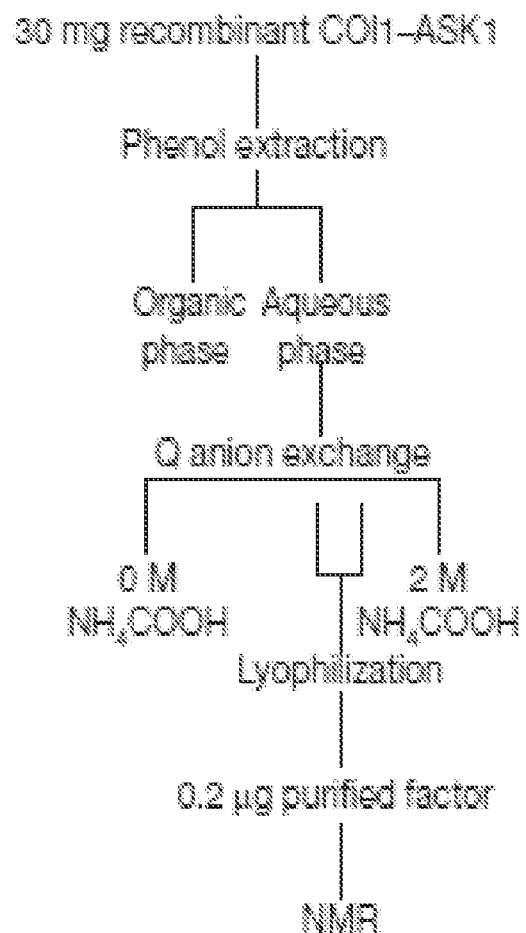
FIG. 17: Optimized cofactor purification scheme.

To investigate the identity of the unknown compound, it was first estimated that the molecule contains four or five phosphate groups by $^{31}P$ nuclear magnetic resonance (NMR) of trypsin-digested COI1/ASK1 complex (data not shown). To identify unequivocally the unknown molecule, steps were taken to purify it away from the COI1/ASK1 complex in a quantity sufficient for $^1$H NMR analysis. The high phosphate content of the molecule allowed us to trace it through a multi-step purification procedure (FIG. 17). Phenol was melted at 68° C. and equilibrated with equal parts 0.5 M Tris-HCl, pH 8.0 until a pH of 7.8 was reached. The equilibrated phenol was then topped with 0.1 volume 100 mM Tris-HCl, pH 8.0 and stored at 4° C. For extraction, 30-40 mg of 1 mg ml$^{-1}$ COI1/ASK1 protein was mixed in small batches with equal parts equilibrated phenol at room temperature. The samples were inverted and incubated for 30 minutes until phase separation occurred. With 30 second vortexing, the samples were incubated at room temperature for 30 minutes and spun at 15,000 rpm for 5 minutes. The aqueous phase was removed as a primary extraction. Equal parts of a solution containing 25 mM Tris-HCl, pH 8.0 was added to the phenol and collected as above as a secondary extraction. The primary and secondary extractions were combined and diluted 10× in 25 mM Tris-HCl, pH 8.0, then further purified by gravity flow on Q sepharose high-performance anion exchange resin (GE Healthcare). Following column wash with 10× column volumes of 0.1 N formic acid, stepwise elution was performed with 23 column volumes of 0.1 N formic acid (Thermo Scientific) with increasing concentrations of ammonium formate (Sigma) from 0 to 2 M. Fractions were analyzed for phosphate content by the wet-ashing method with perchloric acid in Pyrex culture tubes (13×100 mm). Typically, samples of 50-100 µL were ashed with 100-200 mL 70% perchloric acid (purified by redistillation, Sigma). Ashing was performed by heating the sample over a Bunsen-type burner with continuous shaking to prevent bumping. When the sample stopped emitting white smoke, the reaction was considered complete and then heated to dryness. 500 µL of distilled water was added to the room temperature tubes and vortexed. 100 µL samples containing up to 10 nmol inorganic phosphate were assayed for phosphate by a modification of a published procedure (Sadrzadeh 1993). A total of 125 µL of acid molybdate color reagent was added and the samples were incubated and covered at room temperature for 12-14 hours (overnight) for full color development (total volume 225 µL). Plates were read at 650 nm and unknowns were determined from the linear regression of the standard curve (0-10 nmol NaH$_2$PO$_4$ per well). All assays were done in triplicate. Final fractions containing phosphate were combined and lyophilized repeatedly to remove residual ammonium formate.

After isolation of 150 nmol of the purified small molecule, a series of one-dimensional and two-dimensional NMR data were acquired, including a highly informative homonuclear total correlation (TOCSY) spectrum. NMR spectra were acquired on a Varian INOVA600 spectrometer equipped with a cold probe using 200 µM samples of purified compound X or synthetic inositol-1,2,4,5,6-pentakisphosphate (Cayman Chemical) dissolved in D$_2$O. TOCSY spectra were acquired with mixing times of 35 or 50 ms, processed with NMRPipe and visualized with NMRView.

Figure 18:
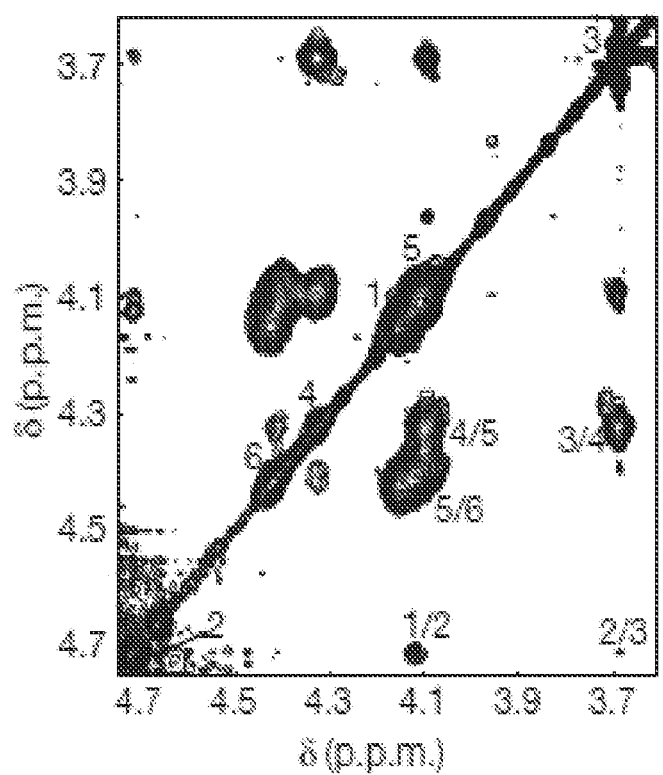
FIG. 18: Proton TOCSY spectrum of the purified cofactor. Numbers along the diagonal indicate the positions of the six protons of Ins(1,2,4,5,6)P$_5$. The cross-peaks corresponding to direct couplings are labeled. Other cross-peaks correspond to relayed connectivities.
Figure 19:
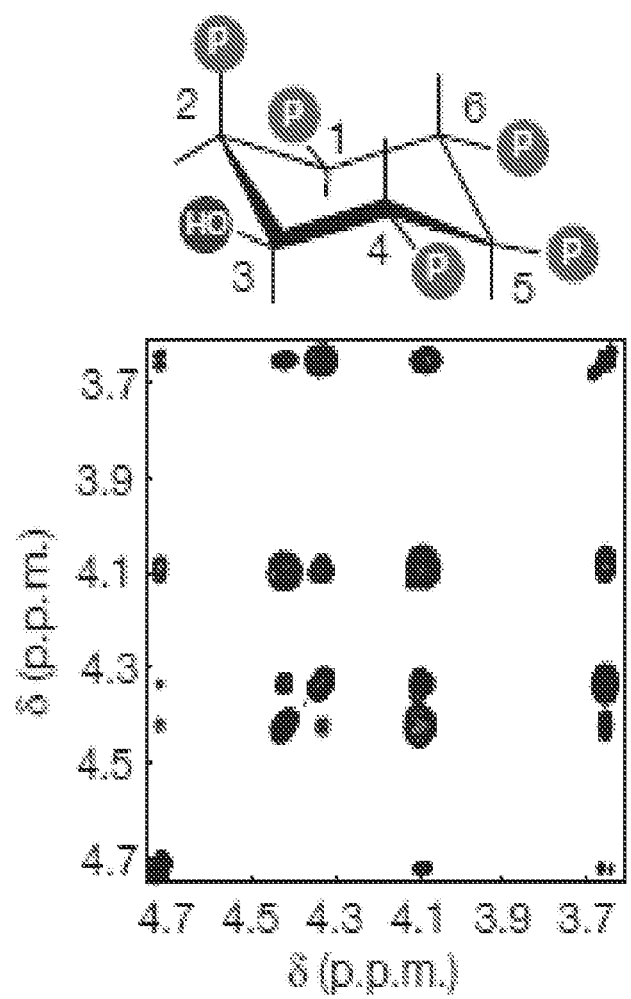
FIG. 19: TOCSY spectrum of a synthetic Ins(1,2,4,5,6)P$_5$ as a standard.

The observed chemical shifts and TOCSY cross-peak patterns are clearly characteristic of inositol phosphates (FIG. 18). A comparison with previously reported NMR spectra of various inositol phosphates established that the unknown compound is either D- or L-inositol-1,2,4,5,6-pentakisphosphate (Ins(1,2,4,5,6)P$_5$; FIG. 18). This conclusion was further supported by the TOCSY spectrum of synthetic Ins(1,2,4,5,6)P$_5$ (FIG. 19) and the subsequently acquired negative ion electrospray ionization mass spectrometry spectrum of the compound (FIG. 20).

Figure 20:
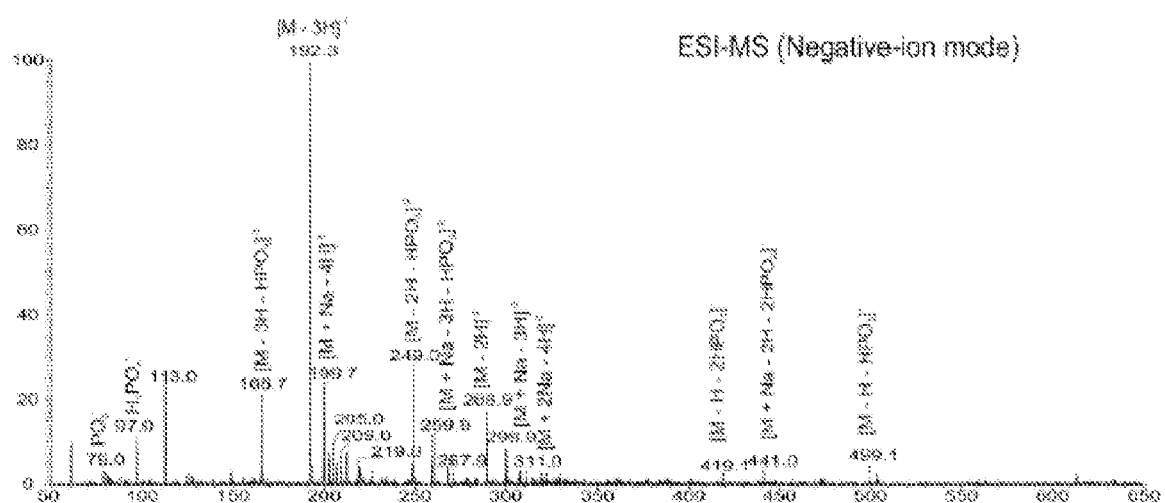
FIG. 20: Mass spectrometry analysis of Ins(1,2,4,5,6)P$_5$ purified from recombinant COI1/ASK1.

As shown in FIG. 20, the negative-ion ESI-MS spectrum of the unknown contained the major ion at m/z 192.3 ((579.8951−3×1.0078)/3), corresponding to the [M-3H]$^{3-}$ ion of inositol pentakisphosphate (InsP$_5$), and the ion at m/z 288.9 ((579.8951−2×1.0078)/2), corresponding to the [M-2H]$^{2-}$ ion of InsP$_5$. The [M-H]$^-$ ion expected at m/z 579.9 was absent. The ions seen at m/z 199.7 and 207.1 correspond to the sodiated ions of InsP$_5$ seen as the [M+Na-4H]$^{3-}$, and [M+2Na-5H]$^3$ ions, respectively; and the ions at m/z 299.9 and 311.9 correspond to the [M+Na-3H]$^{2-}$ and [M+2Na-4H]$^{2-}$ ions, respectively. The spectrum also contains ions at m/z 499 ([M-H—HPO$_3$]$^-$), 419 ([M-H-2HPO$_3$]$^-$), and 441 ([M+Na-2H-2HPO$_3$]$^-$), arising from various losses of the phosphate residues of the molecule. The presence of the ion at m/z 499 (579.9-HPO$_3$) is consistent with the observation of the ions at m/z 249 ([M-2H—HPO$_3$]$^{-2}$), 259.9 ([M+Na-3H—HPO$_3$]$^{-2}$), and 165.7 ([M-3H—HPO$_3$]$^{-3}$), representing the various deprotonated InsP$_4$ seen as doubly and triply charged anions. The ion at m/z 419 represents a deprotonated InsP$_3$ arising from loss of two HPO$_3$ residues; while the ion at m/z 441 represents a monosodiated InsP$_3$ anion. The presence of the ions at m/z 419 and 441 is also consistent with the observation of the doubly charged ions at m/z 209 and 219, corresponding to the [M-2H-2HPO$_3$]$^{-2}$ and [M+Na-3H-2HPO$_3$]$^{-2}$ ions, respectively. The assignments of the ions observed are listed in Table 3. These ions were also observed for Ins(1,2,3,4,5)P$_5$ and Ins(1,2,4,5,6)P$_5$ standards when subjected to ESI under the same condition, indicating that the unknown compound is an InsP$_5$. This InsP$_5$ structure is further confirmed by the MSn (n=2,3,4,5) mass spectra of the [M-3H]$^{3-}$ ion at m/z 192.3 and of the [M-2H]$^{2-}$ ion at m/z 288.9 deriving from the unknown compound and from the Ins(1,2,3,4,5)P$_5$ and Ins(1,2,4,5,6)P$_5$ standards.

TABLE 3

| Ions observed for IP5 by negative-ion ESI-MS | |
|---|---|
| m/z | Structure |
| 499 | [M − H − HPO$_3$]$^-$ |
| 441 | [M + Na − 2H − 2HPO$_3$]$^-$ |
| 419 | [M − H − 2HPO$_3$]$^-$ |
| 311 | [M + 2Na − 4H]$^{-2}$ |
| 300 | [M + Na − 3H]$^{-2}$ |
| 289 | [M − 2H]$^{-2}$ |
| 271 | [M + 2Na − 2H − 2HPO$_3$]$^{-2}$ |
| 268 | [M + K − 3H − 2HPO$_3$]$^{-2}$ |
| 259.9 | [M + Na − 3H − HPO$_3$]$^{-2}$ |
| 249 | [M − 2H − HPO$_3$]$^{-2}$ |
| 219 | [M + Na − 3H − 2HPO$_3$]$^{-2}$ |
| 212 | [M + Na + K − 5H]$^{-3}$ |
| 209 | [M − 2H − 2HPO$_3$]$^{-2}$ |
| 207 | [M + 2Na − 5H]$^{-3}$ |
| 203 | [M + Na − 4H]$^{-3}$ |
| 199.7 | [M + Na − 4H]$^{-3}$ |
| 192.3 | [M − 3H]$^{-3}$ |
| 165.7 | [M − 3H − HPO$_3$]$^{-3}$ |
| 97 | H$_2$PO$_4^-$ |
| 79 | PO$_3^-$ |

Figure 21:
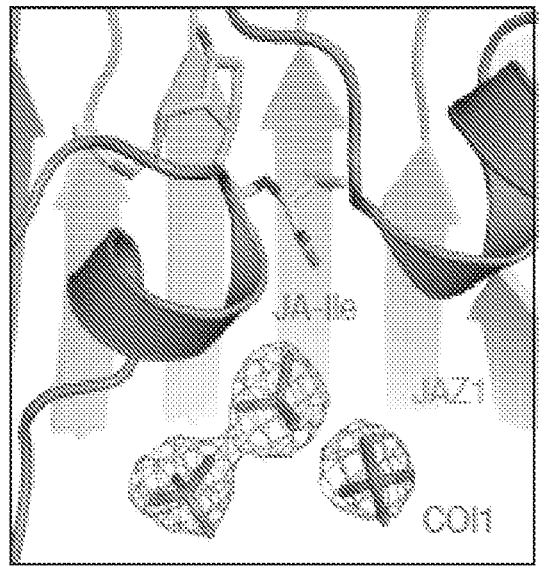
FIG. 21: A. Islands of positive $F_o$–$F_c$ electron density (red mesh) below the hormone-binding pockets, which probably belong to inorganic phosphate molecules from the crystallization solutions that displace InsP$_5$ from the InsP$_5$-binding site. B. Bottom view of a surface electrostatic potential representation of COI1 from positive (blue) to negative (red).
Figure 21:
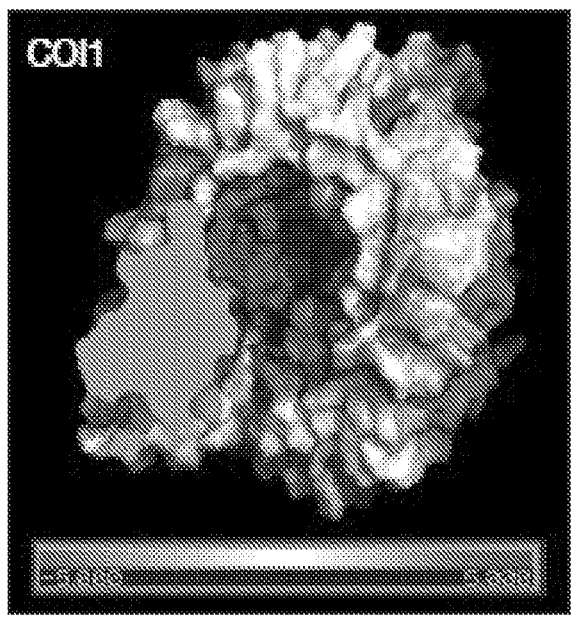
Figure 22:
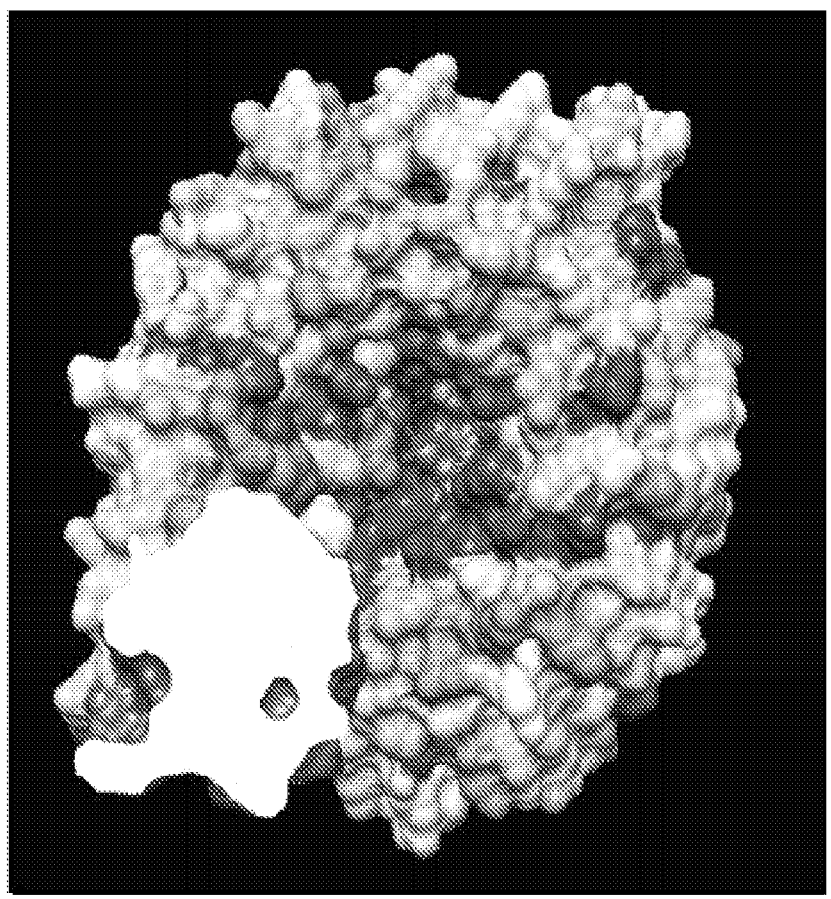
FIG. 22: Surface conservation mapping of COI1. Conservation mapping of COI1 surface based on sequences of COI1 orthologs from nine different species (*A. thaliana, H. brasiliensis, R. communis, P. trichocarpa, V. cinifera, P. sativum, S. lycopersicum, Z. mays, O. sativa*). Dark blue, light blue, and white surface regions indicate 98-100%, 60-98%, and <60% sequence conservation, respectively. The F-box portion of COI1 and its associated ASK1 are carved out for clarity reasons. Four phosphate molecules bound to COI1 are shown by red sticks. JAZ1 peptide and ASK1 are shown in grey.

Consistent with the binding of a small molecule cofactor, the crystal structure of COI1 (Example 3) showed strong unexplained electron densities clustered in the middle of the COI1 LRR domain. Like InsP$_6$ in TIR1, these extra densities in COI1 are located directly adjacent to the bottom of the ligand binding pocket of the jasmonate co-receptor, interacting with multiple positively charged COI1 residues (FIG. 21A). Unexpectedly, these islands of electron density cannot be explained by an Ins(1,2,4,5,6)P$_5$ molecule. Instead, their intensity, overall symmetry, and poor connectivity indicate that they belong to multiple free phosphate molecules. Because a high concentration of ammonium phosphate was used as the major precipitant for crystallizing the JA co-receptor, it was postulated that the InsP$_5$ molecule that co-purified with COI1 was later displaced by phosphate molecules in the crystallization drops. In support of this scenario, the concave surface of the COI1 solenoid fold surrounding the phosphates is highly basic and decorated with residues conserved in plant COI1 orthologs, indicating a functionally important surface area (FIGS. 9, 21B, 22).

The highly selective co-purification of two different inositol phosphates, InsP$_5$ and InsP$_5$, with two homologous plant hormone receptors, COI1 and TIR1, implies that the proper function of the two F-box proteins might require the binding of specific inositol phosphates. To assess the functional role of Ins(1,2,4,5,6)P$_5$ in the COI1/JAZ1 co-receptor, a protocol was developed for stripping the co-purified InsP$_5$ from COI1 without denaturing the protein. Briefly, proteins were mixed with 10% glycerol and incubated in 2 M ammonium phosphate, 100 mM Bis-Tris propane, pH 7.0, 200 mM NaCl, and 10% glycerol at 4° C. for >24 hours with a minimum of 3× buffer changes at 100× sample volume. Samples were then transferred to 20 mM Tris-HCl, pH 8.0, 200 mM NaCl, and 10% glycerol at 4° C. for >24 hours with a minimum of three buffer changes at 100× sample volume. Inositol phosphate rescue experiments were conducted according to the radioligand binding assays described above in the presence of 300 nM $^3$H-coronatine with nonspecific binding determined in the presence of 300 μM coronatine.

Figure 23:
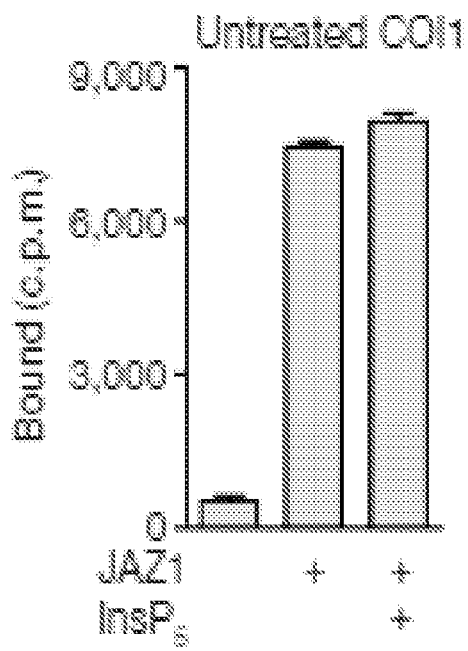
FIG. 23: A. Binding of $^3$H-coronatine at 100 nM to a complex of COI1 and JAZ1, with the addition of 1 μM synthetic Ins(1,2,4,5,6)P$_5$ (InsP$_5$). B. With extensive dialysis to remove the co-purified InsP$_5$ cofactor, 100 nM $^3$H-coronatine no longer binds dialyzed COI1 in the presence of JAZ1. Synthetic InsP$_5$ rescues binding. C. InsP$_5$ rescues the binding of 100 nM $^3$H-coronatine to dialyzed COI1/ASK1 in the presence of JAZ1 with an EC$_{50}$ of 27±12 nM.
Figure 23:
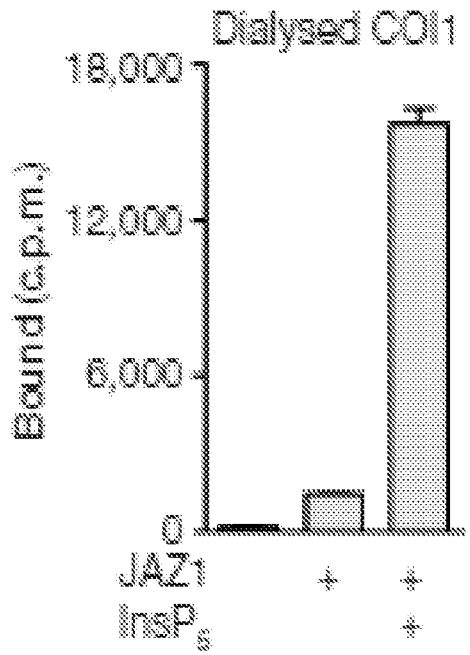
Figure 23:
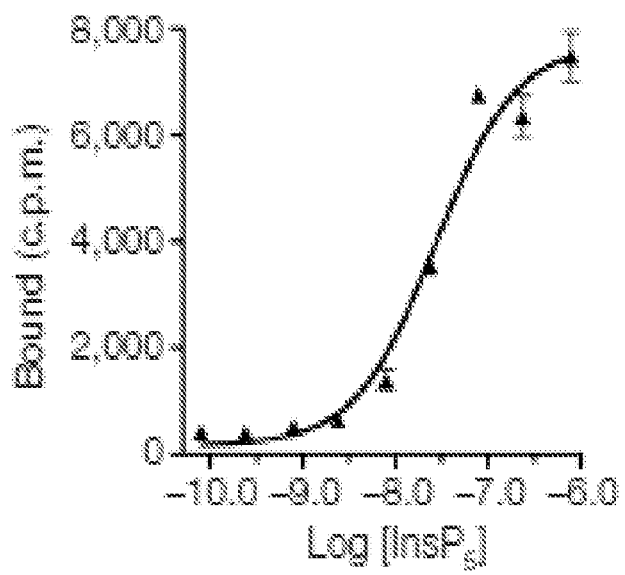

The resulting COI1/ASK1 complex was tested in a ligand-binding based reconstitution assay. As shown in FIG. 23A, untreated COI1 formed a high-affinity jasmonate co-receptor with JAZ1. Addition of exogenous Ins(1,2,4,5,6)P$_5$ did not significantly change its activity. In contrast, the dialyzed COI1 sample completely lacked ligand binding by itself and showed only trace activity in the presence of JAZ1. Supplementation with either synthetic Ins(1,2,4,5,6)P$_5$ (FIG. 23B) or the purified and NMR analyzed InsP$_5$ sample (data not shown) rescued the interaction in a dose-dependent manner and with a half-maximum effective concentration (EC$_{50}$) of 27 nM (FIG. 23C). From this reconstitution result, it was concluded that Ins(1,2,4,5,6)P$_5$ binding is crucial for the jasmonate coreceptor to perceive the hormone with high sensitivity.

Figure 24:
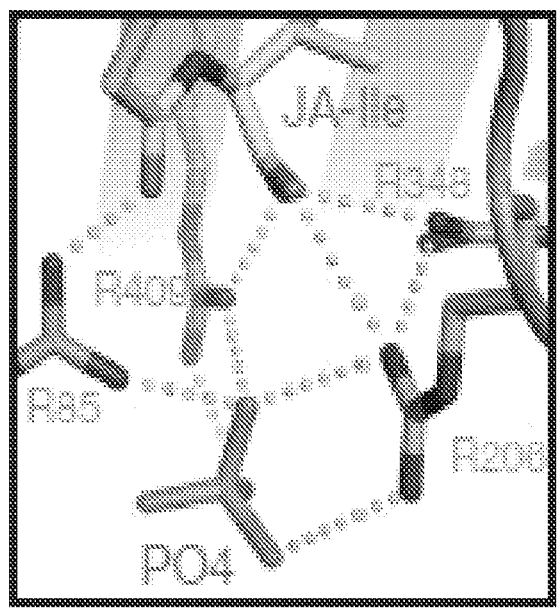
FIG. 24: Interwoven hydrogen bond network in the complex structure.

A close examination of the phosphate molecules in the available COI1 structure indicates a mechanism by which the inositol phosphate molecule may modulate the activity of the jasmonate co-receptor. Among four COI1-bound phosphates, one stands out by binding at a critical position in the jasmonate co-receptor. This phosphate molecule interacts simultaneously with four basic residues at the bottom of the ligand-binding pocket, namely Arg 206 in the JAZ1 degron and the three COI1 arginine residues that form the floor of the pocket. As a result, a tetragonal bipyramidal interaction network is formed among four molecules at the core of the jasmonate co-receptor assembly. The four arginines from COI1 and JAZ1 sit at the four corners of the central plane, interacting with the hormone above and the phosphate below (FIG. 24).

Figure 25:
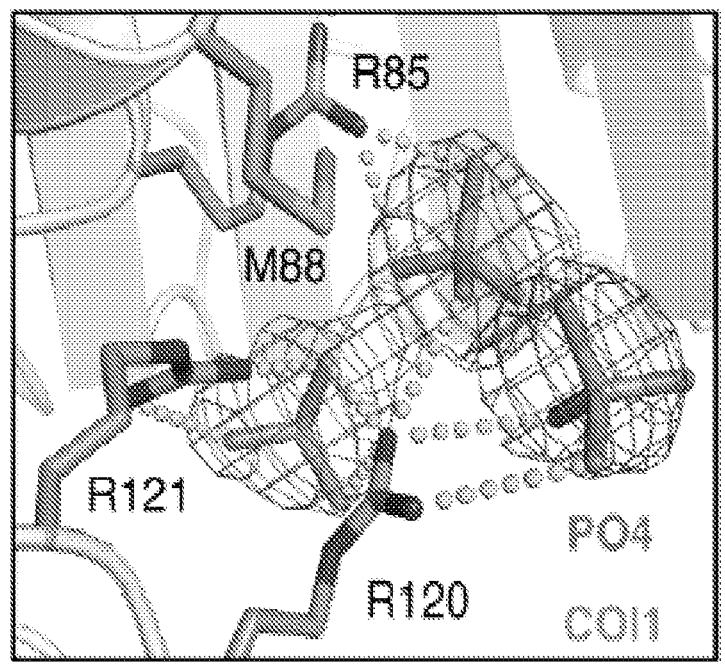
FIG. 25: A. Close-up view of COI1 residues (green stick) in close vicinity to the inorganic phosphates occupying the InsP5 binding pocket (orange stick, with along with positive $F_o$-$F_c$ density in red mesh). Hydrogen bonds are shown with yellow dashes. B. Interaction of wild-type COI1 and COI1 mutants with JAZ1 detected by yeast two-hybrid assay.
Figure 25:
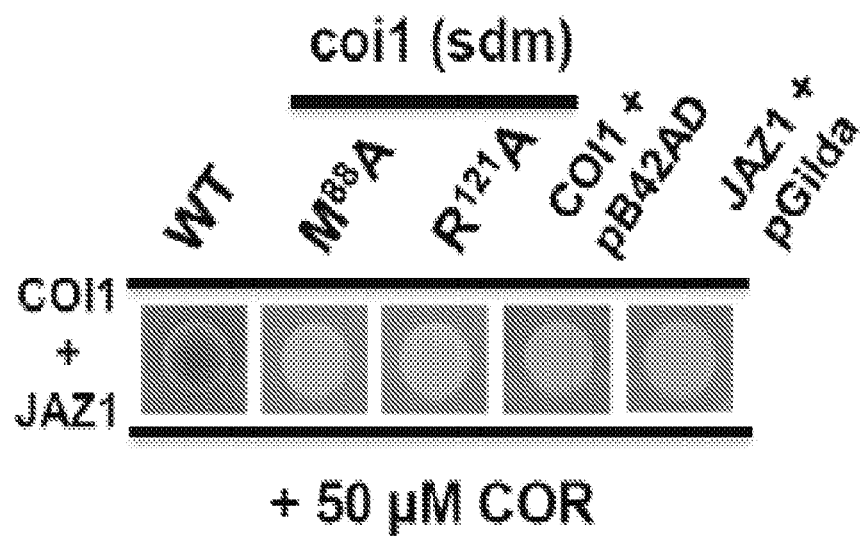

As the free phosphate molecule probably mimics the action of a phosphate group on InsP$_5$, this four-molecule junction, together with additional phosphate-COI1 interactions seen in the crystal, conceivably represents the structural basis for InsP$_5$ potentiation of the jasmonate coreceptor. Consistent with this interpretation, coronatine-induced formation of a COI1/JAZ1 complex was readily abolished by mutation of select COI1 residues adjacent to the phosphates, but not in contact with the hormone (FIG. 25).

Figure 14:
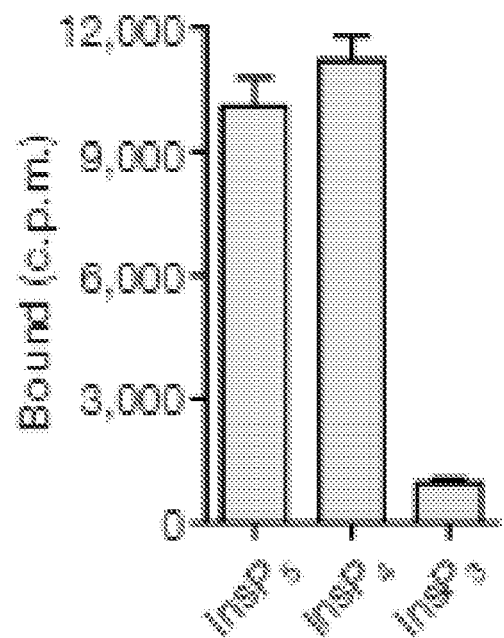
FIG. 14: A. Binding assays performed with 100 nM $^3$H-coronatine, dialyzed COI1, and 1 μM synthetic InsP$_5$. B. Saturation binding of $^3$H-coronatine to dialyzed COI1 in the presence of 1 μM of InsP$_5$ and InsP$_6$ at a $K_d$ of 30±5 nM and 37±8 nM, respectively. All results are the mean±s.e. of up to three experiments performed in duplicate.
Figure 14:
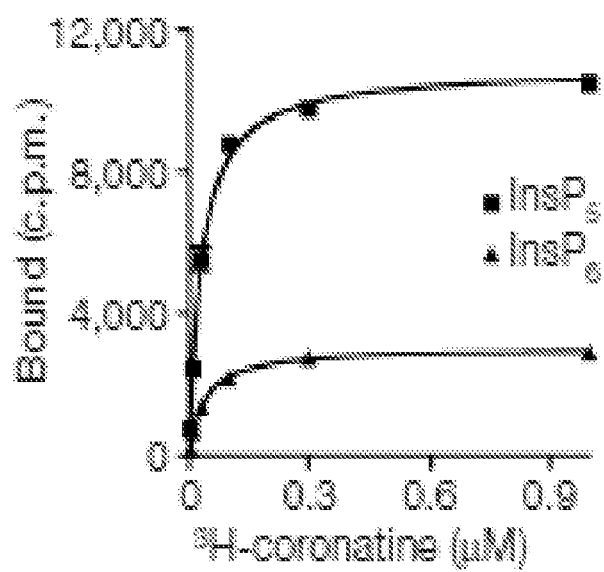

The reconstitution assay was used to further investigate the specificity of jasmonate co-receptor regulation by inositol phosphates (FIG. 14A). Notably, inositol-1,4,5,6-tetrakisphosphate supports the activity of the COI1/JAZ1 co-receptor, whereas the second messenger signaling molecule inositol-1,4,5-trisphosphate does not. Addition of a phosphate to InsP$_5$, which gives rise to InsP$_6$, is also not favorable for activity. Although saturation binding of $^3$H-coronatine is stimulated by both Ins(1,2,4,5,6)P$_5$ and InsP$_6$ with similar 1K$_d$ values (30 nM and 37 nM, respectively), the two inositol phosphates yield markedly different B$_{max}$ values for coronatine binding, indicating that InsP$_6$ is significantly less efficacious in activating the co-receptor despite having equal affinity as Ins(1,2,4,5,6)P$_5$ (FIG. 14B). Functional selectivity of COI1 for the inositol phosphate cofactor is consistent with the conservation of the putative inositol-phosphate-binding site, which is distinct in amino acid sequence from the InsP$_6$-binding site in TIR120 (FIG. 9).

Example 5

Targeted Degradation of a Target Protein

Green fluorescent protein (GFP) will be tagged with the JAZ1 +5 extension peptide tag of SEQ ID NO:6 in budding yeast cells (e.g., *Saccharomyces cerevisiae*) and/or mammalian cells. Where budding yeast cells are used, the tagged protein construct will be cloned into a standard yeast shuttling plasmid under the control of a strong, stable promoter, and the plasmid will be stably inserted into the yeast genome via chromosomal recombination sequences using methods well known in the art. Where mammalian cells are used, the gene encoding the tagged protein construct will be introduced via transient transfection or stable cell line generation.

The cells will be further engineered to express *Arabidopsis* COI1 or a homolog thereof under the control of an inducible promoter. For example, exogenous COI1 expression may be placed under the control of a galactose promoter, such that expression may be controlled by sugar ratio.

After stable GFP signal has been monitored qualitatively using standard techniques such as microscopy and/or quantitatively using techniques such as standard plate readers and/or flow cytometry methods, expression of *Arabidopsis* COI1 or a homolog thereof will be induced. COI1 expression should not significantly affect GFP signal levels.

Cells will be treated with titrating levels of coronatine. Cells will be harvested and fixed at various timepoints, and GFP signal will be quantified to determine the rate of GFP degradation. Degradation will increase as coronatine levels increase.

Additional experiments may be performed using one or more of the other JAZ1 peptide tags disclosed herein to determine the efficacy of slight changes to the peptide sequence. Similarly, additional experiments may be performed using molecules other than coronatine that bind to the COI1/JA-Ile binding pocket of COI1.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Adams Acta Crystallogr D 58:1948-1954 (2002)
2. Browse Annu Rev Plant Biol 60:183-205 (2009)
3. Brünger Acta Crystallogr D 54:905-921 (1998)
4. Cheng Biochem Pharmacol 22:3099-3108 (1973)
5. Chini Nature 448:666-671 (2007)
6. Chung Plant Cell 21:131-145 (2009)
7. Chung Plant J 63:613-622 (2010)
8. Delaglio J Biomol NMR 6:277-293 (1995)
9. Dharmasiri Nature 435:441-445 (2005)
10. Feys Plant Cell 6:751-759 (1994)
11. Fonseca Nature Chem Biol 5:344-350 (2009)
12. Grunewald EMBO Rep 10:923-928 (2009)
13. Johnson Methods Mol Biol 278:313-352 (2004)
14. Jones Acta Crystallogr A 47:110-119 (1991)
15. Katsir Proc Natl Acad Sci USA 105:7100-7105 (2008)
16. Kepinski Nature 435:446-451 (2005)
17. Koo Plant J 59:974-986 (2009)
18. Lorenzo Plant Cell 16:1938-1950 (2004)
19. Melcher Nature 462:602-608 (2009)
20. Melotto Plant J 55:979-988 (2008)
21. Miyazono Nature 462:609-614 (2009)
22. Murase Nature 456:459-463 (2008)
23. Nettleton J Mol Biol 281:553-564 (1998)
24. Nishimura Nature Methods 6:917-922 (2009)
25. Nishimura Science 326:1373-1379 (2009)
26. Ogawa Tetrahedr Lett 49:7124-7127 (2008)
27. Sadrzadeh J Pharmacol Toxicol Methods 30:103-110 (1993)
28. Sakamoto Proc Natl Acad Sci USA 98:8554-8559 (2000)
29. Santiago Nature 462:665-668 (2009)
30. Sheard Nature 468:400-405 (2010)
31. Shimada Nature 456:520-523 (2008)
32. Staswick Plant Cell 16:2117-2127 (2004)
33. Stephens Biochem J 275:485-499 (1991)
34. Suza Planta 227:1221-1232 (2008)
35. Tan Nature 446:640-645 (2007)
36. Thines Nature 448:661-665 (2007)
37. Xie Science 280:1091-1094 (1998)
38. Yan Plant Cell 19:2470-2483 (2007)
39. Yan Plant Cell 21:2220-2236 (2009)
40. Yin Nature Struct Mol Biol 16:1230-1236 (2009)
41. Zhang Proc Natl Acad Sci USA 100:14127-14132 (2003)
42. Zhou Mol Cell 6:751-756 (2000)

What is claimed is:

1. A method for targeted protein degradation in a cultured yeast or mammalian host cell comprising:
   a) introducing a DNA sequence encoding a target protein tagged with one or more peptide tags into said host cell, wherein said peptide tags consist of the amino acid sequence as set forth in SEQ ID NOs: 5, 6 or 7;
   b) introducing a DNA sequence encoding *Arabidopsis* protein COI1 or a homolog thereof into said host cell, wherein said *Arabidopsis* protein COI1 or a homolog thereof comprises the amino acid sequence as set forth in SEQ ID NOs: 15-27 or 28;
   c) culturing said host cell under conditions that result in expression of said tagged target protein and said *Arabidopsis* protein COI1 or a homolog thereof; and
   d) contacting said host cell from step (c) with a molecule that binds the COI1/jasmonyl-L-isoleucine (JA-Ile) binding pocket of COI1, wherein said molecule is selected from the group consisting of coronatine and JA-Ile, and wherein contacting of said molecule results in degradation of said tagged target protein.

2. A method for targeted protein degradation in a cultured yeast or mammalian host cell comprising:
   a) introducing a DNA sequence encoding one or more peptide tags into said host cell adjacent to a DNA sequence encoding an endogenous target protein, wherein said peptide tags consist of the amino acid sequence as set forth in SEQ ID NOs:5, 6 or 7;
   b) introducing a DNA sequence encoding *Arabidopsis* protein COI1 or a homolog thereof into said host cell, wherein said *Arabidopsis* protein COI1 or a homolog thereof comprises the amino acid sequence as set forth in SEQ ID NOs: 15-27 or 28;
   c) culturing said host cell under conditions that result in expression of said endogenous target protein tagged with said one or more peptide tags and said *Arabidopsis* protein COI1 or a homolog thereof; and
   d) contacting said host cell of step (c) with a molecule that binds the COI1/jasmonyl-L-isoleucine (JA-Ile) binding pocket of COI1, wherein said molecule is selected from the group consisting of coronatine and JA-Ile, and wherein contacting of said molecule results in degradation of said target protein.

3. The method of claim 1 or 2, further comprising the step of contacting said host cell with an inositol pentakisphosphate cofactor.

\* \* \* \* \*